US012664661B2

(12) United States Patent
Sutoko et al.

(10) Patent No.: US 12,664,661 B2
(45) Date of Patent: Jun. 23, 2026

(54) IMAGE PROCESSING APPARATUS AND IMAGE PROCESSING METHOD

(71) Applicant: HITACHI, LTD., Tokyo (JP)

(72) Inventors: Stephanie Sutoko, Tokyo (JP);
Hirokazu Atsumori, Tokyo (JP);
Ayako Nishimura, Tokyo (JP);
Tsukasa Funane, Tokyo (JP); Akihiko Kandori, Tokyo (JP)

(73) Assignee: HITACHI, LTD., Tokyo (JP)

( * ) Notice: Subject to any disclaimer, the term of this patent is extended or adjusted under 35 U.S.C. 154(b) by 246 days.

(21) Appl. No.: 18/732,824

(22) Filed: Jun. 4, 2024

(65) Prior Publication Data

US 2025/0104245 A1     Mar. 27, 2025

(30) Foreign Application Priority Data

Sep. 22, 2023     (JP) ................................. 2023-159279

(51) Int. Cl.
| | |
|---|---|
| *G06T 7/11* | (2017.01) |
| *G06T 7/00* | (2017.01) |
| *G16H 30/40* | (2018.01) |

(52) U.S. Cl.
CPC .............. *G06T 7/11* (2017.01); *G06T 7/0012* (2013.01); *G16H 30/40* (2018.01); *G06T 2207/10081* (2013.01); *G06T 2207/10088* (2013.01); *G06T 2207/20076* (2013.01); *G06T 2207/20104* (2013.01); *G06T 2207/20212* (2013.01); *G06T 2207/30016* (2013.01); *G06T 2207/30096* (2013.01)

(58) Field of Classification Search
None
See application file for complete search history.

(56) References Cited

U.S. PATENT DOCUMENTS

| | | | | |
|---|---|---|---|---|
| 10,628,972 B2 * | 4/2020 | Lee | ......................... | G06T 12/10 |
| 10,943,681 B2 * | 3/2021 | Yao | ................. | G06Q 10/06315 |
| 11,322,232 B2 * | 5/2022 | Lyman | ............. | G06Q 10/06315 |
| 11,551,795 B2 * | 1/2023 | Yao | ................. | G06Q 10/06315 |

(Continued)

FOREIGN PATENT DOCUMENTS

JP          2018102916 A       7/2018

*Primary Examiner* — Anand P Bhatnagar
(74) *Attorney, Agent, or Firm* — MATTINGLY & MALUR, PC

(57) ABSTRACT

An image processing apparatus includes: an inner region setting unit and a peripheral region setting unit setting, for an inner region in a medical image, a peripheral region in the medical image; an intensity value group probability distribution calculation unit calculating an inner region histogram for the inner region and calculating a peripheral region histogram for the peripheral region; a probability difference calculation unit calculating a probability difference distribution by calculating a difference value between the inner region histogram and the peripheral region histogram for each predetermined intensity value; a component image processing unit generating a component image based on the medical image; a detection range setting unit setting a detection range to each of the component images; a mask setting unit selecting a pixel to be highlighted for each of the component images based on the detection range; and a display processing unit outputting the highlighted component image.

11 Claims, 42 Drawing Sheets

(56)                    References Cited

U.S. PATENT DOCUMENTS

| | | | |
|---|---|---|---|
| 11,694,136 B2 * | 7/2023 | Lyman | G06Q 10/06315 |
| | | | 382/128 |
| 12,106,856 B2 * | 10/2024 | Keshwani | G06N 3/045 |
| 12,315,633 B2 * | 5/2025 | Li | G06T 7/0012 |
| 2016/0180525 A1 * | 6/2016 | Reynolds | G06T 7/0014 |
| | | | 382/131 |
| 2016/0292844 A1 * | 10/2016 | Karube | G06T 7/35 |
| 2018/0182481 A1 * | 6/2018 | Wakasugi | G06V 10/464 |
| 2020/0160975 A1 * | 5/2020 | Yao | G06Q 10/06315 |
| 2025/0045914 A1 * | 2/2025 | Wenzel | A61B 5/7267 |

* cited by examiner

100

COMPUTER

101 IMAGE ACQUISITION UNIT

102 INNER REGION SETTING UNIT

103 PERIPHERAL REGION SETTING UNIT

104 COMPONENT IMAGE PROCESSING UNIT

105 INTENSITY VALUE GROUP PROBABILITY DISTRIBUTION CALCULATION UNIT

106 PROBABILITY DIFFERENCE CALCULATION UNIT

107 DETECTION RANGE SETTING UNIT

108 MASK SETTING UNIT

109 MASK COMPILATION UNIT

110 DISPLAY PROCESSING UNIT

*FIG. 3*

COMPUTER 100

MEMORY 111

PROCESSING UNIT 112

COMMUNICATION DEVICE 113

Figure 13:
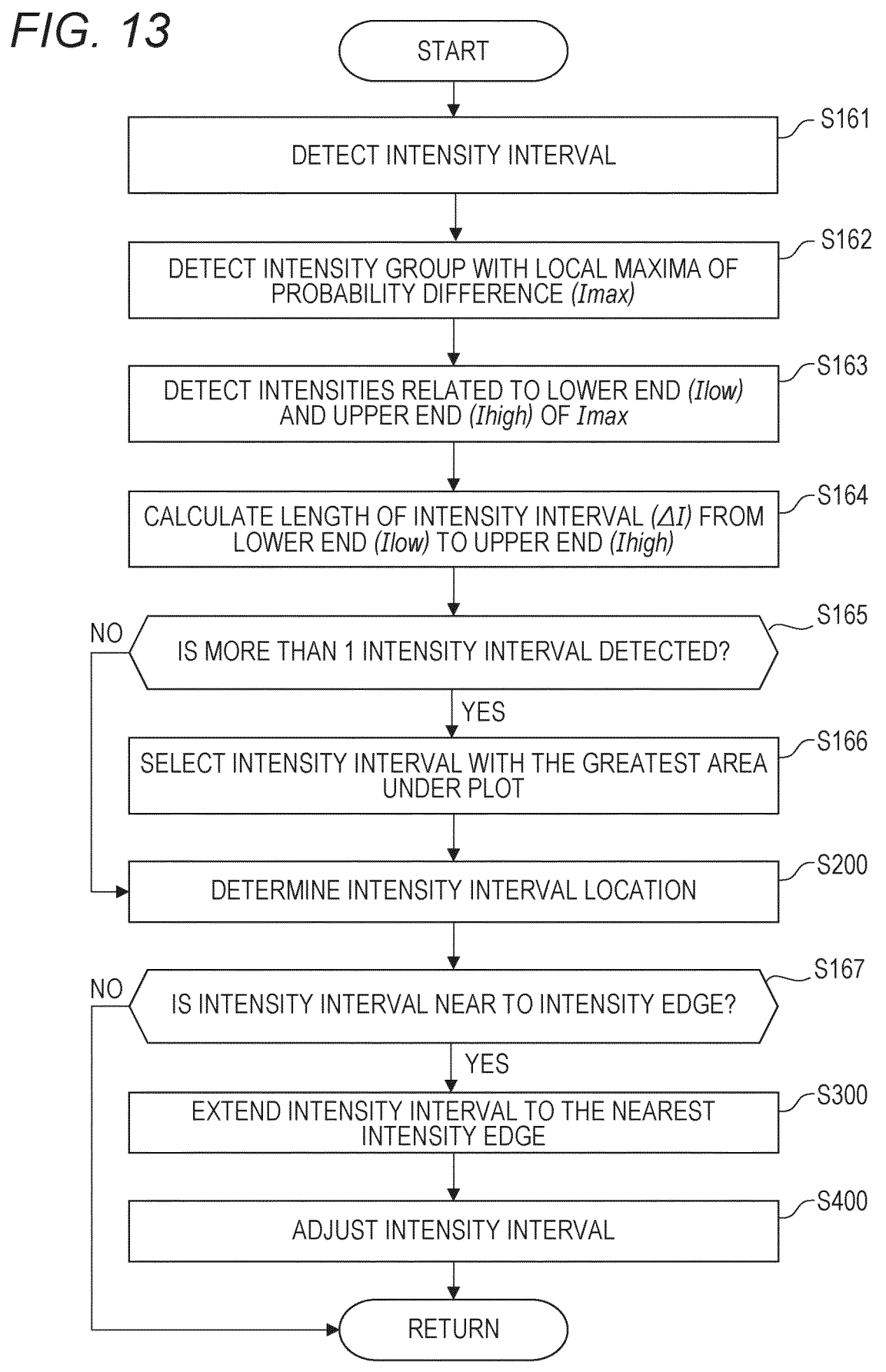

```
                    ┌─────────────┐
                    │    START    │
                    └─────────────┘
                           │
                           ▼
   ┌────────────────────────────────────────────────┐   S161
   │          DETECT INTENSITY INTERVAL              │
   └────────────────────────────────────────────────┘
                           │
                           ▼
   ┌────────────────────────────────────────────────┐   S162
   │  DETECT INTENSITY GROUP WITH LOCAL MAXIMA OF     │
   │       PROBABILITY DIFFERENCE (Imax)              │
   └────────────────────────────────────────────────┘
                           │
                           ▼
   ┌────────────────────────────────────────────────┐   S163
   │  DETECT INTENSITIES RELATED TO LOWER END (Ilow)  │
   │       AND UPPER END (Ihigh) OF Imax              │
   └────────────────────────────────────────────────┘
                           │
                           ▼
   ┌────────────────────────────────────────────────┐   S164
   │ CALCULATE LENGTH OF INTENSITY INTERVAL (ΔI) FROM │
   │     LOWER END (Ilow) TO UPPER END (Ihigh)        │
   └────────────────────────────────────────────────┘
                           │
                           ▼
NO ◁────◁ IS MORE THAN 1 INTENSITY INTERVAL DETECTED? ▷   S165
 │                         │
 │                        YES
 │                         ▼
 │ ┌──────────────────────────────────────────────┐   S166
 │ │ SELECT INTENSITY INTERVAL WITH THE GREATEST AREA│
 │ │              UNDER PLOT                         │
 │ └──────────────────────────────────────────────┘
 │                         │
 │                         ▼
 │ ┌──────────────────────────────────────────────┐   S200
 └▶│     DETERMINE INTENSITY INTERVAL LOCATION      │
   └──────────────────────────────────────────────┘
                           │
                           ▼
NO ◁────◁ IS INTENSITY INTERVAL NEAR TO INTENSITY EDGE? ▷  S167
 │                         │
 │                        YES
 │                         ▼
 │ ┌──────────────────────────────────────────────┐   S300
 │ │ EXTEND INTENSITY INTERVAL TO THE NEAREST        │
 │ │             INTENSITY EDGE                      │
 │ └──────────────────────────────────────────────┘
 │                         │
 │                         ▼
 │ ┌──────────────────────────────────────────────┐   S400
 │ │          ADJUST INTENSITY INTERVAL             │
 │ └──────────────────────────────────────────────┘
 │                         │
 │                         ▼
 │                 ┌─────────────┐
 └────────────────▶│   RETURN    │
                   └─────────────┘
```

START

S301 IS INTENSITY INTERVAL NEAR TO *I0* EDGE?

YES S302 MODIFY *Ilow* TO *I0*

NO S303 MODIFY *Ihigh* TO *Iend*

RETURN

START $\downarrow$

COMPUTE CUMULATIVE INTENSITY VALUE GROUP
PROBABILITY OF PERIPHERAL REGION IN INTENSITY
INTERVAL (FROM *Ihigh* TO *Ilow*) — S431

$\downarrow$

COMPUTE CUMULATIVE PROBABILITY DIFFERENCE IN
INTENSITY INTERVAL (FROM *Ihigh* TO *Ilow*) — S432

$\downarrow$

OUTPUT ASSOCIATED INTENSITY AND SELECTED
CUMULATIVE PROBABILITY — S433

$\downarrow$

RETURN

IMAGE PROCESSING APPARATUS AND IMAGE PROCESSING METHOD

CROSS-REFERENCE TO RELATED APPLICATION

The present application claims priority from Japanese application JP2023-159279, filed on Sep. 22, 2023, the content of which is hereby incorporated by reference into this application.

TECHNICAL FIELD

The present invention relates to a technique of an image processing apparatus and an image processing method.

BACKGROUND OF THE INVENTION

In order to specify a lesion of cerebral infarction or the like in a black-and-white contrast organ image including that of a brain, diagnosis of an experienced medical specialist or the like is currently required. In addition, work of putting a mark (color painting) on the image based on this diagnosis is performed manually and is therefore cumbersome.

JP 2018-102916 A discloses a control method, an information terminal, and a program in which "In a case where a lesion included in a designated target image is a texture type lesion, a probability image calculation unit 102 calculates for each pixel of the designated target image a probability value that the pixel is included in a lesion region. From a probability image acquired from the probability image calculation unit 102, an output unit 103 calculates a region that consists of pixels having a probability value equal to or greater than a first threshold as a candidate region, and calculates a region that consists of pixels having a probability value within a predetermined probability range including the first threshold as a correction region. An input unit 104 detects an input that is made by a user, by operating an operating device, to the pixel of the correction region displayed on a display by the output unit 103. A lesion region specification unit 105 specifies the lesion region based on the probability image acquired from the probability image calculation unit 102, the candidate region and the correction region acquired from the output unit 103, and user operation information acquired from the input unit 104" (see ABSTRACT).

SUMMARY OF THE INVENTION

The technique described in JP 2018-102916 A does not disclose an algorithm for identifying a lesion site (e.g. it is sufficient to use machine learning). That is, the technique described in JP 2018-102916 A does not describe an algorithm for identifying a lesion site, and it is difficult to improve determination accuracy of the lesion site.

In addition, a (semi) automatic lesion determination technique using a predetermined threshold of intensity data on the image and a (semi) automatic lesion determination technique by machine learning using a large number of images have been proposed so far. However, determination accuracy (performance) of these techniques for specifying a lesion is only 60% to 80%, which is not high.

In addition, the way of drawing the lesion site varies for each component constituting the brain, i.e. there are a component drawn in bright (white) color and a component drawn in dark (black) color. However, such an event is not considered in the related art.

The present invention has been made in view of such a background, and an object of the present invention is to highlight a region of interest in an image with high accuracy.

In order to solve the above problem, the present invention provides an image processing apparatus including: a region setting unit configured to set, for a first region set in a first image as a region including a region of interest in the first image, a second region in the first image, the second region being a region that is near the first region and that does not include the first region; an intensity value frequency distribution calculation unit configured to calculate a first intensity value frequency distribution that is information related to distribution of a number of pixels having a predetermined intensity value for the first region and calculate a second intensity value frequency distribution that is information related to distribution of a number of pixels having a predetermined intensity value for the second region; a probability difference calculation unit configured to calculate a probability difference frequency distribution by calculating a difference value between the first intensity value frequency distribution and the second intensity value frequency distribution for each of the predetermined intensity values; an image processing unit configured to generate a plurality of second images decomposed based on the first image in accordance with a predetermined criterion; a detection range setting unit configured to apply a detection range setting algorithm to each of the plurality of second images and set a detection range of the intensity value of the first image for each of the second images based on the difference value; a pixel selection unit configured to select pixel(s) to be highlighted for each of the plurality of second images based on the detection range set for each of the second images; and an output processing unit configured to output, to an output unit, a third image in which the pixel selected by the pixel selection unit is highlighted.

Other solutions will be appropriately described in embodiments.

According to the present invention, it is possible to highlight a region of interest in an image with high accuracy.

BRIEF DESCRIPTION OF THE DRAWINGS

FIG. 3 is a diagram illustrating a hardware configuration of the computer;

FIG. 12A is a diagram (part 1) illustrating a probability difference distribution;

FIG. 13 is a flowchart illustrating a detailed procedure of setting a detection range;

FIG. 36 is a diagram illustrating an example of the probability difference distribution based on the combined component image.

DESCRIPTION OF THE PREFERRED EMBODIMENTS

Next, modes for carrying out the present invention (referred to as "embodiments") will be described in detail with reference to the drawings as appropriate.

First Embodiment (Image Processing System Z)

Figure 1:
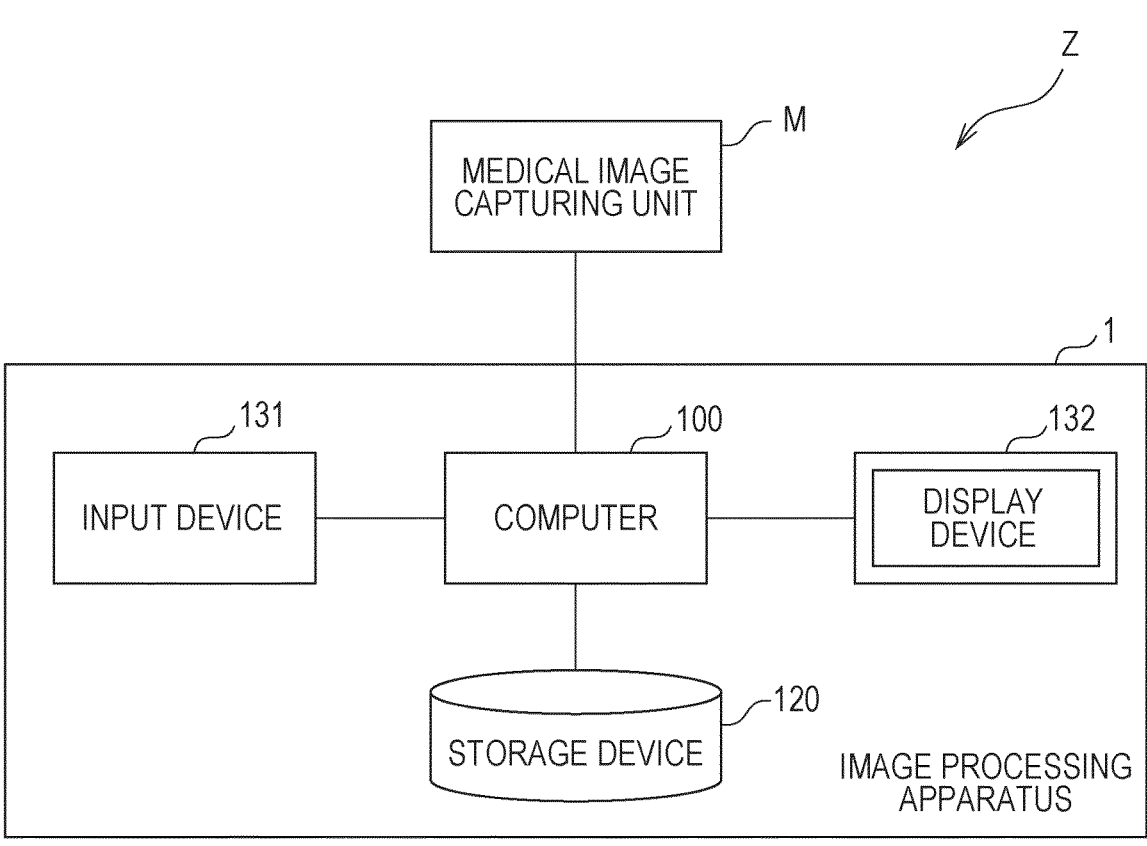
FIG. 1 is a diagram illustrating a configuration example of an image processing system according to a first embodiment.

FIG. 1 is a diagram illustrating a configuration example of an image processing system according to a first embodiment.

The image processing system Z includes a medical image capturing unit M. Further, the image processing system Z includes an image processing apparatus 1 that processes an image captured by the medical image capturing unit M. The image processing apparatus 1 sets a mask for highlighting a lesion site in a medical image 201 (see FIG. 7). The image processing apparatus 1 includes a computer 100, a storage device 120, an input device 131 as an input unit, and a display device 132: an output unit. Details of the computer 100 will be described later. The storage device 120 stores the medical image 201 acquired from the medical image capturing unit M, information such as a detection range and a mask to be described later, and the like. In the example illustrated in FIG. 1, the storage device 120 is integrated with the image processing apparatus 1, but the storage device 120 may be a device different from the image processing apparatus 1, for example, a database. The input device 131 includes a mouse, a keyboard, and the like. The display device 132 is a display.

The medical image capturing unit M is a magnetic resonance imaging (MRI) system, a computed tomography (CT) system, or the like. The medical image 201 is an MRI image, a CT image, or the like.

(Computer 100)

Figure 2:
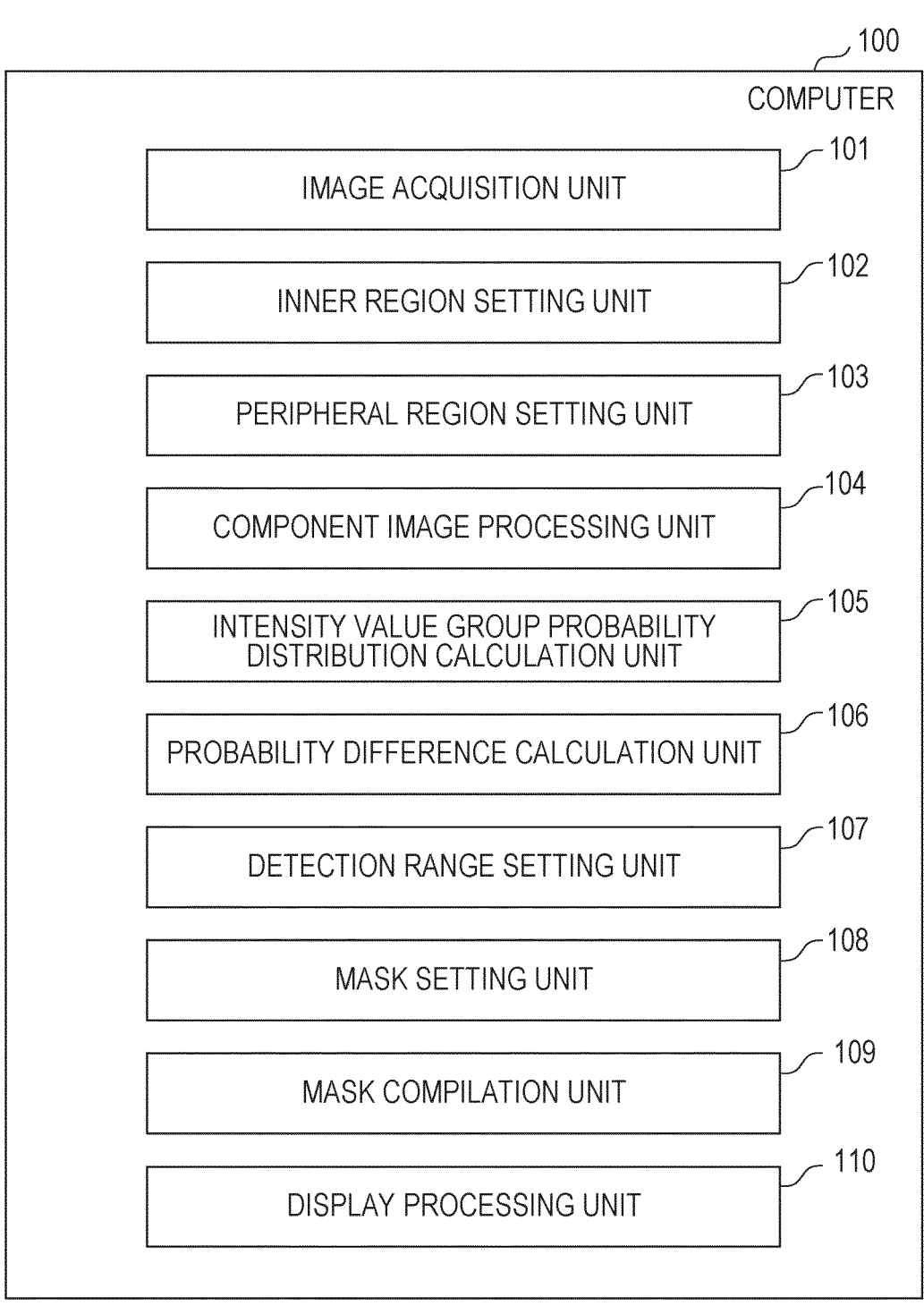
FIG. 2 is a diagram illustrating a configuration of a computer.

FIG. 2 is a diagram illustrating a configuration of the computer 100.

The computer 100 includes an image acquisition unit 101 and an inner region setting unit 102: a region setting unit. The computer 100 further includes a peripheral region setting unit 103: a region setting unit. The computer 100 further includes a component image processing unit 104: an image processing unit. The computer 100 includes an intensity value group probability distribution calculation unit 105: an intensity value frequency distribution calculation unit.

The computer 100 further includes a probability difference calculation unit 106. Then, the computer 100 includes a detection range setting unit 107. Further, the computer 100 includes a mask setting unit 108: a pixel selection unit, a mask compilation unit 109: a pixel selection unit, and a display processing unit 110: an output processing unit.

An image acquisition unit 101 acquires a first image: the medical image 201 (see FIG. 7) from the storage device 120. The inner region setting unit 102 sets a first region: an inner region 212 (see FIG. 7) in the medical image 201. Further, the peripheral region setting unit 103 sets a second region: a peripheral region 222 (see FIG. 7) in the medical image 201. The inner region 212 and the peripheral region 222 will be described later.

A component image processing unit 104 registers an anatomical model and the like in the medical image 201, and decomposes the medical image 201 into second images: component images 401 (see FIGS. 9B to 9E) which are images derived from an anatomical component. The component is an anatomical component of the brain, such as gray matter, white matter, cerebrospinal fluid, or soft tissue. However, there is a case where an image other than the brain is used as the medical image 201, and in such a case, a component other than the brain is used as the component.

An intensity value group probability distribution calculation unit 105 calculates a first intensity value frequency distribution: an inner region histogram 501 and a second intensity value frequency distribution: a peripheral region histogram 502, as described later with reference to FIGS. 11A to 11D. The inner region histogram 501 and the peripheral region histogram 502 are distributions of ratio between the number of pixels having luminance values in predetermined bins and the number of total pixels for the set inner region 212 and peripheral region 222.

Figure 12A:
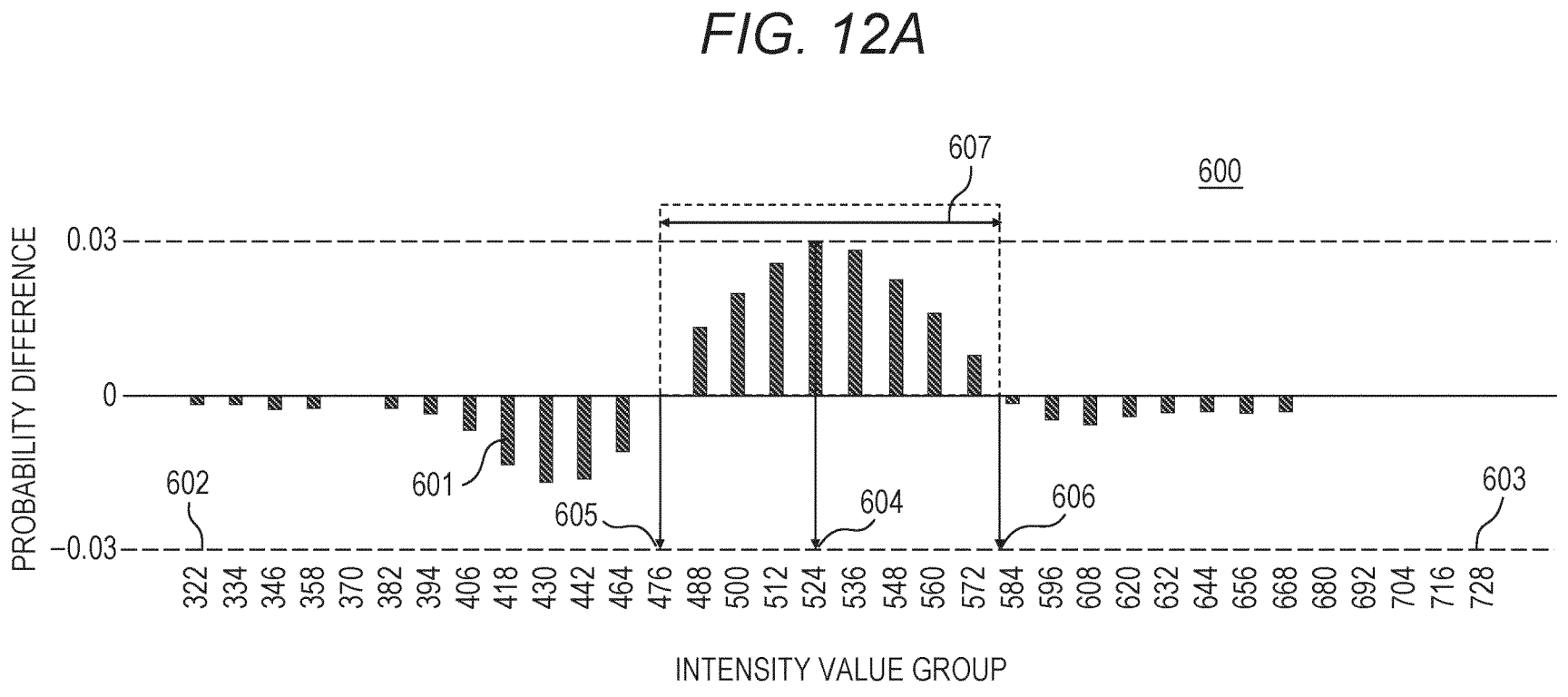
Figure 12B:
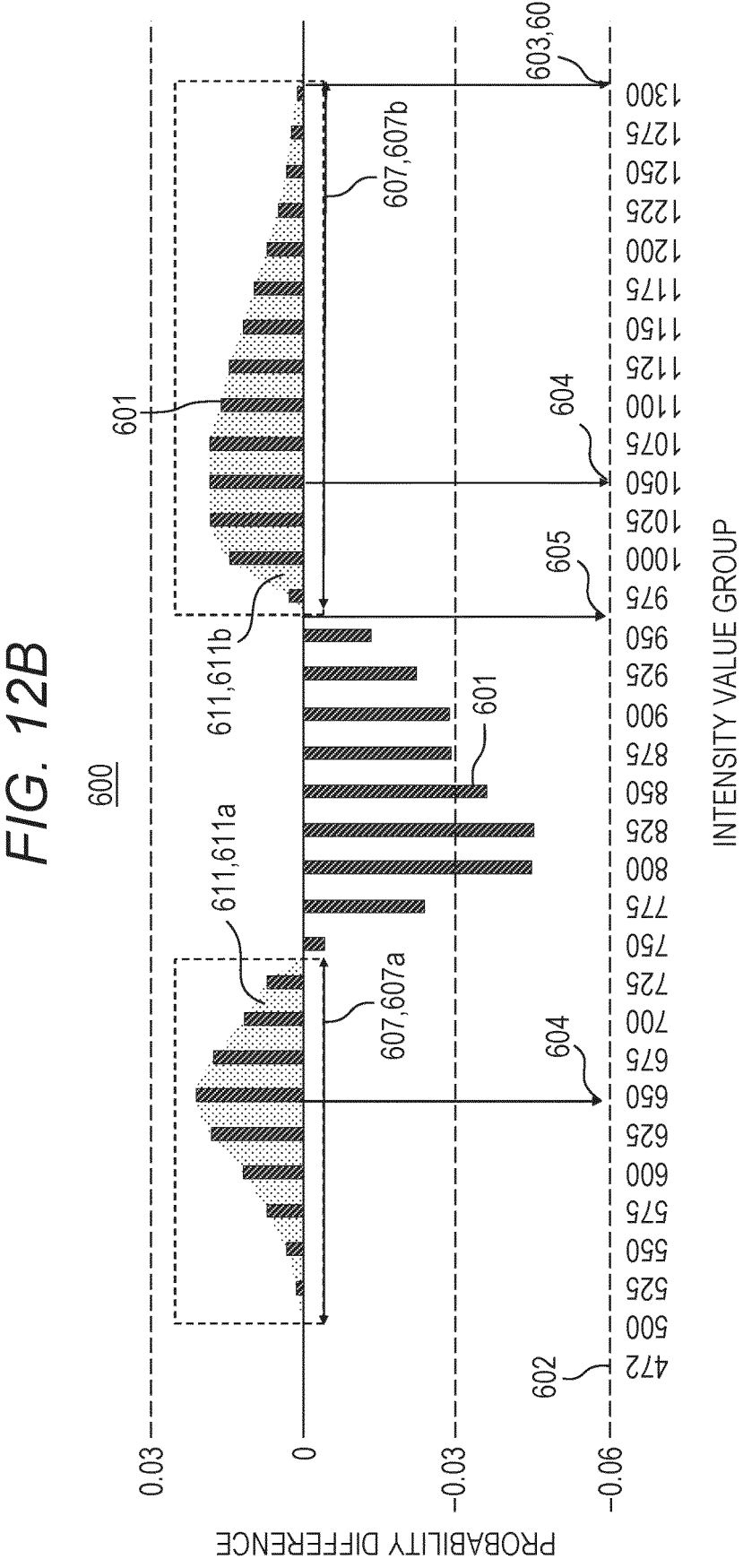
FIG. 12B is a diagram (part 2) illustrating a probability difference distribution.
Figure 12C:
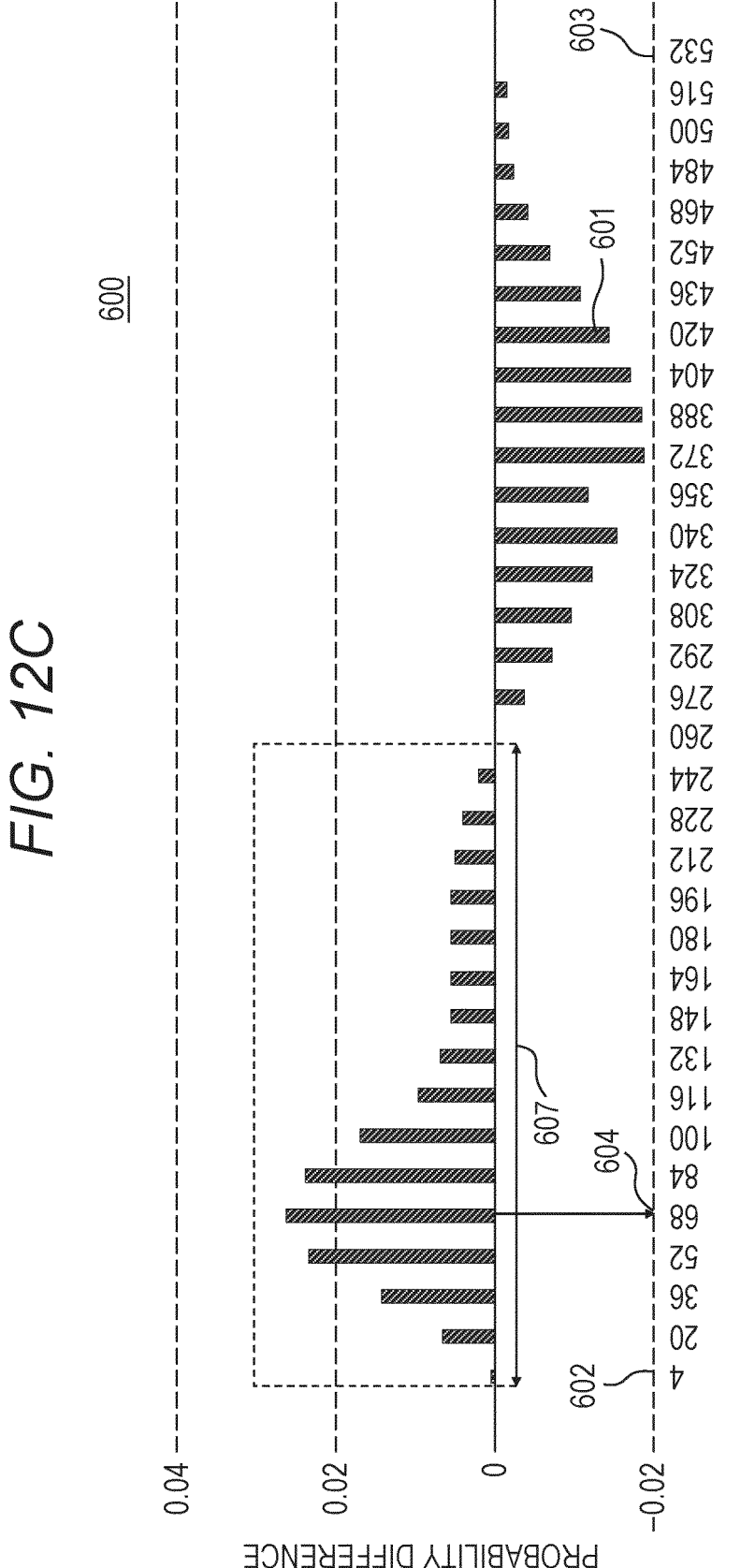
FIG. 12C is a diagram (part 3) illustrating a probability difference distribution.

The probability difference calculation unit 106 calculates a probability difference 601 obtained by subtracting the peripheral region histogram 502 from the inner region histogram 501 for each intensity value group, and generates a probability difference frequency distribution: a probability difference distribution 600 (see FIGS. 12A to 12C). The detection range setting unit 107 sets an intensity threshold representing a region of a lesion site (a lesion region 202) (see FIG. 7) in the medical image 201. The mask setting unit 108 highlights pixel(s) in the medical image 201 based on the set detection range.

Note that the intensity value group probability distribution calculation unit 105, the probability difference calculation unit 106, the detection range setting unit 107, and the mask setting unit 108 execute steps for each component. The mask compilation unit 109 synthesizes masks generated from all components. The display processing unit 110 displays, on the display device 132, a mask image 1003 (see FIG. 24E) in which pixels corresponding to the masks synthesized by the mask compilation unit 109 are highlighted.

(Hardware)

Figure 3:
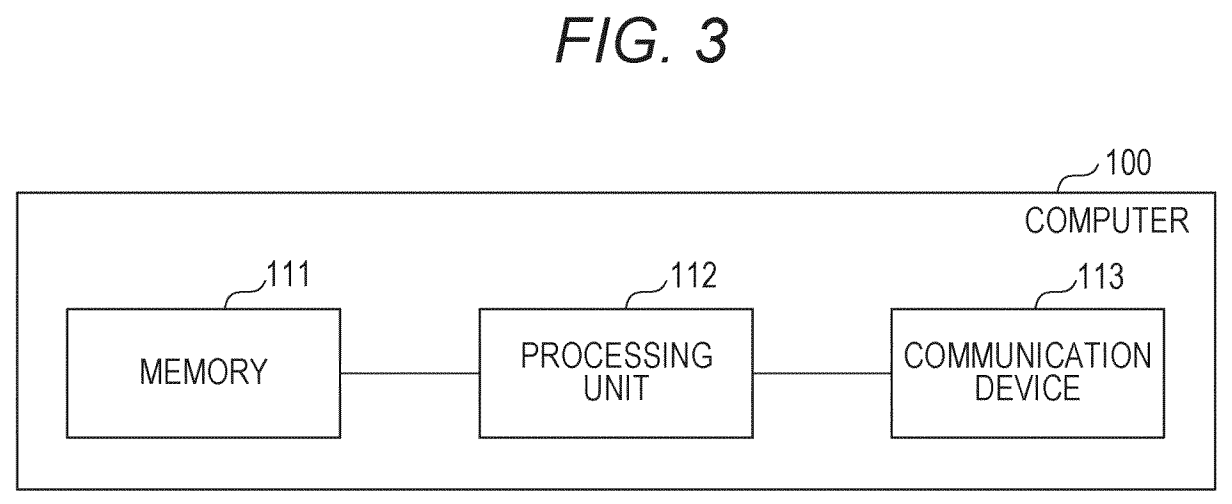

FIG. 3 is a diagram illustrating a hardware configuration of the computer 100.

As illustrated in FIG. 3, the computer 100 includes a memory 111 including a random access memory (RAM) and the like. The computer 100 also includes a processing unit 112 including a central processing unit (CPU) and a graphic processing unit (GPU). A communication device 113 transmits and receives information to and from the medical image capturing unit M illustrated in FIG. 1.

Then, the program stored in the storage device 120 is loaded into the memory 111, and the loaded program is executed by the processing unit 112. Thus, the image acquisition unit 101 to the display processing unit 110 illustrated in FIG. 2 are embodied.

(Overall Processing)

Figure 4:
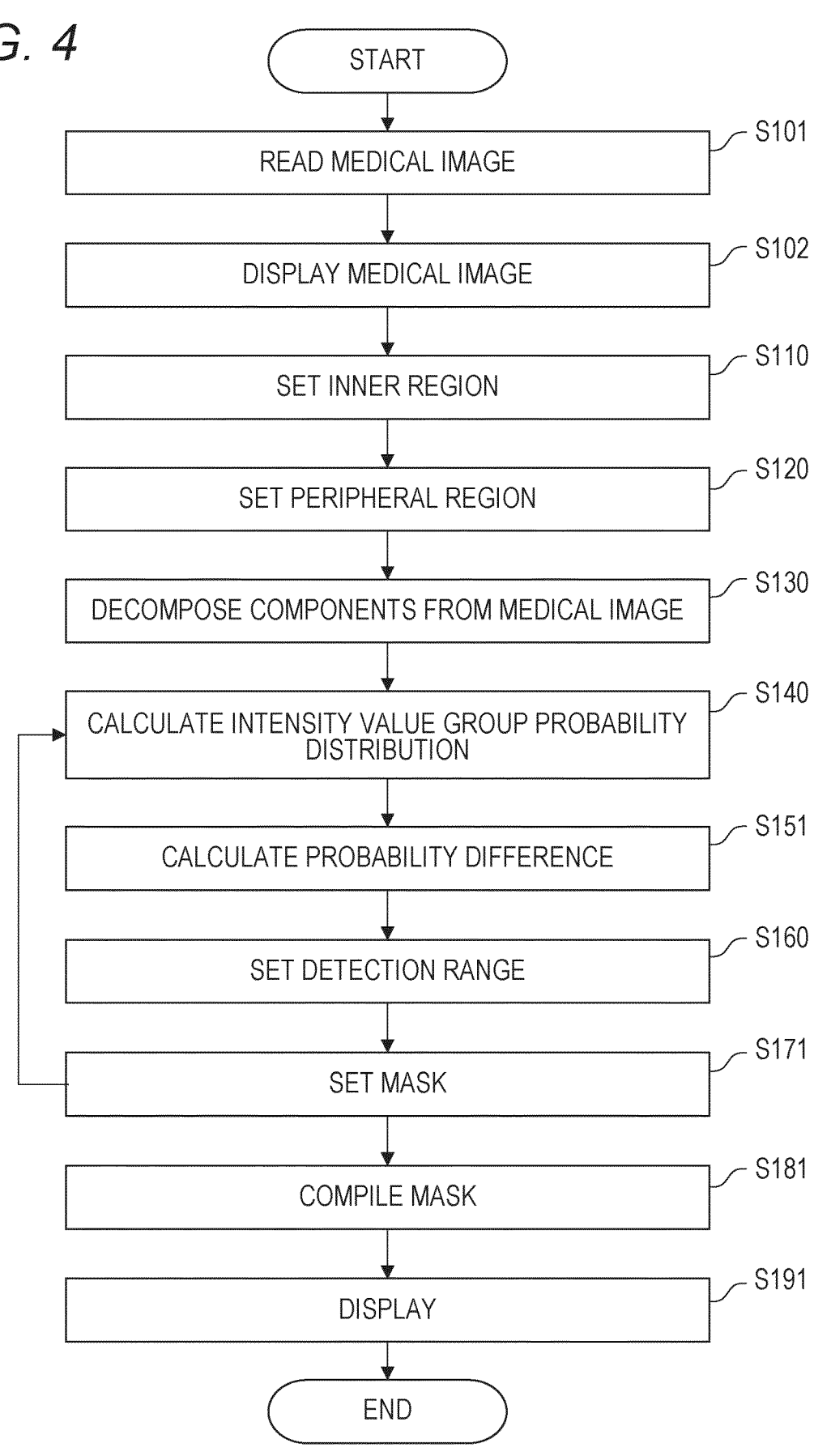
FIG. 4 is a flowchart illustrating an overall procedure of lesion site highlighting processing performed by the computer.

FIG. 4 is a flowchart illustrating an overall procedure of lesion site highlighting processing, i.e. an image processing method performed by the computer 100. A description is made with reference to FIG. 2 as appropriate. Details of each processing will be described later.

First, the computer 100 acquires the medical image 201 (see FIG. 7) captured by the medical image capturing unit M using a medical device. The acquired medical image 201 is stored in the storage device 120.

Next, the image acquisition unit 101 reads the medical image 201 stored in the storage device 120 (Read medical image: S101).

Subsequently, the display processing unit 110 displays the read medical image 201 on the display device 132 (Display medical image: S102).

Thereafter, the inner region setting unit 102 sets the inner region 212 (see FIG. 7) (Set inner region: S110: region setting step). Processing of step S110 will be described later.

Next, the peripheral region setting unit 103 sets the peripheral region 222 (see FIG. 7) based on the set inner region 212 (Set peripheral region: S120: region setting step). Processing of step S120 will be described later.

Then, the component image processing unit 104 decomposes the medical image 201 into images for each component (Decompose components from medical image: S130: component decomposition step). At this time, the component image processing unit 104 determines components of the medical image 201 for each pixel. The image decomposed for each component is referred to as a component image 401 (see FIGS. 9B to 9E). Processing of step S130 will be described later. In the stage of step S130, a combined component image 260 (see FIG. 34B) in which only the component image 401 related to the component of interest of a user is synthesized may be generated. The combined component image 260 will be described later in the third embodiment.

Subsequently, the intensity value group probability distribution calculation unit 105 calculates an intensity value group probability distribution 500 (see FIGS. 11A to 11D) for the inner region 212, and further calculates an intensity value group probability distribution 500 for the peripheral region 222 (Calculate intensity value group probability distribution: S140: intensity value frequency distribution calculation step). Processing of step S140 will be described later.

Thereafter, the probability difference calculation unit 106 subtracts the peripheral region histogram 502 (see FIG. 11) of the peripheral region 222 from the inner region histogram 501 (see FIG. 11) of the inner region 212 to calculate the probability difference 601 (see FIGS. 12A to 12C) (Calculate Probability difference: S151: probability difference calculation step). Processing of step S151 will be described later.

Then, the detection range setting unit 107 sets a detection range based on the probability difference 601 (Set detection range: S160: detection range setting step), and the mask setting unit 108 sets a mask (Set mask: S171: pixel selection step). Processing of step S160 will be described later. Thus, the lesion site is highlighted (masked) in each of the component images 401.

Note that the processing of steps S140, S151, S160, and S171 is performed for each of the component images 401. That is, the processing of steps S140, S151, S160, and S171 is looped until the processing is completed for all the component images 401.

Subsequently, the mask compilation unit 109 compiles (synthesizes) the mask (Compile mask: S181). In step S181, a mask highlighting the lesion site in each of the component images 401 is synthesized. As a result, masks highlighting the lesion sites detected in all the component images 401 are synthesized. When the combined component image 260 (see FIG. 34B) shown in the third embodiment is used, the processing of step S181 is omitted. Then, the display processing unit 110 displays (outputs), on the display device 132, the mask image 1003 (see FIG. 24E) in which the mask synthesized by the mask compilation unit 109 is highlighted in the medical image 201 (Display: S191: output step).
(Setting of Inner Region 212)

Next, setting processing of the inner region 212 by the inner region setting unit 102 will be described with reference to FIGS. 5 and 7.

Figure 5:
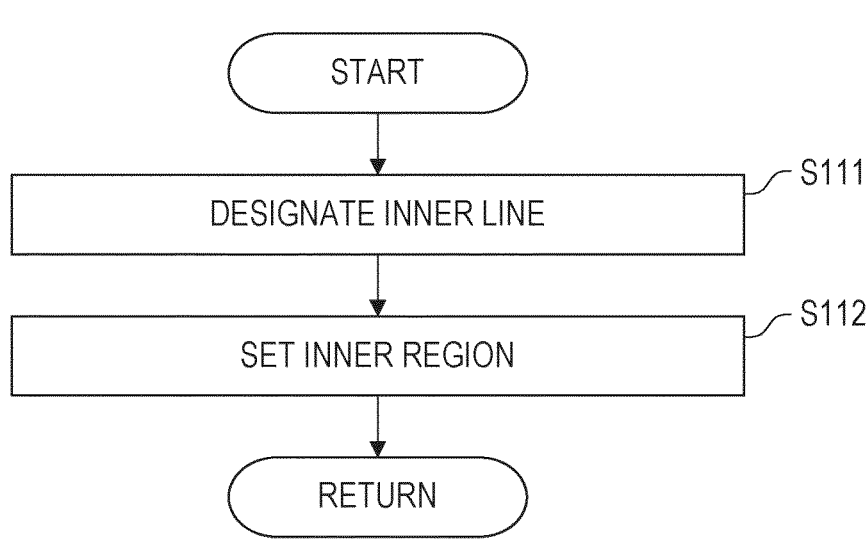
FIG. 5 is a flowchart illustrating a detailed procedure of inner region setting processing.
Figure 7:
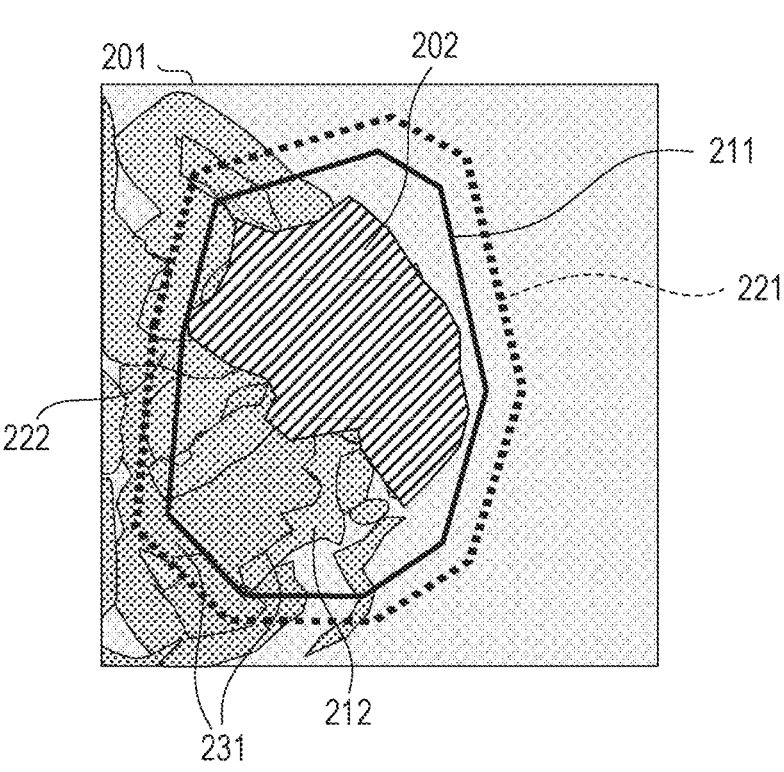
FIG. 7 is a view showing an example of an inner region and a peripheral region.

FIG. 5 is a flowchart illustrating a detailed procedure of inner region setting processing of setting the inner region 212 illustrated in FIG. 7. That is, FIG. 5 illustrates a detailed procedure of processing of step S110 in FIG. 4. FIG. 7 is a view showing an example of the inner region 212 and the peripheral region 222. FIG. 7 shows the medical image 201 related to the brain. A description is made with reference to FIGS. 2 and 3 as appropriate.

First, the user designates an inner line 211 in the medical image 201 shown in FIG. 7 (Designate inner line: S111 in FIG. 5). The user regards the inner line 211 as a lesion site in the medical image 201, and designates the inner line as a line surrounding the lesion region 202, i.e. a region of interest. Note that the lesion site is visually determined by the user (a doctor or the like) in advance. The user drags or clicks a plurality of points with a mouse (input device 131) or the like to designate the inner line 211. At this time, the user designates the inner line 211 such that the entire lesion region 202 is included as much as possible.

A region inside the inner line 211 is referred to as the inner region 212. In this manner, the inner region setting unit 102 sets the inner region 212 in the medical image 201 (Set inner region: S112 in FIG. 5). The inner line 211 is set via the input device 131 in this manner, as a result of which the inner region setting unit 102 sets the inner region 212 in the medical image 201. After completion of step S112 in FIG. 5, the computer 100 returns the processing to step S120 in FIG. 4.

In this manner, the inner region setting unit 102 sets the inner region 212 in the medical image 201 as a region including the lesion region 202 in the medical image 201.

Incidentally, the inner line 211 can be set not only as a polygon as shown in FIG. 7 but also as an ellipse.
(Setting of Peripheral Region 222)

Next, setting processing of the peripheral region 222 will be described with reference to FIGS. 6 and 7.

Figure 6:
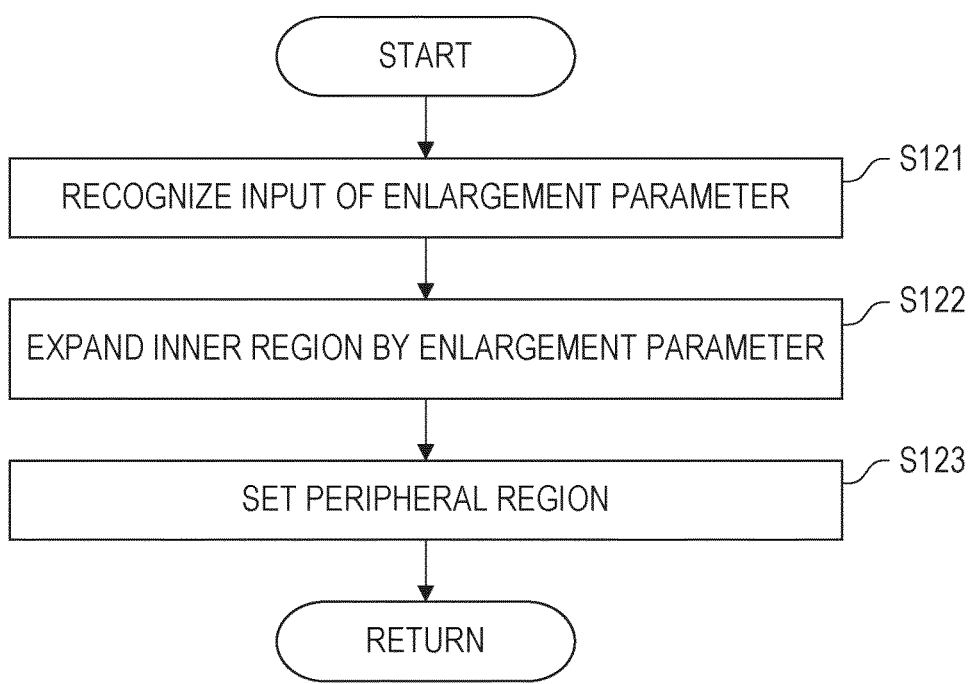
FIG. 6 is a flowchart illustrating a detailed procedure of peripheral region setting processing.

FIG. 6 is a flowchart illustrating a detailed procedure of peripheral region setting processing of the setting the peripheral region 222. That is, FIG. 6 illustrates a detailed procedure of step S120 in FIG. 4. FIG. 7 is a view showing an example of the inner region 212 and the peripheral region 222. FIG. 7 shows the medical image 201 related to the brain. A description is made with reference to FIGS. 2 and 3 as appropriate.

In the processing shown in FIG. 6, the peripheral region setting unit 103 sets the peripheral region 222 based on the inner line 211.

First, the peripheral region setting unit 103 acquires an enlargement parameter (x; x is a real number satisfying x>1) input by the user via the input device 131 (Recognize input of enlargement parameter: S121 in FIG. 6).

Subsequently, the peripheral region setting unit 103 sets an expanded region 231 (a region near the first region) obtained by multiplying the area of the inner region 212 shown in FIG. 7 by x (Expand inner region by enlargement parameter: S122 in FIG. 6). As shown in FIG. 7, the expanded region 231 is surrounded by an outer line 221. Further, the example shown in FIG. 7 shows a case where x=1.2.

Further, the peripheral region setting unit 103 sets a region between the outer line 221 and the inner line 211 in the medical image 201 as the peripheral region 222 (Set peripheral region: S123 in FIG. 6). As shown in FIG. 7, the peripheral region setting unit 103 sets the peripheral region 222 as a region being near the inner region 212 and not including the inner region 212. The peripheral region 222 is set not to include the lesion site.

In this manner, the peripheral region setting unit 103 sets the peripheral region 222, which is a region near the inner region 212 and does not include the inner region 212, with respect to the inner region 212, in the medical image 201.

After completion of step S123 in FIG. 6, the computer 100 returns the processing to step S130 in FIG. 4.
(Component Decomposition Processing)

Next, component decomposition processing in step S130 of FIG. 4 will be described with reference to FIG. 8 and FIGS. 9A to 9D.

Figure 8:
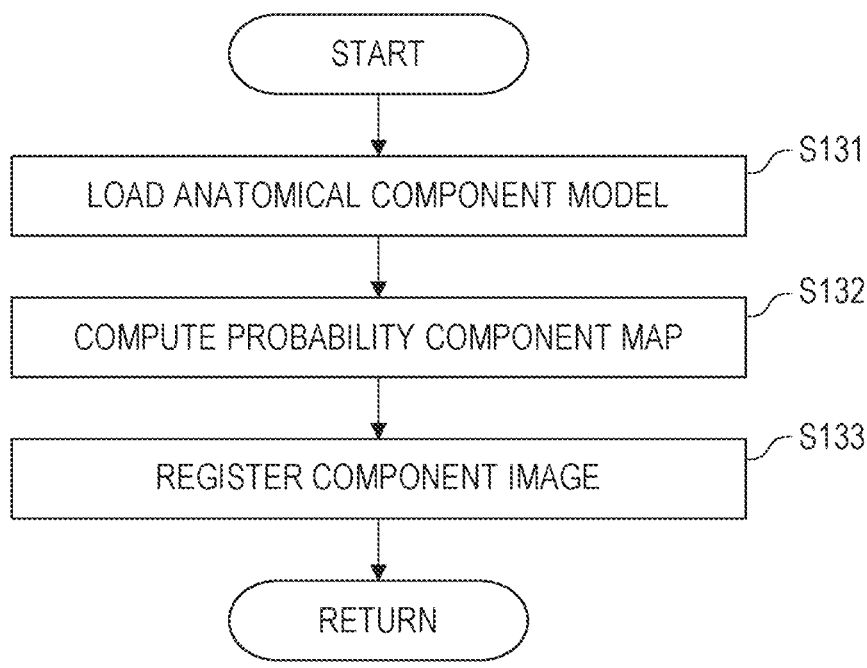
FIG. 8 is a flowchart illustrating a detailed procedure of component decomposition processing.
Figure 9A:
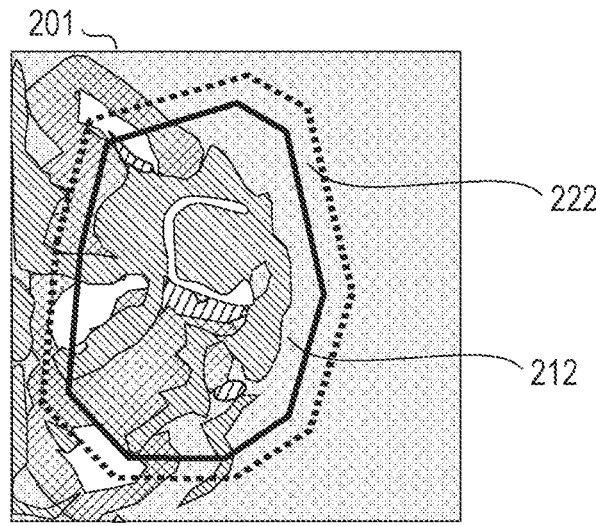
FIG. 9A is a view showing an example of a medical image.

FIG. 8 is a flowchart illustrating a detailed procedure of component decomposition processing of generating the component image 401 (see FIGS. 9B to 9E) from the medical image 201 in step S130 of FIG. 4. Further, FIG. 9A shows an example of the medical image 201, and FIGS. 9B to 9E are views each showing an example of the component image 401.

First, the component image processing unit 104 reads an anatomical component model (not illustrated) or the like stored in the storage device 120 (Load anatomical component model: S131 in FIG. 8).

Next, the component image processing unit 104 computes a probability component map related to component information of each pixel according to the read anatomical component model (Compute probability component model: S132 in FIG. 8). As a result, the feature of the pixel for each component is computed.

Then, the component image processing unit 104 generates the component image 401 by referring to the probability component map for each pixel of the medical image 201 and determining which component the current processing target belongs to has the highest probability (predetermined criterion). The component image processing unit 104 registers the generated component image 401 in the storage device 120 illustrated in FIG. 1 (Register component image: S133 in FIG. 8).

As a result, the medical image 201 is decomposed into the component images 401 for each component (gray matter, white matter, etc.).

Note that the generation of the component image 401 (decomposition of the medical image 201) is not limited to the procedures of steps S131 to S133.

(Component Image 401)

Figure 9B:
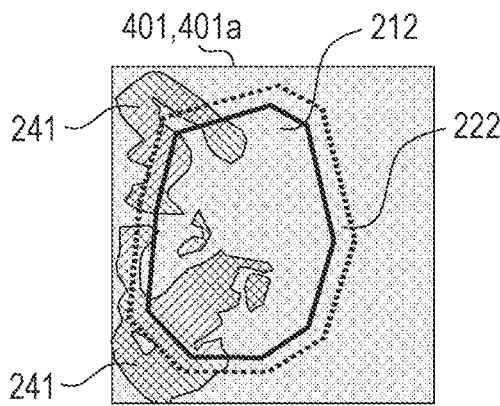
FIG. 9B is a view (part 1) showing an example of a component image.
Figure 9C:
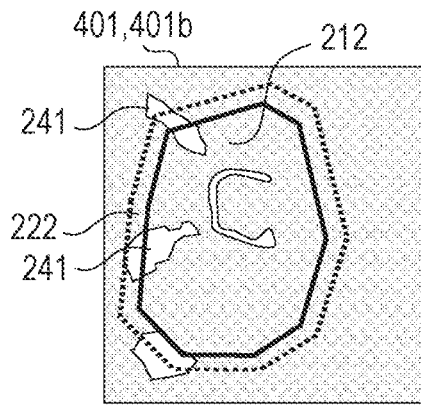
FIG. 9C is a view (part 2) showing an example of a component image.
Figure 9D:
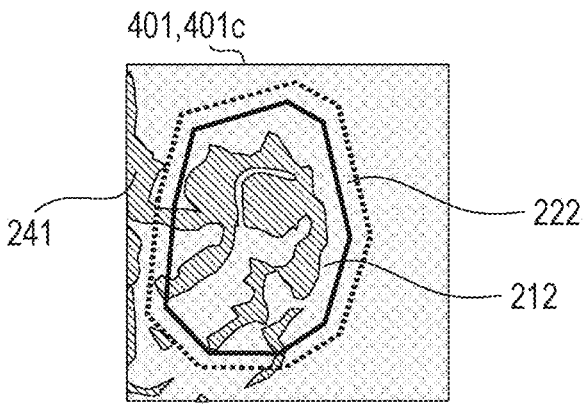
FIG. 9D is a view (part 3) showing an example of a component image.
Figure 9E:
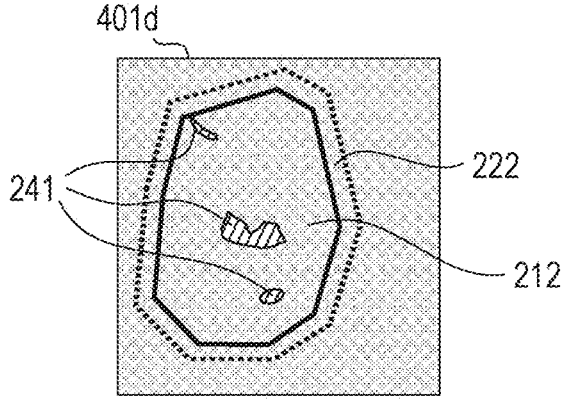
FIG. 9E is a view (part 4) showing an example of a component image.

FIG. 9A shows the medical image 201, FIG. 9B shows a component image 401a (401), FIG. 9C shows a component image 401b (401), FIG. 9D shows a component image 401c (401), and FIG. 9E shows a component 401d (401). The component image 401a shown in FIG. 9B is, for example, an image showing a component of gray matter, and the component image 401b shown in FIG. 9C is an image showing a component of white matter. Further, the component image 401c shown in FIG. 9D is an image showing cerebrospinal fluid, and the component image 401d shown in FIG. 9E is an image showing soft tissue. Incidentally, the component images 401a to 401d are synthesized to form the medical image 201 shown in FIG. 9A. As described above, in the present embodiment, the medical image 201 is the medical image 201 captured by the medical image capturing unit M, and is an image related to the brain.

In addition, the medical image 201 in FIG. 9A shows the inner region 212 and the peripheral region 222 set in steps S110 and S120 in FIG. 4. Similarly, the inner region 212 and the peripheral region 222 are set in the component images 401a to 401d shown in FIGS. 9B to 9E. That is, the inner region 212 and the peripheral region 222 set in steps S110 and S120 in FIG. 4 are successively used in the component images 401a to 401d. In FIGS. 9B to 9D, the components are present across the boundary between the inner region 212 and the peripheral region 222 as indicated by reference numeral 241. However, in FIG. 9E, the components indicated by reference numeral 241 are present only in the inner region 212.

In this manner, the component image processing unit 104 generates a plurality of component images 401 decomposed based on the medical image 201 in accordance with a predetermined criterion (which component the image belongs to).

After completion of step S133 in FIG. 8, the computer 100 returns the processing to step S140 in FIG. 4.

(Intensity Value Group Probability Distribution Calculation Processing)

Next, the calculation of the intensity value group probability distribution 500 in step S140 of FIG. 4 will be described in detail with reference to FIG. 10 and FIGS. 11A to 11D. A description is made with reference to FIGS. 9B to 9E as appropriate.

Figure 10:
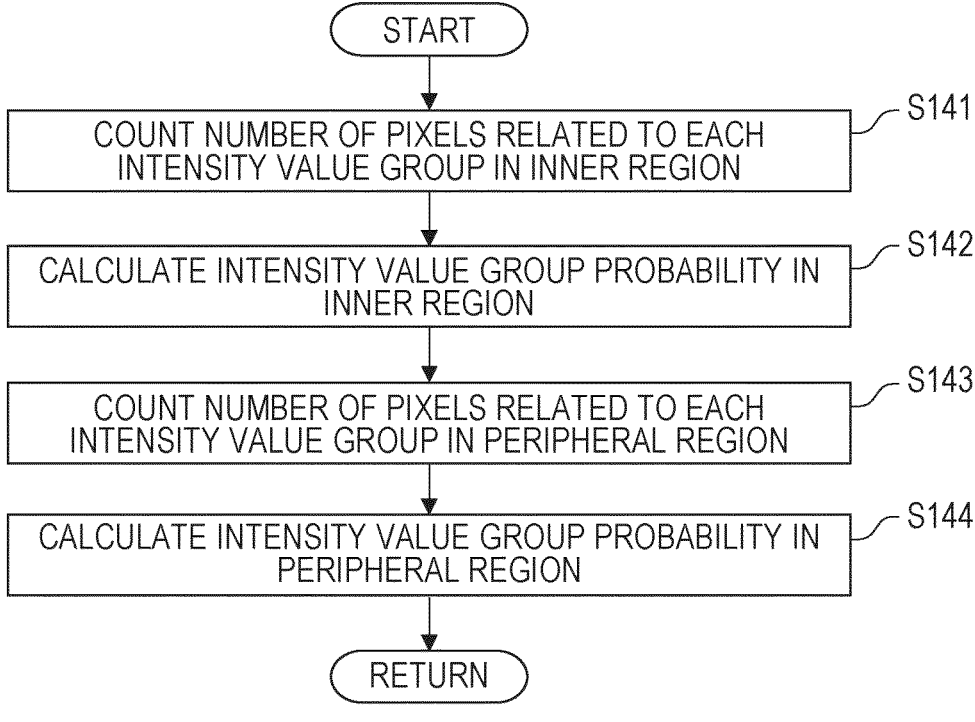
FIG. 10 is a flowchart illustrating a detailed procedure of intensity value group probability distribution calculation.

FIG. 10 is a flowchart illustrating a detailed procedure of calculating the intensity value group probability distribution in step S140 of FIG. 4. FIGS. 11A to 11D are diagrams each illustrating an example of the intensity value group probability distribution 500 in the inner region 212 and the peripheral region 222 for each of the component images 401.

First, the intensity value group probability distribution calculation unit 105 counts the number of pixels having the intensity for each intensity value group in the inner region 212 of the component image 401 to be processed (Count number of pixels related to each intensity value group in inner region: S141). For example, the intensity value group probability distribution calculation unit 105 counts the number of pixels "n1" having pixel intensities "488" to "499" (the pixels are referred to as an intensity value group "500") in the inner region 212 in the component image 401a of FIG.

9B. The counted result corresponds to the number of pixels having a predetermined intensity value.

Then, the intensity value group probability distribution calculation unit 105 divides the number of pixels of the intensity value group by the total number of pixels in the inner region 212 (the number of pixels constituting the inner region 212). As a result, for example, the intensity value group probability distribution calculation unit 105 calculates a probability (referred to as an intensity value group probability) related to the pixels of the intensity value group "500" in the inner region 212 of the component image 401a (Calculate intensity value group probability in inner region: S142 in FIG. 10).

Hereinafter, definition of the intensity value group will be described. A group of a plurality of intensity values is referred to as the intensity value group. For example, each of "310 to 321", "322 to 333", . . . , "704 to 715", and "716 to 727" is referred to as the intensity value group. In FIGS. 11A to 11D, the bin width is "12", but the bin width is not limited to "12". Further, the intensity value groups are not necessarily aligned as indicated by reference numerals 503a, 503b, 503c, and 503d illustrated in FIGS. 11A to 11D, but may be aligned between components.

Furthermore, an intensity value group corresponding to "n to m" (n and m are natural numbers including 0) is referred to as an intensity value group "m+1". For example, an intensity value group corresponding to the intensity values "320 to 321" is described as an intensity value group "322".

For example, in the inner region 212 of the component image 401a shown in FIG. 9B, the total number of pixels included in the inner region 212 is assumed to be "N1". Further, the number of pixels belonging to the intensity value group "500" in the inner region 212 of the component image 401a is assumed to be "n1". In this case, the intensity value group probability of the intensity value group "500" in the inner region 212 of the component image 401a is "n1/N1".

As a result, the intensity value group probabilities are shown as bins on the histogram 501a in the intensity value group "500".

The intensity value group probability distribution calculation unit 105 performs the processing of steps S141 and S142 for all the intensity value groups.

Figure 11A:
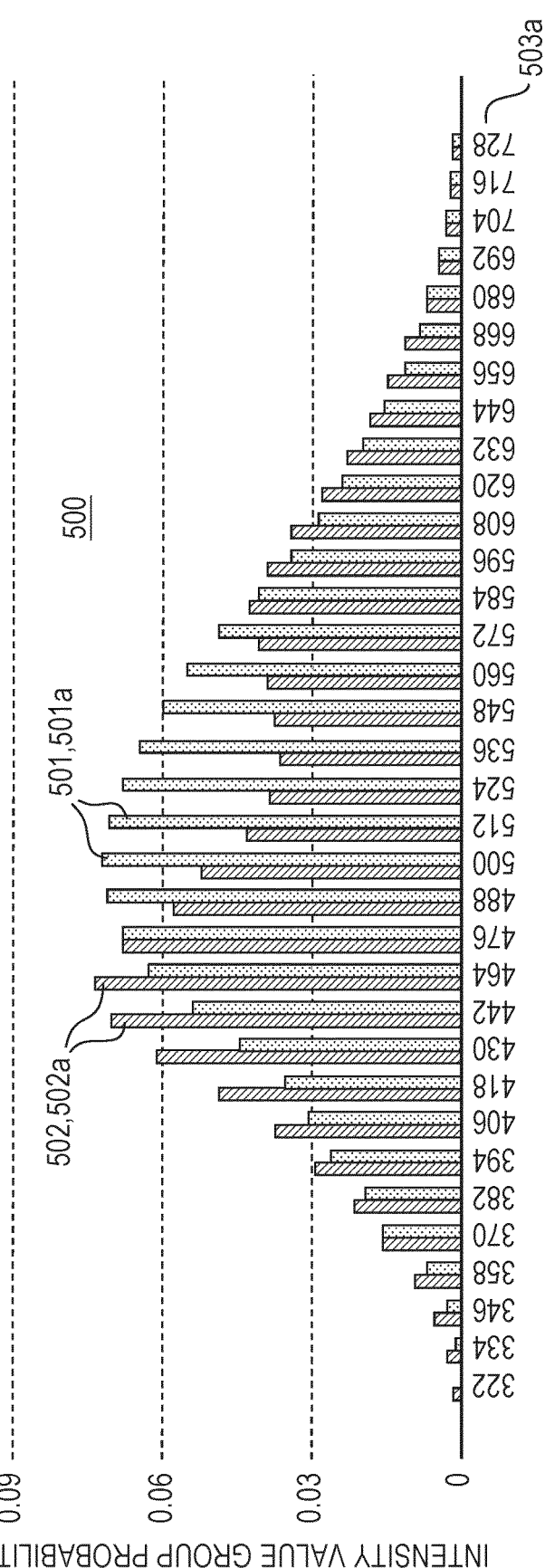
FIG. 11A is a diagram (part 1) illustrating an example of an intensity value group probability distribution.

As a result, as shown in FIG. 11A, the histogram 501a related to the inner region 212 of the component image 401a is calculated. In this manner, the intensity value group probability distribution calculation unit 105 calculates the histogram 501a, which is information related to the distribution of the number of pixels having a predetermined intensity value in the inner region 212.

Subsequently, the intensity value group probability distribution calculation unit 105 also calculates the intensity value group probability of the peripheral region 222 for the component image 401 to be processed.

The intensity value group probability distribution calculation unit 105 counts the number of pixels for each intensity value group in the peripheral region 222 of the component image 401 by the procedure similar to step S141 (Count number of pixels related to each intensity value group in peripheral region: S143 in FIG. 10).

Then, the intensity value group probability distribution calculation unit 105 calculates the probability of the pixel having each intensity value group in the peripheral region 222 of the component image 401 (Calculate intensity value group probability in peripheral region: S144 in FIG. 10). At this time, the intensity value group probability distribution calculation unit 105 divides the number of pixels of each intensity value group by the total number of pixels in the peripheral region 222 (the number of pixels forming the peripheral region 222).

For example, the intensity value group probability distribution calculation unit 105 calculates the intensity value group probability of the peripheral region 222 for the component image 401a shown in FIG. 9B.

Then, the intensity value group probability distribution calculation unit 105 counts the number of pixels for each intensity value group in the peripheral region 222 of the component image 401a by the procedure similar to step S141 (Calculate intensity value group probability in peripheral region: S143 in FIG. 10). The result of step S143 corresponds to the number of pixels having a predetermined intensity value.

Then, the intensity value group probability distribution calculation unit 105 calculates the probability of the pixel having each intensity value group in the peripheral region 222 of the component image 401a (S144 in FIG. 10). At this time, the intensity value group probability distribution calculation unit 105 divides the number of pixels of each intensity value group by the total number of pixels in the peripheral region 222 (the number of pixels forming the peripheral region 222). As a result, a histogram 502a related to the peripheral region 222 of the component image 401a as shown in FIG. 11 is calculated. The histogram 502a corresponds to a second intensity value frequency distribution that is information related to the distribution of the number of pixels having a predetermined intensity value in the peripheral region 222.

The intensity value group probability distribution calculation unit 105 calculates the intensity value group probability distribution 500 for other component images 401b to 401c by the procedure similar to that described above. As a result, histograms 501b, 501c, and 501d related to the inner region 212 are generated for the component images 401b to 401d (see FIGS. 11B to 11D). Further, histograms 502b and 502c related to the peripheral region 222 are generated for the component images 401b and 401c (see FIGS. 11B and 11C).

The histograms 501a to 501d and 502a to 502c as shown in FIGS. 11A to 11D are referred to as the intensity value group probability distribution 500.

Figure 11B:
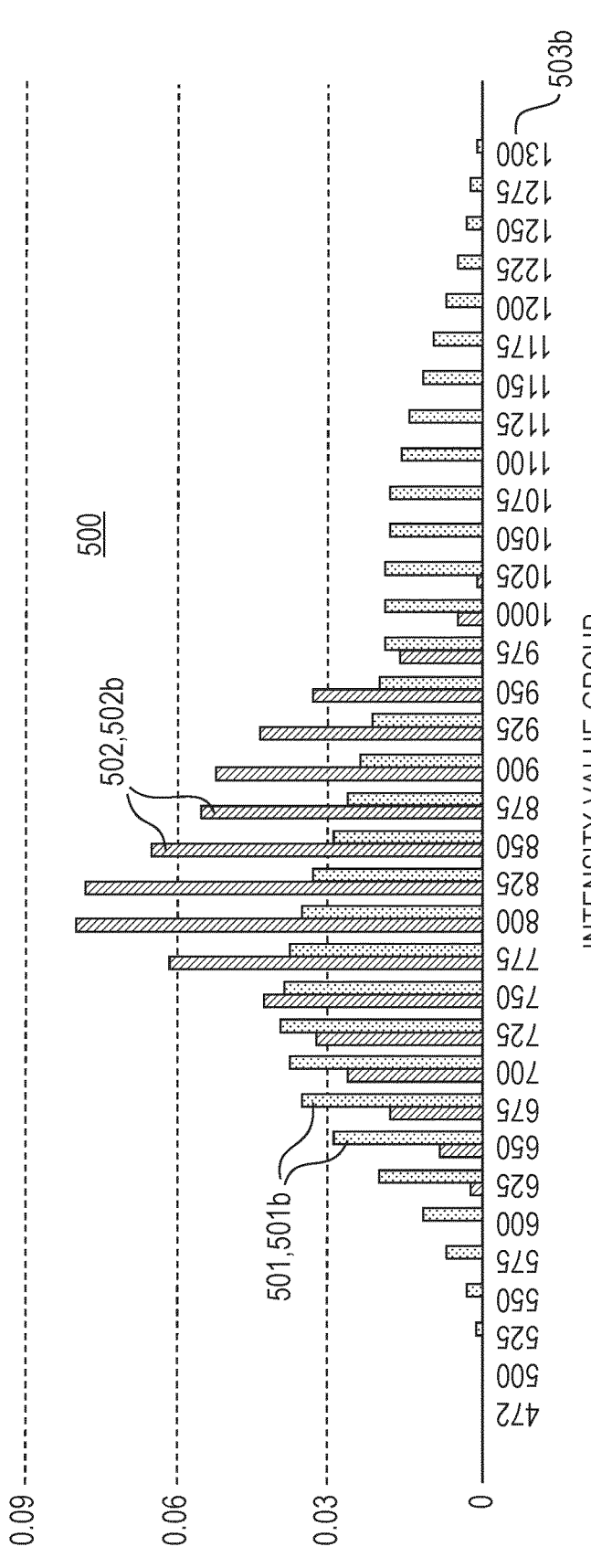
FIG. 11B is a diagram (part 2) illustrating an example of an intensity value group probability distribution.
Figure 11C:
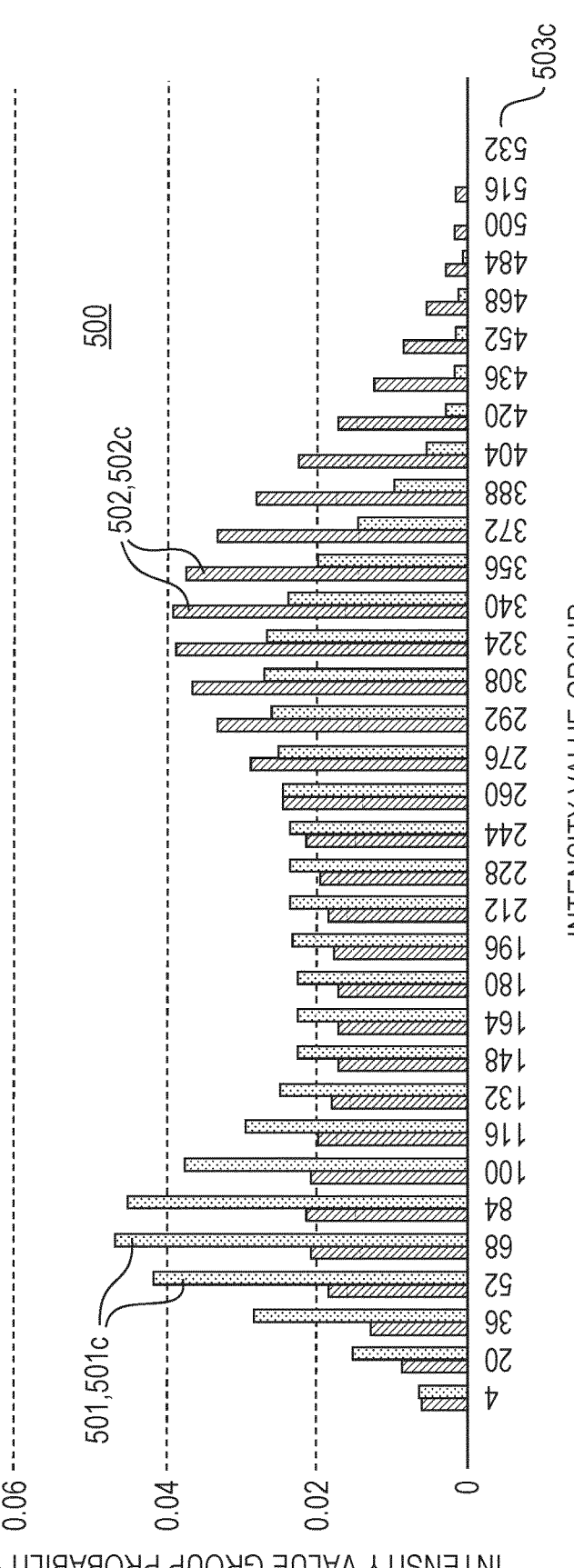
FIG. 11C is a diagram (part 3) illustrating an example of an intensity value group probability distribution.
Figure 11D:
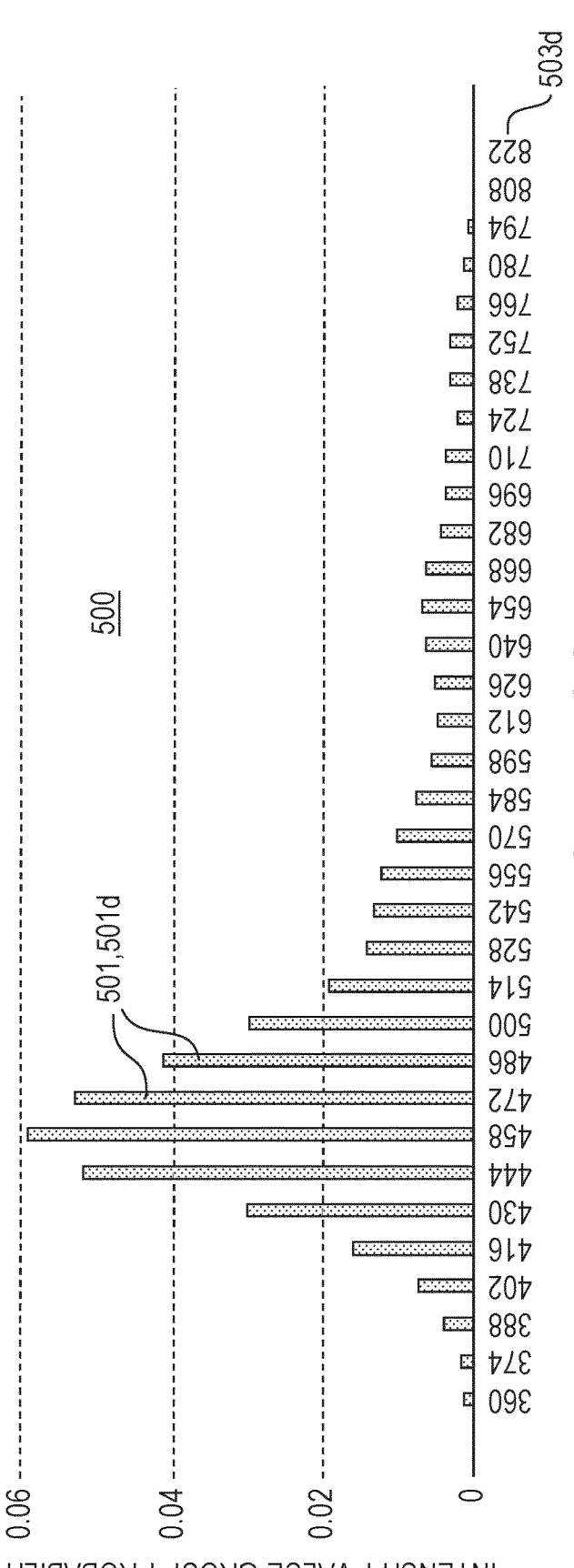
FIG. 11D is a diagram (part 4) illustrating an example of an intensity value group probability distribution.

Note that FIG. 11D shows the intensity value group probability distribution 500 related to the component image 401d. As indicated by reference numeral 241 in FIG. 9E, in the component image 401d, no components (soft tissue) are present in the peripheral region 222. Accordingly, in FIG. 11D, there is no histogram corresponding to the intensity value group probability of the peripheral region 22.

After completion of step S144 in FIG. 10, the computer 100 returns the processing to step S151 in FIG. 4.

(Intensity Value Group Probability Distribution 500)

FIGS. 11A to 11D are diagrams each illustrating an example of the intensity value group probability distribution 500. A description is made with reference to FIGS. 9B to 9E as appropriate.

FIG. 11A shows the intensity value group probability distribution 500 in the component image 401a, and FIG. 11B shows the intensity value group probability distribution 500 in the component image 401b. FIG. 11C shows the intensity value group probability distribution 500 in the component image 401c, and FIG. 11D shows the intensity value group probability distribution 500 in the component image 401d.

In FIGS. 11A to 11D, the horizontal axis represents an intensity value group, and the vertical axis represents an intensity value group probability. Further, in FIGS. 11A to 11D, the histograms 501a to 501d indicate the intensity value group probability in the inner region 212 of each of the component images 401a to 401d. Furthermore, the histograms 502a to 502c indicate the intensity value group probability in the peripheral region 222 of each of the component images 401a to 401c.

The histograms 501a to 501d related to the inner region 212 are collectively referred to as an inner region histogram 501 as appropriate, and the histograms 502a to 502c related to the peripheral region 222 are referred to as a peripheral region histogram 502 as appropriate. That is, the inner region histogram 501 corresponds to the first intensity value frequency distribution that is information related to the distribution of the number of pixels having a predetermined intensity value in the inner region 212. The peripheral region histogram 502 corresponds to the second intensity value frequency distribution that is information related to the distribution of the number of pixels having a predetermined intensity value for the second region. In this manner, the intensity value group probability distribution calculation unit 105 calculates the inner region histogram 501 and the peripheral region histogram 502.

As described above, in the component image 401d shown in FIG. 9E, the components (soft tissue) indicated by reference numeral 241 are not present in the peripheral region 222. Therefore, in the intensity value group probability distribution 500 illustrated in FIG. 11D, there is no histogram of the intensity value group probability in the peripheral region 222. Therefore, since the component image 401d cannot be subjected to the processing of steps S151 to S171 in FIG. 4, steps S151 to S171 are performed only for the component images 401a to 401c.

(Probability Difference Distribution 600)

FIGS. 12A to 12C are diagrams each illustrating the probability difference distribution 600. FIGS. 12A to 12C each illustrate the probability difference distribution 600 which is a result of the processing in step S151 of FIG. 4. A description is made with reference to FIGS. 9B to 9E as appropriate.

In FIGS. 12A to 12C, the horizontal axis represents an intensity value group, and the vertical axis represents the probability difference 601.

FIG. 12A is the probability difference distribution 600 for the component image 401a, FIG. 12B is the probability difference distribution 600 for the component image 401b, and FIG. 12C is the probability difference distribution 600 for the component image 401c. As described above, in the component image 401d, the components are not present in the peripheral region 222, and the intensity value group probability is not present in the peripheral region 222 as illustrated in FIG. 11D. Thus, the processing of step S151 is not performed.

In step S151 of FIG. 4, the peripheral region histogram 502 is subtracted from the inner region histogram 501 of each intensity value group, in the intensity value group probability distribution 500 illustrated in FIGS. 11A to 11C.

For example, the probability difference distribution 600 illustrated in FIG. 11A is calculated by subtracting the histogram 502a from the histogram 501a illustrated in FIG. 12A. Note that a value obtained by subtracting the peripheral region histogram 502 from the inner region histogram 501 of each intensity value group is referred to as the probability difference 601 (difference value), and the distribution of the probability differences 601 related to all the intensity value groups is referred to as the probability difference distribution 600.

Similarly, the probability difference distribution 600 illustrated in FIG. 11B is calculated by subtracting the histogram 502b from the histogram 501b illustrated in FIG. 12B. Further, the probability difference distribution 600 illustrated in FIG. 11C is calculated by calculating a difference value between the histogram 501c and the histogram 502c illustrated in FIG. 12C for each intensity value group (predetermined intensity value).

In the probability difference distribution 600 illustrated in FIGS. 12A to 12C, each bin indicates the probability difference 601 for each intensity value group.

In the probability difference distribution 600 illustrated in FIG. 12C, bins with a positive value are biased toward a place where the intensity value group is low. This indicates that there are many dark pixels in the inner region 212 of the component image 401c in FIG. 12C. Accordingly, in the component image 401c, the dark pixels may correspond to the lesion site.

Note that reference numerals 603 to 607, 607a, 607b, 611, 611a, and 611b shown in FIGS. 12A and 12B will be described later.

(Setting of Detection Range)

Next, step S160 (Set detection range) in FIG. 4 will be described with reference to FIGS. 12A to 12C and 13.

FIG. 13 is a flowchart illustrating a detailed procedure of setting a detection range in step S160 of FIG. 4. The processing illustrated in FIG. 13 corresponds to a detection range setting algorithm.

First, the detection range setting unit 107 detects an intensity interval 607 (Detect intensity interval: S161). The detection range setting unit 107 sets a range in which the probability difference 601 (bin in FIGS. 12A to 12C) has a positive value in the probability difference distribution 600 as the intensity interval 607, and performs the processing of step S162. That is, the detection range setting unit 107 sets an interval in which the probability difference 601 has a positive value in the probability difference distribution 600 as the intensity interval 607 (detection range). In this regard, a range in which the probability difference 601 is positive in the probability difference distribution 600 indicates that the intensity value group corresponding to the range is larger in the inner region 212 than in the peripheral region 222.

Next, the detection range setting unit 107 detects an intensity value group with a local maxima (Detect Intensity value group with local maxima of Probability difference (Imax): S162). The local maxima is a maximum value of the probability difference 601 in a certain intensity interval 607.

As illustrated in FIG. 12B, the intensity interval 607 is not necessarily one for one probability difference distribution 600.

Hereinafter, the intensity value group in which the probability difference 601 is maximum is referred to as a maximum intensity value group 604 (Imax) (see FIGS. 12A to 12C).

Then, the detection range setting unit 107 detects intensity value groups related to a minimum value 605 (see FIG. 12A: Ilow) and a maximum value 606 (see FIG. 12A: Ihigh) in the intensity interval 607 (Detect intensities related to lower end (Ilow) and upper end (Ihigh) of Imax: S163). The minimum value 605 and the maximum value 606 may be detected by linear extrapolation or linear interpolation of the intensity value group, but the extrapolation or interpolation is not limited to "linear".

Subsequently, the detection range setting unit 107 calculates a length (ΔI) of the intensity interval 607 from the minimum value 605 (Ilow) to the maximum value 606

(Ihigh) (Calculate length of intensity interval (ΔI) from lower end (Ilow) to upper end (Ihigh): S164 in FIG. 13).

Depending on the shape of the probability difference distribution 600, a plurality of intensity intervals 607 may be detected. In the example of FIG. 12B, two intensity intervals 607a and 607b are detected.

After step S164, the detection range setting unit 107 determines whether the number of detected intensity intervals 607 is more than 1 (Is more than 1 intensity interval detected?: S165 in FIG. 13).

When the number of detected intensity intervals 607 is 1 (no in S165), the detection range setting unit 107 advances the processing to step S200.

When the number of detected intensity intervals 607 is more than 1 (yes in S165), the detection range setting unit 107 selects the intensity interval 607 with the greatest area of the distribution (a distribution area 611) (see FIG. 12B) formed by bins corresponding to the intensity interval 607 (Select intensity interval with the greatest area under plot: S166 in FIG. 13). Referring to the example illustrated in FIG. 12B, a distribution area 611b corresponding to an intensity interval 607b is greater than a distribution area 611a corresponding to an intensity interval 607a. Therefore, in the example illustrated in FIG. 12B, the detection range setting unit 107 selects the intensity interval 607b in step S166 of FIG. 12. In step S166, when a plurality of intensity intervals 607 is detected, the detection range setting unit 107 selects the intensity interval 607 with a great area of the probability difference distribution 600 in the intensity interval 607.

Next, the detection range setting unit 107 determines a location of the intensity interval 607 (Determine intensity interval location: S200 in FIG. 13). The location is a location in the probability difference distribution 600. Processing of step S200 will be described later.

Then, the detection range setting unit 107 determines whether the intensity interval 607 is near to either a lower edge or an upper edge (Is intensity interval near to intensity edge?: S167). The lower and upper edges refer to a lower end 602 (see FIGS. 12A to 12C: I0) and an upper end 603 (see FIGS. 12A to 12C: Iend) of the probability difference distribution 600, respectively. Specifically, it is determined whether the minimum value 605 of the intensity interval 607 is within a predetermined range from the lower end 602 of the probability difference distribution 600, or whether the maximum value 606 of the intensity interval 607 is within a predetermined range from the upper end 603 of the probability difference distribution 600.

When the intensity interval 607 is not near the edge (no in S167), i.e. when the location of the intensity interval 607 is determined not to be near both the edges, the detection range setting unit 107 returns the processing to step S171 of FIG. 4. As a result, the detection range is not set in the component image 401 in which the intensity interval 607 is determined not to be near the edge.

When the intensity interval 607 is near either of the edges (yes in S167), the detection range setting unit 107 extends the intensity interval 607 to the nearest edge (Extend intensity interval to the nearest intensity edge: S300 in FIG. 13). Processing of step S300 will be described later.

Next, the detection range setting unit 107 adjusts the intensity interval 607 to be a determined detection range (Adjust intensity interval: S400 in FIG. 13). In step S400, the intensity interval 607 is adjusted such that the pixels in the peripheral region 222 are not detected as the lesion site as much as possible. Processing of step S400 will be described later.

After completion of step S400 in FIG. 13, the detection range setting unit 107 sets the adjusted intensity interval 607 as the detection range, and the computer 100 returns the processing to step S171 in FIG. 4.

In the processing illustrated in FIG. 13, the detection range setting unit 107 applies the detection range setting algorithm to each of the plurality of component images 401. Then, the detection range setting unit 107 sets the detection range of the intensity value of the medical image 201 for each of the component images 401 based on the probability difference.

(Determination of Location of Intensity Interval 607)

Next, step S200 (determination of location of the intensity interval 607) in FIG. 13 will be described with reference to FIGS. 12A to 12C and FIG. 14.

Figure 14:
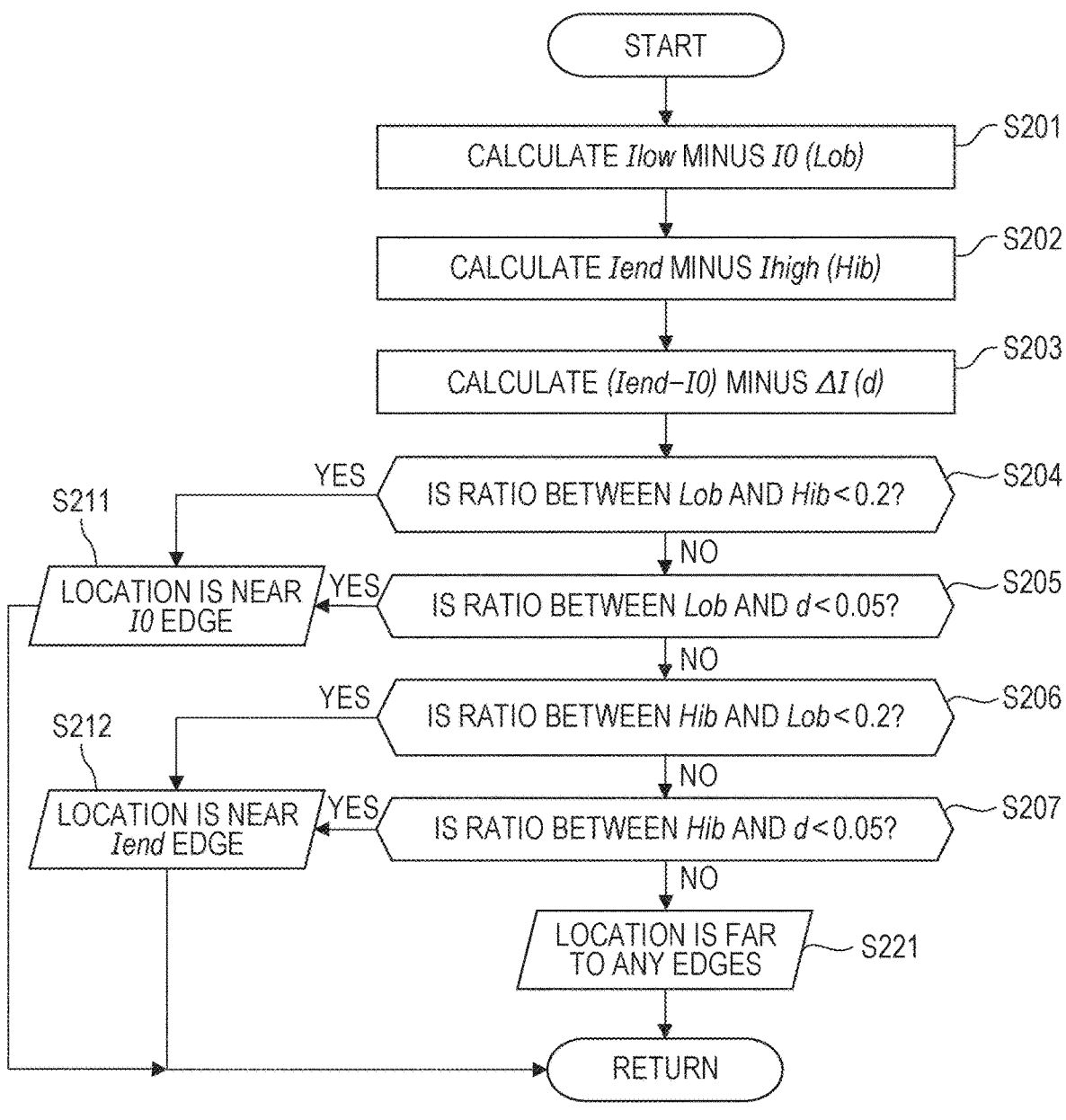
FIG. 14 is a flowchart illustrating a detailed procedure of determining an intensity interval location.

FIG. 14 is a flowchart illustrating a detailed procedure of step S200 (determination of location of the intensity interval 607) in FIG. 13.

First, the detection range setting unit 107 calculates the minimum value 605 minus the lower end 602 (Ilow–I0) in the probability difference distribution 600 (Calculate Ilow minus I0 (Lob): S201 in FIG. 14). A value calculated as a result of step S201 is defined as Lob.

Then, the detection range setting unit 107 calculates the upper end 603 minus the maximum value 606 (Iend–Ihigh) in the probability difference distribution 600 (Calculate Iend minus Ihigh (Hib): S202 in FIG. 14). A value calculated as a result of step S202 is defined as Hib.

Subsequently, the detection range setting unit 107 calculates a value obtained by subtracting the length (ΔI) of the intensity interval 607 from the upper end 603 minus the lower end 602 (Iend–I0) (Calculate (Iend–I0) minus ΔI (d): S203). A value calculated as a result of step S203 is defined as d.

Next, the detection range setting unit 107 determines four conditions in steps S204 to S207.

First, the detection range setting unit 107 determines a first condition ("whether a ratio between Lob and Hib is <0.2" (Is ratio between Lob and Hib<0.2?: S204 in FIG. 14). In the determination, it is determined whether the ratio (the minimum value 605–the lower end 602 (Lob))/(the upper end 603–the maximum value 606 (Hib)) is less than 0.2. Note that the threshold "0.2" in step S204 may be any value as long as it is less than 0.5.

When the first condition is satisfied (yes in S204), the detection range setting unit 107 determines that the intensity interval 607 is near the lower end 602 (I0) (Location is near I0 edge: S211), and returns the processing to step S167 in FIG. 13.

When the first condition is not satisfied (no in S204), the detection range setting unit 107 determines a second condition ("whether the ratio between Lob and d is less than <0.05") (Is ratio between Lob and d<0.05?: S205). In this determination, it is determined whether the ratio (the minimum value 605–the lower end 602 (Lob))/((the upper end 603–the lower end 602)–the length of the intensity interval 607 ((Iend–I0)–ΔI=d)) is less than 0.05. Note that the threshold in step S205 is not limited to 0.05.

When the second condition is satisfied (yes in S205), the detection range setting unit 107 determines that the intensity interval 607 is near the lower end 602 (I0) (Location is near I0 edge: S211), and returns the processing to step S167 in FIG. 13.

When the second condition is not satisfied (no in S205), the detection range setting unit 107 determines a third condition ("whether the ratio between Hib and Lob is <0.2") (Is ratio between Hib and Lob<0.2?: S206). In step S206, it is determined whether the ratio (the upper end 603–the maximum value 606 (Hib))/(the minimum value 605–the lower end 602 (Lob)) is less than 0.2. Note that the threshold "0.2" in S206 may be any value as long as it is less than 0.5.

When the third condition is satisfied (yes in S206), the detection range setting unit 107 determines that the intensity interval 607 is near the upper end 603 (Iend) (Location is near Iend edge: S212 in FIG. 14), and returns the processing to step S167 in step S13.

When the third condition is not satisfied (no in S206), the detection range setting unit 107 determines a fourth condition ("whether the ratio between Hib and d is <0.05") (Is ratio between Hib and d<0.05?: S207). In step S206, it is determined whether the ratio (the upper end 603–the maximum value 606 (Hib))/((the upper end 603–the lower end 602)–the length of the intensity interval 607 ((Iend–I0)–ΔI=d)) is less than 0.05. Note that the threshold in S207 is not limited to 0.05.

When the fourth condition is satisfied (yes in S207), the detection range setting unit 107 determines that the intensity interval 607 is near the upper end 603 (Iend) (Location is near Iend edge: S212), and returns the processing to step S167 in FIG. 13.

When the fourth condition is not satisfied (no in S207), the detection range setting unit 107 determines that the intensity interval 607 is not near both the upper end 603 and the lower end 602 as illustrated in FIG. 12A (Location is far to any edges: S221). Thereafter, the detection range setting unit 107 returns the processing to step S167 in FIG. 13.

As described above, the first condition and the second condition are conditions for determining whether the intensity interval 607 is near the lower end 602 (I0). The third condition and the fourth condition are conditions for determining whether the intensity interval 607 is near the upper end 603 (Iend).

For example, it is determined that the intensity interval 607 illustrated in FIG. 12A is separated from both the lower end 602 (I0) and the upper end 603 (Iend) (S221 in FIG. 14). Meanwhile, it is determined that the intensity interval 607b (intensity value group "975" to "1300") illustrated in FIG. 12B is near the upper end 603 (Iend) (S212 in FIG. 14). Then, it is determined that the intensity interval 607 (intensity value group "4" to "260") illustrated in FIG. 12C is present near the lower end 602 (I0) (S211 in FIG. 4).

As illustrated in FIG. 12A, the fact that the intensity interval 607 is present in the middle of the probability difference distribution 600, i.e. that the intensity interval 607 is far from both the upper end 603 and the lower end 602 indicates the following. In this case, as illustrated in the intensity value group probability distribution 500 of FIG. 11A, the intensity interval 607 is neither a bright region nor a dark region, and thus cannot be characterized as a lesion site. That is, the lesion site is generally detected as a place having a large intensity value (bright) or a place having a small intensity value (dark). Accordingly, as illustrated in FIG. 12A, the component image 401 having the intensity interval 607 in the middle of the probability difference distribution 600 is excluded from the detection range setting target.

(Extension of Intensity Interval)

Figure 15:
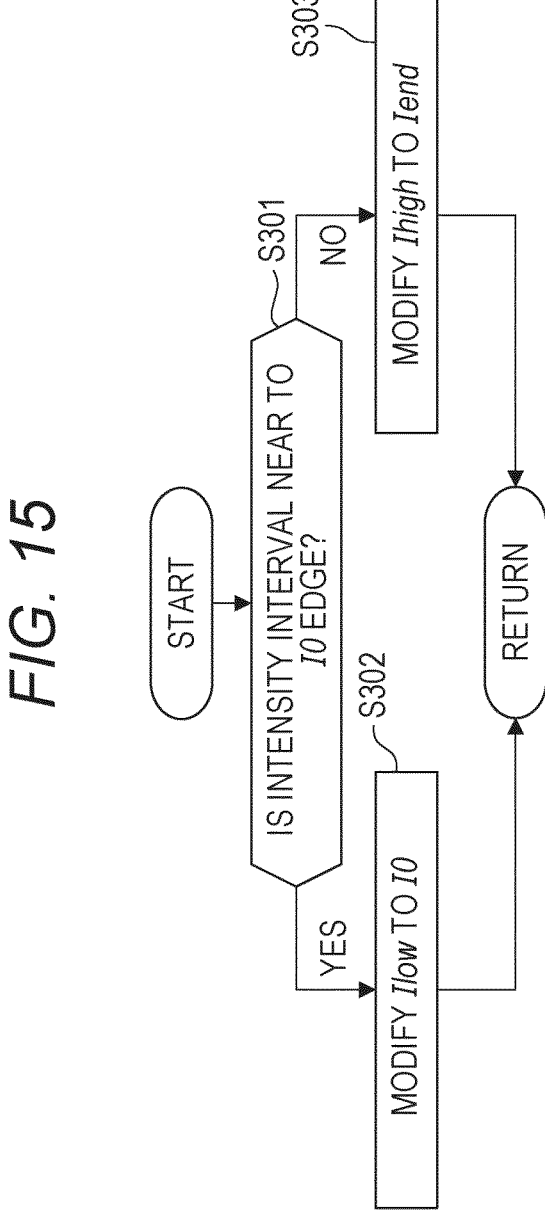
FIG. 15 is a flowchart illustrating a detailed procedure of extending an intensity interval.

FIG. 15 is a flowchart illustrating a detailed procedure of extending the intensity interval 607 in step S300 of FIG. 13. A description is made with reference to FIGS. 12A to 12C as appropriate.

First, the detection range setting unit 107 determines whether it is determined that, in the processing illustrated in FIG. 13, the intensity interval 607 to be processed is near to the lower end 602 (I0) or the upper end 603 (Iend) (S167 in FIG. 13).

When the intensity interval 607 to be processed is far from both the lower end 602 (I0) and the upper end 603 (Iend) (no in S167 in FIG. 13), the detection range setting unit 107 returns the processing to step S171 in FIG. 4 and performs processing on the next component image 401. As described above, in the intensity interval 607 far from both the lower end 602 (I0) and the maximum value (Iend), subsequent steps are not performed.

The detection range setting unit 107 determines whether the location of the intensity interval 607 is near to the lower end 602 (I0) (Is intensity interval near to I0 edge?: S301 in FIG. 15).

When the intensity interval 607 is near to the lower end 602 (I0) (yes in S301), the detection range setting unit 107 modifies the minimum value 605 (Ilow) to the lower end 602 (I0) (Modify Ilow to I0: S302 in FIG. 15). That is, the detection range setting unit 107 extends the intensity interval 607 to the lower end 602 (I0). As described above, when the intensity interval 607 is near to the lower end 602 of the probability difference distribution 600, the detection range setting unit 107 extends the minimum value 605 of the intensity interval 607 to the lower end 602.

When the intensity interval 607 is near to the upper end 603 (Iend) (no in S301), the detection range setting unit 107 modifies the maximum value 606 (Ihigh) to the upper end 603 (Iend) (Modify Ihigh to Iend: S303 in FIG. 15). That is, the detection range setting unit 107 extends the intensity interval 607 to the upper end 603 (Iend). Thus, after completion of steps S302 and S303 in FIG. 15, the detection range setting unit 107 returns the processing to step S400 in FIG. 13. When the intensity interval 607 is near to the upper end 603 in the probability difference distribution 600, the detection range setting unit 107 extends the maximum value 606 of the intensity interval 607 to the upper end 603.

In general, the intensity interval 607 detected in steps S162 to S164 often does not include the lower end 602 or the upper end 603. As described above, the lesion site is indicated by a bright pixel or a dark pixel. Therefore, when a bright pixel is indicated as the lesion site, all the pixels having an intensity equal to or greater than the maximum value 606 (Ihigh) are indicated as lesion sites by step S303. Similarly, when a dark pixel is indicated as the lesion site, all of the pixels having an intensity equal to or less than the minimum value of 605 (Ilow) are indicated as lesion sites by step S302.

(Intensity Interval Adjustment Processing)

Figure 16:
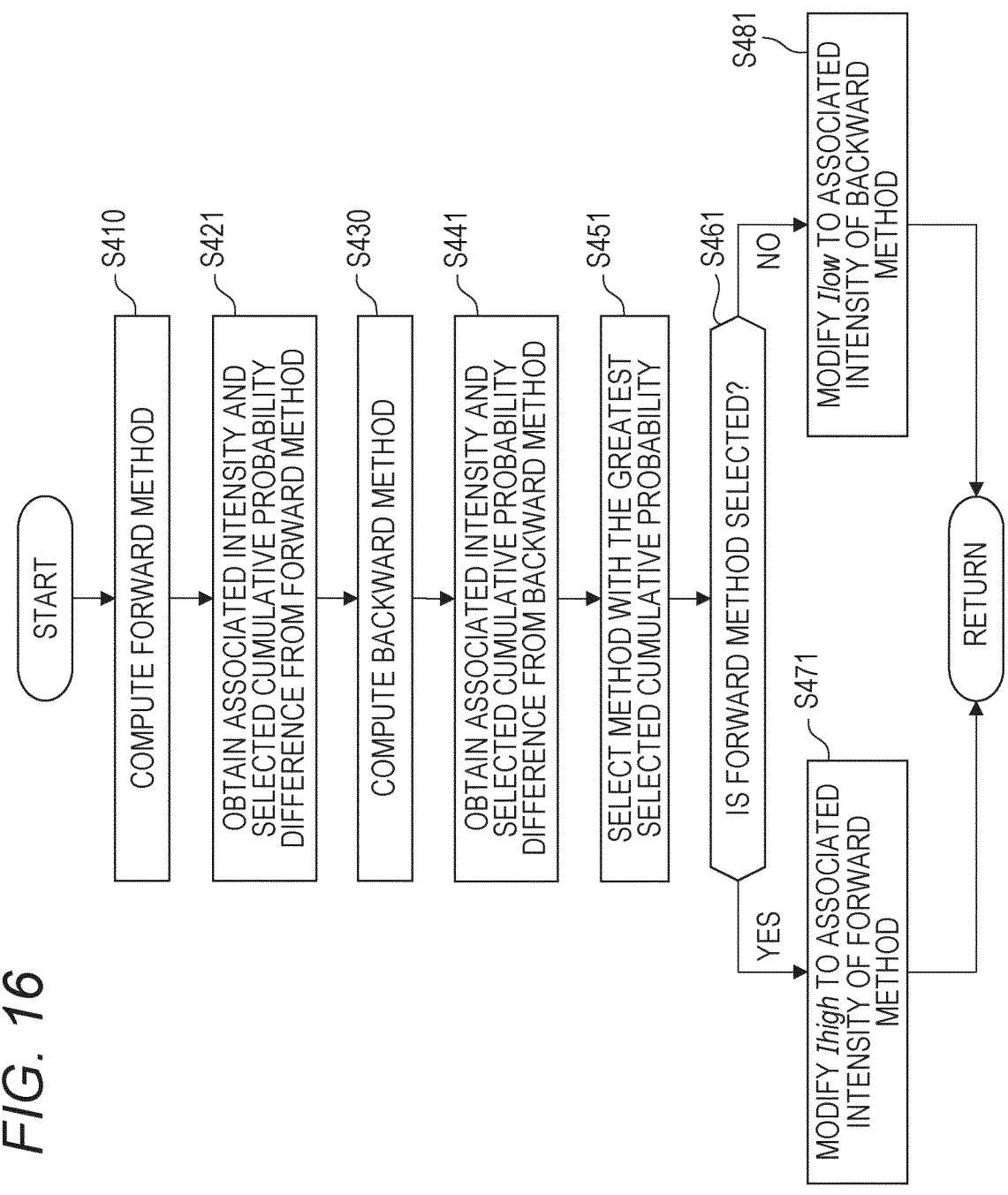
FIG. 16 is a flowchart illustrating a detailed procedure of adjusting an intensity interval.

FIG. 16 is a flowchart illustrating a detailed procedure of the intensity interval adjustment in step S400 of FIG. 13. A description is made with reference to FIGS. 18, 20, 21, and 22 as appropriate.

In order to describe the procedure illustrated in FIG. 16, a description is made with reference to the intensity interval 607b (intensity value group "975" to "1300") in the component image 401b shown in FIG. 12B.

First, the detection range setting unit 107 executes a first method: the forward method (Compute forward method: S410 in FIG. 16). Processing of step S410 will be described later. An associated intensity 704, i.e. a selected intensity value, and a selected cumulative probability 705, i.e. a first selected cumulative intensity value probability, are computed in step S410. The associated intensity 704 and the selected cumulative probability 705 will be described later.

Figure 18:
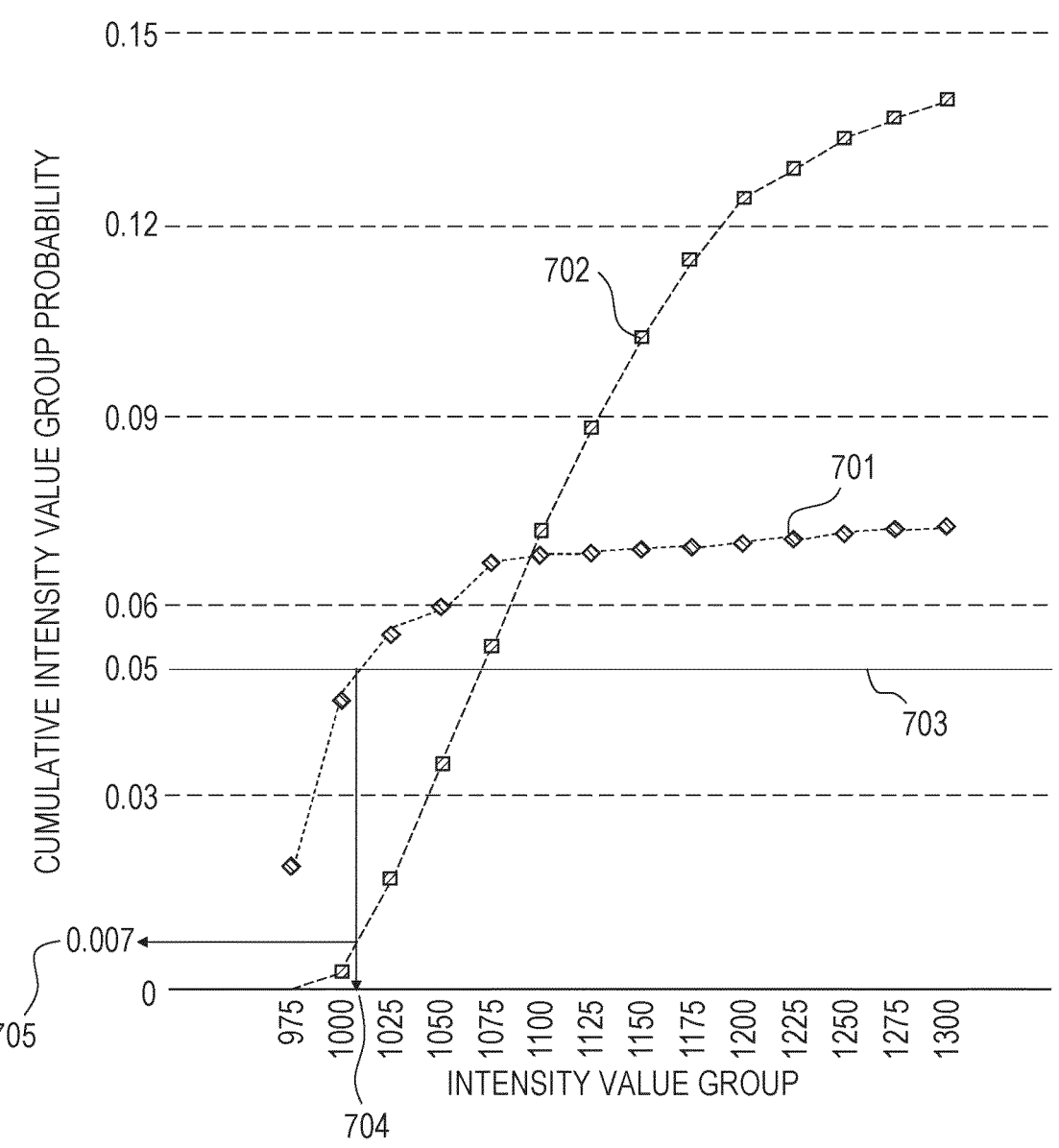
FIG. 18 is a diagram (part 1) illustrating an example of a cumulative intensity value group probability in a peripheral region and a cumulative probability difference obtained using the forward method.

Subsequently, the detection range setting unit 107 acquires the associated intensity 704 and the selected cumulative probability 705 corresponding to the associated intensity 704 from the result of the forward method in step S410 (Obtain associated intensity and selected cumulative probability difference from forward method: S421 in FIG. 16). The definitions of the associated intensity 704 and the selected cumulative probability 705 will be described later with reference to FIG. 18. In the example of FIG. 18, the associated intensity 704 and the selected cumulative probability 705 are "1010" and "0.007", respectively.

Next, the detection range setting unit 107 executes a second method: the backward method (Compute backward method: S430 in FIG. 16). Processing of step S430 will be described later. An associated intensity 804, i.e. a selected intensity value, and a selected cumulative probability 805, i.e. a second selected cumulative intensity value probability, are computed in step S430. The associated intensity 804 and the selected cumulative probability 805 will be described later.

The detection range setting unit 107 acquires the associated intensity 804 and the selected cumulative probability 805 by the backward method (Obtain associated intensity and selected cumulative probability difference from backward method: S441 in FIG. 16). In the example illustrated in FIG. 20, the associated intensity 804 and the selected cumulative probability 805 are "990" and "0.141", respectively.

Thereafter, the detection range setting unit 107 selects which one of the forward method and the backward method has the greatest selected cumulative probability 705, 805 (Select method with the greatest selected cumulative probability: S451 in FIG. 16). In other words, the detection range setting unit 107 makes a magnitude relation comparison between the value of the selected cumulative probability 705 in FIG. 18 and the value of the selected cumulative probability 805 in FIG. 20.

Then, the detection range setting unit 107 determines whether the forward method is selected (Is forward method selected?: S461).

When the forward method is selected (yes in S461 in FIG. 16), the detection range setting unit 107 modifies the maximum value 606 (Ihigh) to the associated intensity 704 (see FIG. 18) acquired by the forward method (Modify Ihigh to associated intensity of forward method: S471 in FIG. 16).

When the backward method is selected (no in S461 in FIG. 16), the detection range setting unit 107 modifies the minimum value 605 (Ilow) to the associated intensity 804 acquired by the backward method (FIG. 18) (Modify Ilow to associated intensity of backward method: S481 in FIG. 16). The detection range setting unit 107 outputs the intensity interval 607 modified in step S471 or step S481 as a detection range.

Figure 20:
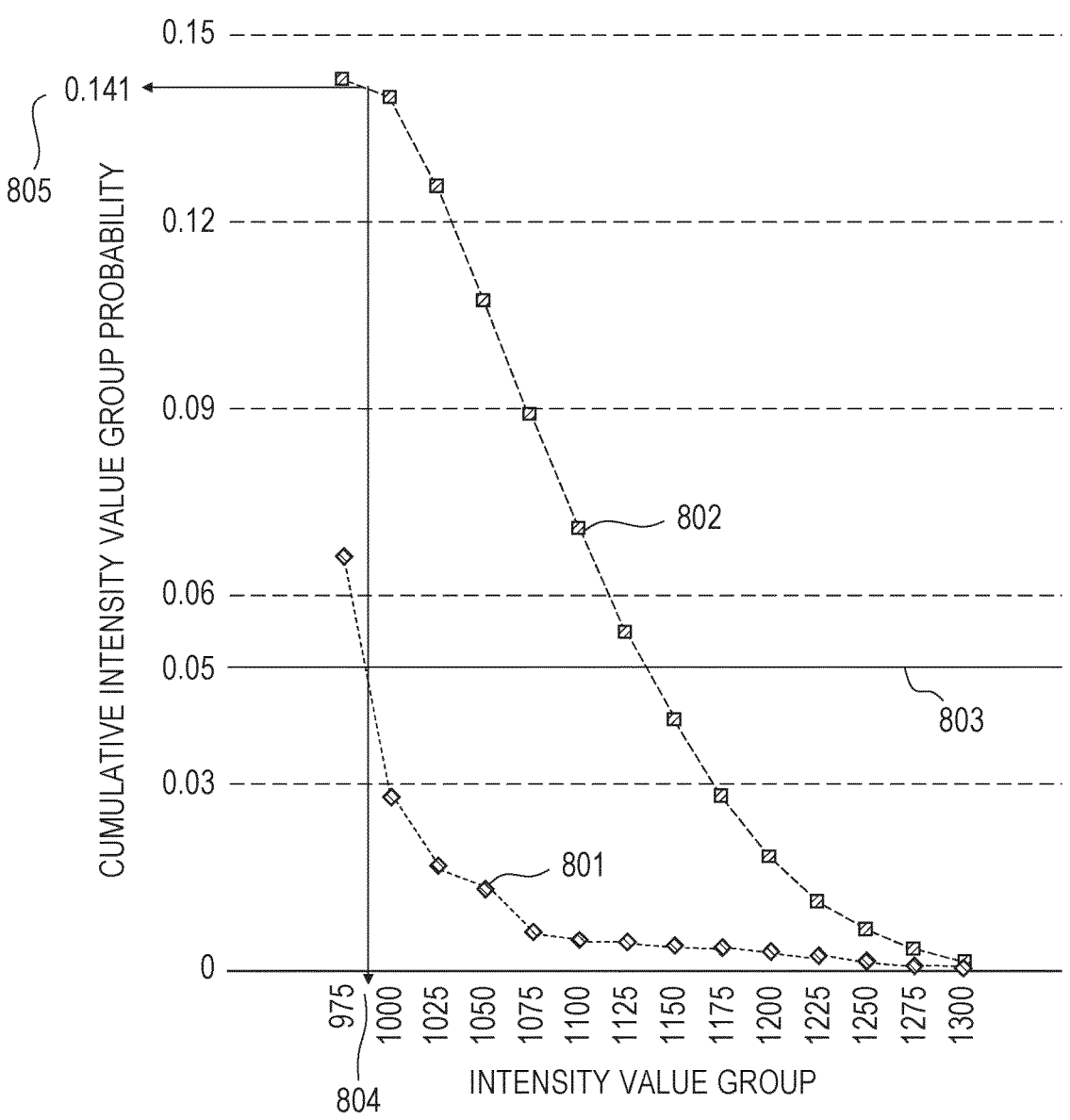
FIG. 20 is a diagram (part 1) illustrating an example of a cumulative intensity value group probability in a peripheral region and a cumulative probability difference obtained using the backward method.

According to the examples illustrated in FIGS. 18 and 20, the selected cumulative probability 705 of the forward method is "0.007" (see FIG. 18), and the selected cumulative probability 805 of the backward method is "0.141" (see FIG. 20). Thus, the backward method is selected in step S461 of FIG. 16. The intensity value group "975" that is the minimum value 605 (Ilow) in FIG. 12B is modified to "990" (associated intensity 804 acquired by the backward method (see FIG. 20)).

Then, in step S481, the detection range setting unit 107 sets the intensity interval 607 (i.e. the detection range) in the intensity value groups "990" to "1300". After completion of steps S471 and S481 in FIG. 16, the detection range setting unit 107 returns the processing to step S171 in FIG. 4.

(Forward Method)

Figure 17:
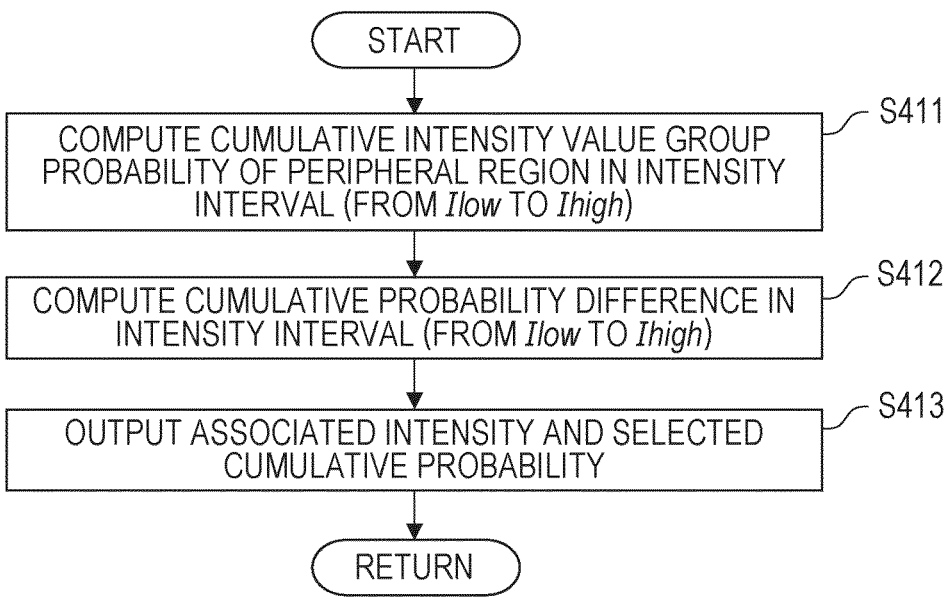
FIG. 17 is a flowchart illustrating a detailed procedure of a forward method.

FIG. 17 is a flowchart illustrating a detailed procedure of the forward method in step S410 of FIG. 16. A description is made with reference to FIGS. 11B and 12B as appropriate.

First, the detection range setting unit 107 computes a cumulative intensity value group probability 701 (first cumulative intensity value probability: see FIG. 18) of the peripheral region 222 in the intensity interval 607 from the set minimum value 605 (Ilow) to the maximum value 606 (Ihigh) (Compute cumulative intensity value group probability of peripheral region in intensity interval (from Ilow to Ihigh): S411 in FIG. 17). The set minimum value 605 (Ilow) may be modified to the lower end 602 (I0) if the intensity interval 607 is near to the edge of I0 (S302 of FIG. 15), the set maximum value 606 (Ihigh) may be modified to the upper end 603 (Iend) if the intensity interval 607 is near to the edge of Iend (S303 of FIG. 15). In step S411, the intensity value group probability of the peripheral region histogram 502 (FIGS. 11A to 11C) is accumulated from the minimum value 605 (Ilow) to the maximum value 606 (Ihigh). The set minimum value 605 (Ilow) and the maximum value 606 (Ihigh) are the minimum value 605 and the maximum value 606 set in the processing illustrated in FIG. 15, respectively.

In the example illustrated in FIG. 11B, the peripheral region histogram 502 (histogram 502b) is accumulated for each bin from the intensity value group "975" having the minimum value 605 (Ilow) to the intensity value group "1300" having the maximum value 606 (Ihigh) in the intensity interval 607.

As described above, in step S411, the detection range setting unit 107 computes the cumulative intensity value group probability 701 by accumulating the peripheral region histogram 502 from the side of the minimum value 605 of the intensity interval 607 to the side of the maximum value 606 of the intensity interval 607, for the peripheral region 222.

The description returns to FIG. 17.

After step S411, the detection range setting unit 107 computes a cumulative probability difference 702 (a second cumulative intensity value probability: see FIG. 18) from the side of the minimum value 605 (Ilow) to the maximum value 606 (Ihigh) (Compute cumulative probability difference in intensity interval (from Ilow to Ihigh): S412 in FIG. 17). For example, in the example of the probability difference distribution 600 illustrated in FIG. 12B, the probability difference 601 for the component image 401b is accumulated for each bin from the minimum value 605 (Ilow: the intensity value group "975") to the maximum value 606 (Ihigh: the intensity value group "1300") in the intensity interval 607b.

In step S412, the detection range setting unit 107 computes the cumulative probability difference 702 by accumulating the probability difference 601 from the side of the minimum value 605 of the intensity interval 607 to the side of the maximum value 606 of the intensity interval 607.

The description returns to FIG. 17.

The detection range setting unit 107 sets a predetermined threshold "0.05" (reference numeral 703 in FIG. 18) for minimizing the number of pixels detected in the peripheral region 222.

After that, the detection range setting unit 107 selects the associated intensity 704 as the intensity value based on a predetermined threshold (reference numeral 703 in FIG. 18) and the cumulative intensity value group probability 701. Then, the detection range setting unit 107 determines the cumulative intensity value group probability 701 corresponding to the selected associated intensity 704 as the selected cumulative probability 705: a first selected cumulative intensity value probability. Thereafter, the detection range setting unit 107 outputs the associated intensity 704 and the selected cumulative probability 705 (Output associated intensity and selected cumulative probability: S413 in FIG. 17).

After completion of step S413 in FIG. 17, the detection range setting unit 107 returns the processing to step S421 in FIG. 16.

(Result of Forward Method)

FIG. 18 is a diagram illustrating an example of the cumulative intensity value group probability 701 of the peripheral region 222 (see FIG. 9C) and the cumulative probability difference 702 obtained using the forward method. The results illustrated in FIG. 18 are based on the results illustrated in FIGS. 11B and 12B.

In the graph illustrated in FIG. 18, the horizontal axis represents the intensity value group. Further, the vertical axis represents the cumulative intensity value group probability 701 (Cumulative intensity value group probability). Note that a threshold (reference numeral 703) of "0.05" (reference numeral 703) is set to the cumulative intensity value group probability 701 of the peripheral region 222. The associated intensity 704 (e.g. the intensity value group "1010"), as the intensity value group related to the forward method, is defined by an intensity value group (horizontal axis) where the threshold value "0.05" (reference numeral 703) intersects the cumulative intensity value group probability 701 of the peripheral region 222. That is, the detection range setting unit 107 selects the associated intensity 704 based on a predetermined threshold (reference numeral 703 in FIG. 18) and the cumulative intensity value group probability 701.

Linear extrapolation or linear interpolation can be considered for the calculation of the intensity value group where the threshold "0.05" (reference numeral 703) intersects the cumulative intensity value group probability 701 of the peripheral region 222, but the extrapolation or interpolation is not limited to "linear". Further, the selected cumulative probability 705 corresponding to the associated intensity 704 of the forward method is defined by the value of the cumulative probability difference 702 corresponding to the associated intensity 704 ("0.007" in the example of FIG. 18). In this manner, the detection range setting unit 107 determines the cumulative probability difference 702 corresponding to the selected associated intensity 704 as the selected cumulative probability 705.

The detection range setting unit 107 outputs the selected cumulative probability 705 and the associated intensity 704.

(Backward Method)

Figure 19:
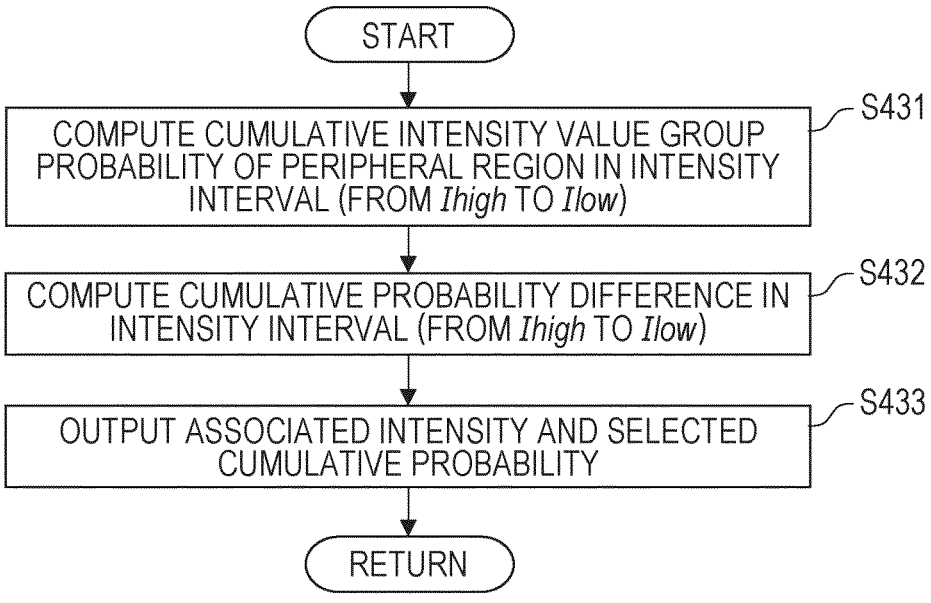
FIG. 19 is a flowchart illustrating a detailed procedure of a backward method.

FIG. 19 is a flowchart illustrating a detailed procedure of the backward method in step S430 of FIG. 16. A description is made with reference to FIGS. 11B, 12B, and 20 as appropriate.

First, the detection range setting unit 107 computes a cumulative intensity value group probability 801 (a third cumulative intensity value probability: see FIG. 20) of the peripheral region 222 in the intensity interval 607 from the maximum value 606 (Ihigh) to the minimum value 605 (Ilow) (Compute cumulative intensity value group probability of peripheral region in intensity interval (from Ihigh to Ilow): S431 in FIG. 19). In step S431, the intensity value group probability of the peripheral region histogram 502 (FIGS. 11A to 11C) is accumulated from the maximum value 606 (Ihigh) to the minimum value 605 (Ilow). The set maximum value 606 (Ihigh) and the minimum value 605 (Ilow) are the maximum value 606 and the minimum value 605 set in the processing illustrated in FIG. 15, respectively.

The set maximum value 606 (Ihigh) may be modified to the upper end 603 (Iend) if the intensity interval 607 is near to the edge of Iend (S303 of FIG. 15), the set minimum value 605 (Ilow) may be modified to the lower end 602 (I0) if the intensity interval 607 is near to the edge of I0 (S302 of FIG. 15).

In the example illustrated in FIG. 11B, the peripheral region histogram 502 (histogram 502b) is accumulated for each bin from the side of the maximum value 606 (Ihigh: the intensity value group "1300") to the intensity value group of the minimum value 605 (Ilow: the intensity value group "975") in the intensity interval 607.

As described above, in step S431, the detection range setting unit 107 computes the cumulative intensity value group probability 801 by accumulating the peripheral region histogram 502 from the side of the maximum value 606 of the intensity interval 607 to the side of the minimum value 605 of the intensity interval 607, for the peripheral region 222.

Next, the detection range setting unit 107 computes a cumulative probability difference 802 (a fourth cumulative intensity value probability: see FIG. 20) from the side of the maximum value 606 (Ihigh) to the side of the minimum value 605 (Ilow) (Compute cumulative probability difference in intensity interval (from Ihigh to Ilow): S432 in FIG. 19). For example, in the example probability difference distribution 600 illustrated in FIG. 12B, the probability difference 601 for the component image 401b is accumulated for each bin from the maximum value 606 (Ihigh: the intensity value group "1300") to the minimum value 605 (Ilow: the intensity value group "975") in the intensity interval 607b.

In step S432, the detection range setting unit 107 computes the cumulative probability difference 802 by accumulating the probability difference 601 from the side of the maximum value 606 of the intensity interval 607 to the side of the minimum value 605 of the intensity interval 607.

Then, regarding the cumulative intensity value group probability 801 (see FIG. 20) of the peripheral region 222, the detection range setting unit 107 sets a predetermined threshold for minimizing the portion of the peripheral region 222 in the intensity interval 607 to "0.05" (reference numeral 803).

Subsequently, the detection range setting unit 107 selects the associated intensity 804 (intensity value) based on the predetermined threshold (reference numeral 803 in FIG. 20) and the cumulative intensity value group probability 801. Thereafter, the detection range setting unit 107 determines the cumulative probability difference 802 corresponding to the selected associated intensity 804 as the selected cumulative probability 805, i.e. the second selected cumulative intensity value probability. Then, the detection range setting unit 107 outputs the associated intensity 804 and the selected cumulative probability 805 (Output associated intensity and selected cumulative probability: S433 in FIG. 19).

After completion of step S433 in FIG. 19, the detection range setting unit 107 returns the processing to step S441 in FIG. 16.

(Result of Backward Method)

FIG. 20 is a diagram illustrating an example of the cumulative intensity value group probability 801 of the peripheral region 222 and the cumulative probability difference 802 obtained using the backward method.

In the graph illustrated in FIG. 20, the horizontal axis represents the intensity value group. Further, the vertical axis represents the cumulative intensity value group probability 801 (Cumulative intensity value group probability).

The threshold "0.05" (reference numeral 803) is set to the cumulative intensity value group probability 801 of the peripheral region 222. Furthermore, the associated intensity 804 ("990" in the example of FIG. 20) of the backward method is defined by an intensity value group (horizontal axis) where the limit of "0.05" (reference numeral 803) intersects the cumulative intensity value group probability 801 of the peripheral region 222. That is, the detection range setting unit 107 selects the associated intensity 804 based on the predetermined threshold (reference numeral 803 in FIG. 20) and the cumulative intensity value group probability 801.

Linear extrapolation or linear interpolation is considered for the calculation of the intensity value group (horizontal axis) where the threshold "0.05" (reference numeral 803) intersects the cumulative intensity value group probability 801 of the peripheral region 222, but the extrapolation or interpolation is not limited to "linear". Further, the selected cumulative probability 805 (e.g. "0.141") corresponding to the associated intensity 804 of the backward method is defined by the value of the cumulative probability difference 802 corresponding to the associated intensity 804. In this manner, the detection range setting unit 107 determines the cumulative probability difference 802 corresponding to the selected associated intensity 804 as the selected cumulative probability 805.

The detection range setting unit 107 outputs the selected cumulative probability 805 and the associated intensity 804.

As shown in step S471 of FIG. 16, when the forward method is selected in step S461, the detection range setting unit 107 modifies the maximum value 606 (Ihigh) to the associated intensity 704 (see FIG. 18) of the forward method (S471 of FIG. 16). That is, when the selected cumulative probability 705 is greater than the selected cumulative probability 805, the detection range setting unit 107 determines the maximum value 606 of the intensity interval 607 as the associated intensity 704 selected by the forward method.

In the intensity value group greater than the selected cumulative probability 705 in FIG. 18, the pixel having the corresponding intensity value is also detected in the peripheral region 222 at the probability of "0.05". Performing the processing illustrated in step S471 enables the probability of being erroneously detected as a lesion site in the peripheral region 222 to be reduced to less than "0.05".

As shown in step S481 of FIG. 16, when the backward method is selected in step S461, the detection range setting unit 107 modifies the minimum value 605 (Ilow) to the associated intensity 804 (see FIG. 18) of the backward method (S481 of FIG. 16). That is, when the selected cumulative probability 805 is greater than the selected cumulative probability 705, the detection range setting unit 107 determines the minimum value 605 of the intensity interval 607 as the associated intensity 804 selected by the backward method.

In the intensity value group greater than the selected cumulative probability 805 in FIG. 20, the pixel having the corresponding intensity value is also detected in the peripheral region 222 at the probability of "0.05". Performing the processing illustrated in step S481 enables the probability of being erroneously detected as a lesion site in the peripheral region 222 to be reduced to less than "0.05". However, as described above, in the examples illustrated in FIGS. 18 and 20, the backward method is selected.

In this manner, the detection range setting unit 107 modifies the detection range in step S471 or step S481 in FIG. 16.

In a case where the intensity value group probability or the probability difference based on the component image 401b illustrated in FIG. 11B or 12B is used, the backward method is selected in step S461. Therefore, the detection range setting unit 107 modifies the minimum value 605 (Ilow) to the associated intensity 804 (see FIG. 18) of the backward method (S481 in FIG. 16).

(Result of Forward Method and Result of Backward Method (Part 2))

Figure 21:
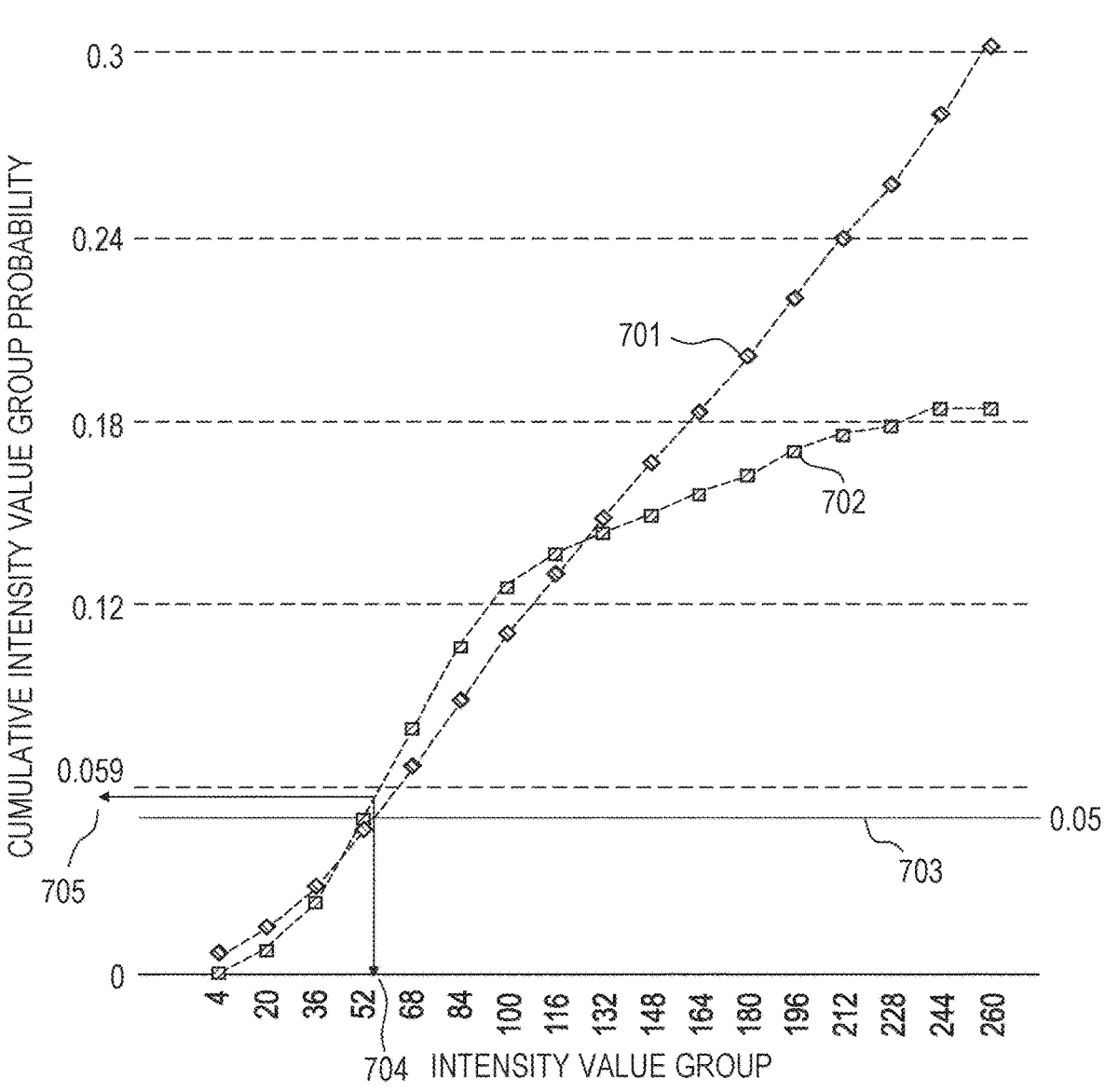
FIG. 21 is a diagram (part 2) illustrating an example of a cumulative intensity value group probability in a peripheral region and a cumulative probability difference obtained using the forward method.
Figure 22:
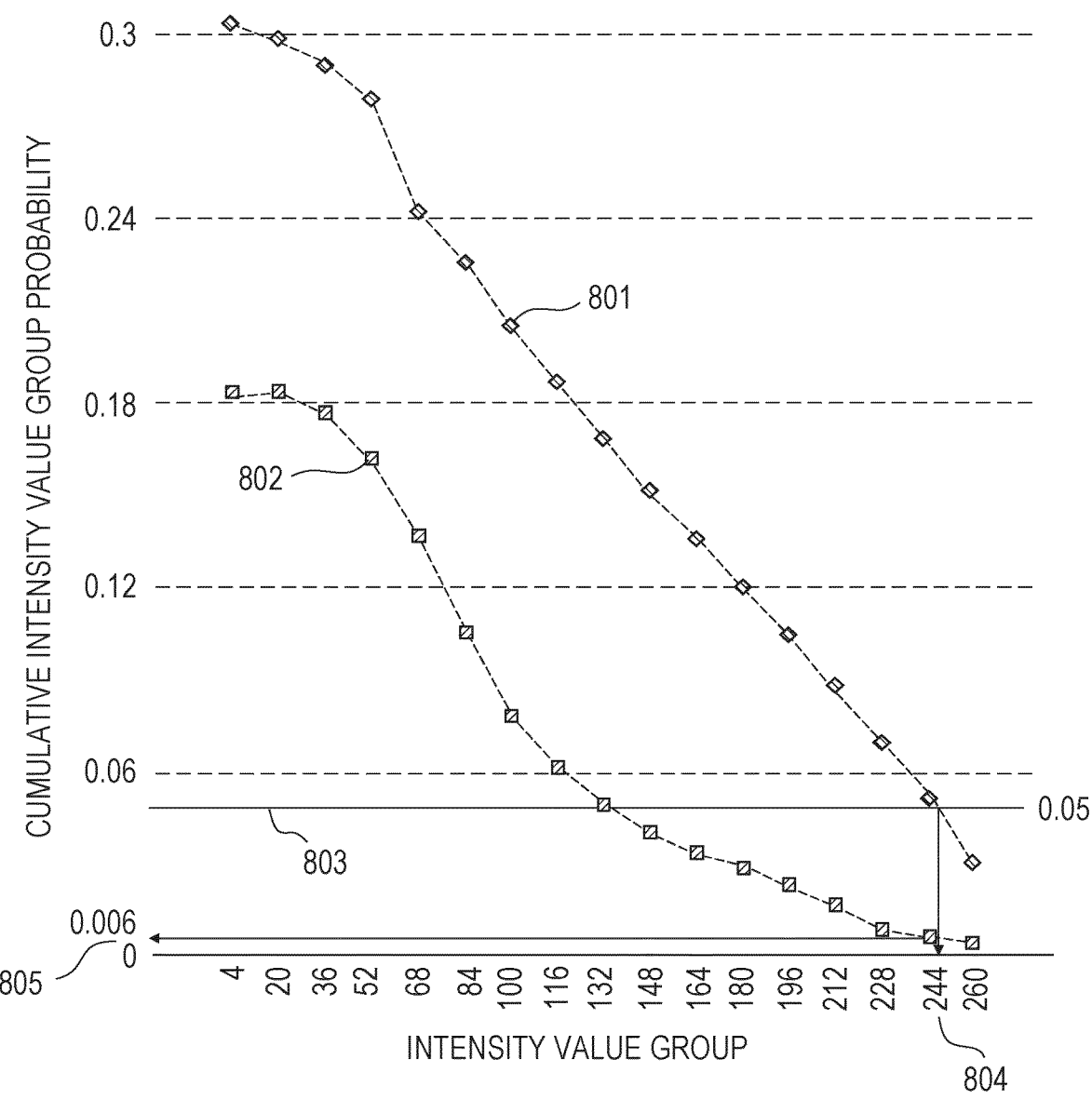
FIG. 22 is a diagram (part 2) illustrating an example of a cumulative intensity value group probability in a peripheral region and a cumulative probability difference obtained using the backward method.

FIGS. 21 and 22 are diagrams illustrating results of the forward method and the backward method performed using the intensity interval 607 of FIG. 11C, for the intensity value group probability distribution 500 (see FIG. 12C) and the probability difference distribution 600 (see FIG. 12C) in the component image 401c shown in FIG. 9D. FIG. 21 shows the result of the forward method, and FIG. 22 shows the result of the backward method. In other words, the results illustrated in FIGS. 21 and 22 show an example in which the forward method and the backward method are used for the intensity interval 607 (intensity value group "4" to "260") in FIG. 12C. In FIGS. 21 and 22, the horizontal axis and the vertical axis are similar to those in FIGS. 18 and 20.

FIG. 21 illustrates the cumulative intensity value group probability 701 of the peripheral region 222 and the cumulative probability difference 702 (see FIG. 9D). Further, the threshold "0.05" (reference numeral 703 in FIG. 21) is set to the cumulative intensity value group probability 701 of the peripheral region 222 to minimize the number of pixels erroneously detected in the peripheral region 222. Then, the associated intensity 704 of the forward method is defined by an intensity value (horizontal axis) where the threshold "0.05" (reference numeral 703) intersects the cumulative intensity value group probability 701 of the peripheral region 222.

Linear extrapolation or linear interpolation can be considered for the calculation method of the intensity value where the threshold "0.05" (reference numeral 703) intersects the cumulative intensity value group probability 701 of the peripheral region 222, but the extrapolation or interpolation is not limited to the "linear" method. Further, the selected cumulative probability 705 corresponding to the associated intensity 704 of the forward method is defined by the value of the cumulative probability difference 702 corresponding to the associated intensity 704.

Further, FIG. 22 illustrates the cumulative intensity value group probability 801 of the peripheral region 222 and the cumulative probability difference 802. Furthermore, the threshold "0.05" (reference numeral 803) is set to the cumulative intensity value group probability 801 of the peripheral region 222 to minimize the number of pixels erroneously detected in the peripheral region 222. Then, the associated intensity 804 of the backward method is defined by an intensity value group (horizontal axis) where the threshold "0.05" (reference numeral 803) intersects the cumulative intensity value group probability 801 of the peripheral region 222.

Linear extrapolation or linear interpolation can be considered for the calculation method of the intensity value where the threshold "0.05" (reference numeral 803) intersects the cumulative intensity value group probability 801 of the peripheral region 222, but the extrapolation or interpolation is not limited to the "linear" method. Further, the selected cumulative probability 805 corresponding to the associated intensity 804 of the backward method is defined by the value of the cumulative probability difference 802 corresponding to the associated intensity 804.

According to the examples of FIGS. 21 and 22, the selected cumulative probability 705 of the forward method is 0.059, and the selected cumulative probability 805 of the backward method is 0.006. Therefore, in step S461 in FIG. 16, the forward method is selected.

In addition, in step S471 of FIG. 16, the value of the intensity value group "260" at the maximum value 606 (Ihigh) in the intensity interval 607 of FIG. 12C is modified to "55", which is a value of the associated intensity 704 of the forward method in FIG. 21. Therefore, the intensity interval 607 (detection range) of the component image 401c is set to a range of "4" to "55". As described above, the use of the selected cumulative probabilities 705 and 805 makes it possible to reduce erroneous detection of a lesion site outside the inner region 212 (peripheral region 222).

(Mask)

Figure 23:
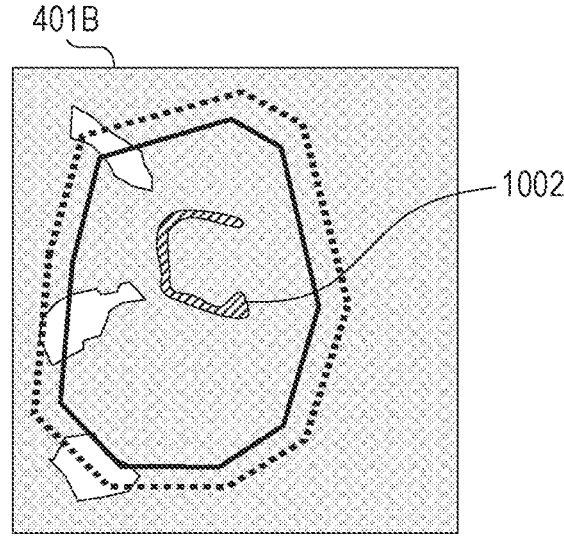
FIG. 23 is a view showing a mask generated by the lesion site highlighting processing according to a set detection range.

FIG. 23 is a view showing a mask generated by the lesion site highlighting processing according to a set detection range. In FIG. 23, the mask is generated as a result of the processing performed in step S171 of FIG. 4.

FIG. 23 shows a component image 401B in which a mask is applied to the component image 401b. In the component image 401B, pixels having an intensity value corresponding to the intensity interval 607 (detection range) set in step S160 in FIG. 4 are highlighted as a mask region 1002 (selected pixels) which is a predetermined region. Specifically, the mask setting unit 108 selects pixels to be highlighted for each of the plurality of component images 401 based on the intensity interval 607 (i.e. the detection range) set for each of the component images 401. Then, the mask setting unit 108 highlights the selected pixels as the mask region 1002.

(Synthesis of Mask)

Next, mask synthesis processing performed in step S181 of FIG. 4 will be described with reference to FIGS. 24A to 24E.

Figure 24A:
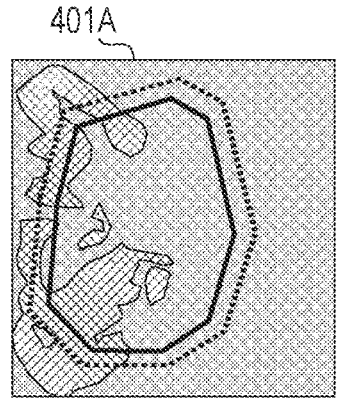
FIG. 24A is a view (part 1) showing a masked component image.
Figure 24B:
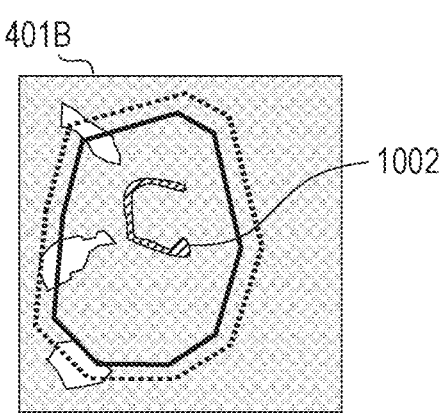
FIG. 24B is a view (part 2) showing a masked component image.
Figure 24C:
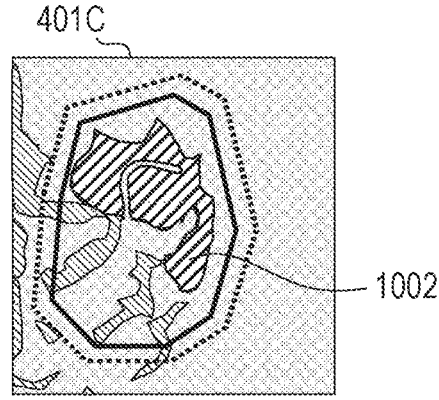
FIG. 24C is a view (part 3) showing a masked component image.
Figure 24D:
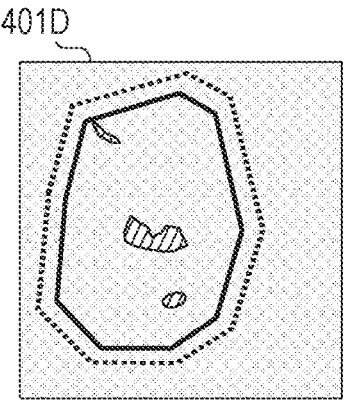
FIG. 24D is a view (part 4) showing a masked component image.
Figure 24E:
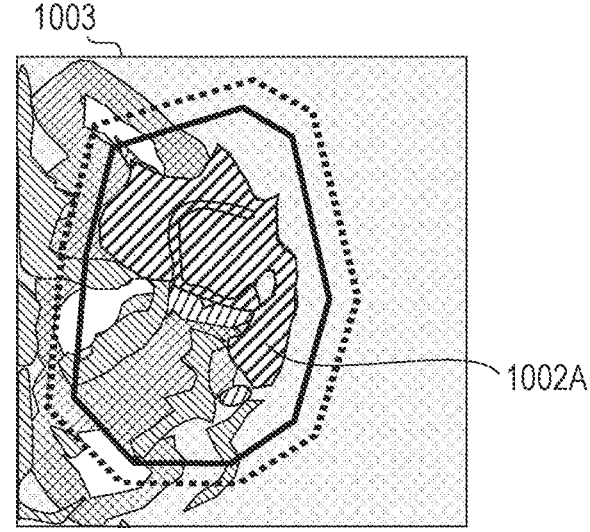
FIG. 24E is a view showing an example of a mask image.

FIG. 24A is a third image for the component image 401a shown in FIG. 9B, and is a view showing a masked component image 401A. FIG. 24B is a third image for the component image 401b shown in FIG. 9C, and is a view showing a masked component image 401B. FIG. 24C is a third image for the component image 401c shown in FIG. 9D, and is a view showing a masked component image 401C. Further, FIG. 24D is a third image for the component image 401d shown in FIG. 9E, and is a view showing a masked component image 401D. The mask image 1003 shown in FIG. 24E is obtained by synthesizing the component images 401A to 401D shown in FIGS. 24A to 24D.

The mask setting unit 108 highlights pixels according to the detection range set by the detection range setting unit 107, thereby generating component images 401A to 401D shown in FIGS. 24A to 24D. Further, in the component images 401B and 401C, the mask region 1002 in which pixels having intensity values corresponding to the detection range are highlighted is displayed. However, in the component image 401d shown in FIG. 9E, the components (soft tissue) are not present in the peripheral region 222 in the original component image 401d as described in FIG. 11D. Accordingly, there is no peripheral region histogram 502 based on the component image 401d, and thus the detection range setting processing is not performed. Therefore, in the component image 401D shown in FIG. 24D, the mask region 1002 as shown in FIGS. 24B and 24C is not displayed. That is, the component image 401D shown in FIG. 24D is an image similar to the component image 401d shown in FIG. 9E.

In the component image 401*a* shown in FIG. 9B, as shown in FIG. 12A, the intensity interval 607 is located at the center of the probability difference distribution 600. That is, the intensity interval 607 is far from both the lower end 602 (I0) and the upper end 603 (Iend). Thus, the detection range setting processing is not performed (S160 in FIG. 4 is interrupted, and S171 is not performed). As a result, the mask as shown in FIGS. 24B and 24C is not set in the component image 401A shown in FIG. 24A. Accordingly, the component image 401A shown in FIG. 24A is an image similar to the component image 401*a* shown in FIG. 9B.

A detection range is set for each of the component image 401*b* shown in FIG. 9C and the component image 401*c* shown in FIG. 9D. Thus, as shown in FIGS. 24B and 24C, pixels having intensity values corresponding to the respective detection ranges are highlighted, as a result of which the mask setting unit 108 displays the mask region 1002.

As shown in FIGS. 24A and 24D, masks are not generated for all the component images 401. As in the example shown in FIGS. 24B and 24C, the mask region 1002 indicating highlighted lesion site is generated only for the component image 401*b* and the component image 401*c*.

Then, in step S181 in FIG. 4, the mask compilation unit 109 synthesizes the generated component images 401A to 401D, and thus all the masks are synthesized. As a result, as shown in FIG. 24E, the mask image 1003 (a fourth image) having a single mask region 1002A is generated. The pixel highlighted by the mask region 1002A corresponds to the mask region 1002 in FIG. 24B and the mask region 1002 in FIG. 24C. In this manner, the mask compilation unit 109 synthesizes the pixel selected by the mask setting unit 108 to form the mask image 1003.

(Display Screen 1100)

Figure 25:
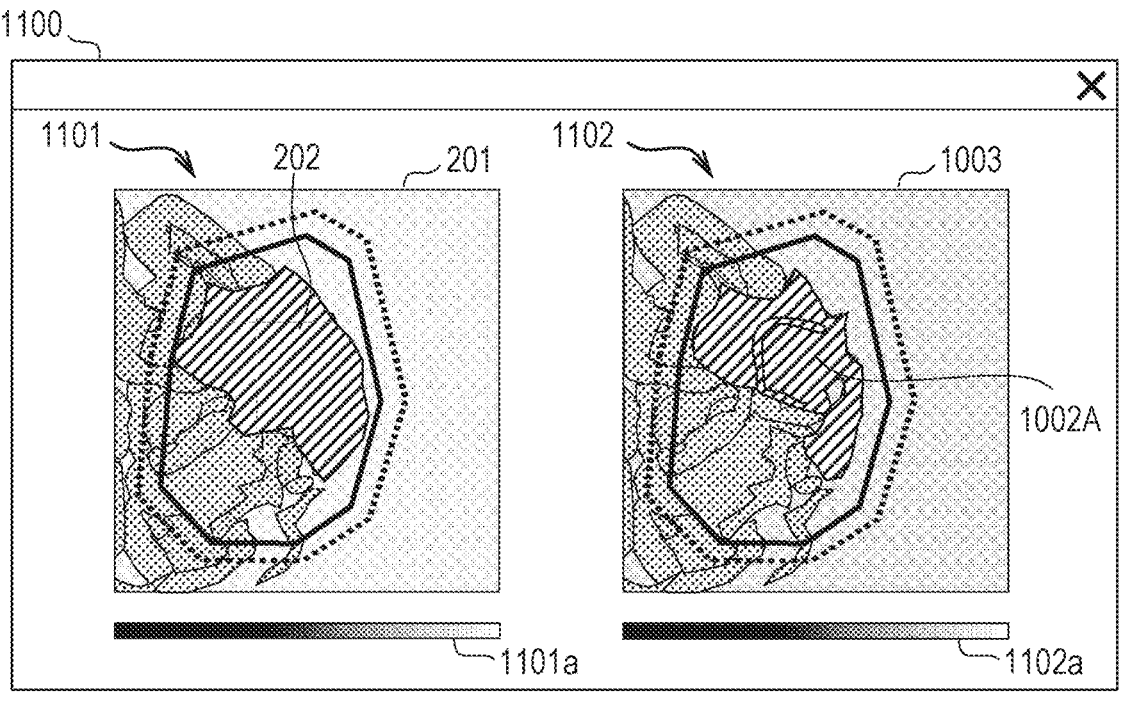
FIG. 25 is a view showing an example of a display screen displayed on a display device.

FIG. 25 is a view showing an example of a display screen 1100 displayed on the display device 132. Note that FIG. 25 is displayed as a result of the display processing in step S191 of FIG. 4.

As shown in FIG. 25, the display screen 1100 includes screens 1101 and 1102. The screen 1101 displays the medical image 201 which is read in step S101 in FIG. 4 and displayed in step S102 in FIG. 4. Incidentally, the medical image 201 displayed on the screen 1101 is similar to the medical image 201 shown in FIG. 7. In the screen 1101, a place suspected to be a lesion site is highlighted as the lesion region 202. The place highlighted in the lesion region 202 is a place determined to be a lesion site by a doctor as described above. The place with the suspected lesion site is the place determined by the doctor as described above. A color bar 1101*a* corresponds to the intensity value on the screen 1101.

In addition, the mask image 1003, which is a result of performing the image processing (lesion site highlighting processing) illustrated in FIG. 4, is displayed on the screen 1102. A color bar 1102*a* corresponds to the luminance value on the screen 1102.

As shown in FIG. 25, the screen 1101 displaying the medical image 201 before the lesion site highlighting processing is performed and the screen 1102 displaying the mask image 1003 after the lesion site highlighting processing is performed are displayed on the display screen 1100. In the mask image 1003 displayed on the screen 1102, the synthesized mask is highlighted as the mask region 1002A. As described above, the display processing unit 110 displays (outputs), on the display device 132, the component image 401 in which the pixel (the mask region 1002) selected by the mask setting unit 108 is highlighted, as the mask image 1003.

In the lesion region 202 of the screen 1101, the place determined as the lesion site by the doctor is roughly shown. On the other hand, on the screen 1102, the display accuracy of the lesion site (mask region 1002A) is improved by the lesion site highlighting processing. Further, according to the lesion site highlighting processing of the present embodiment, not only bright pixels but also dark pixels can be detected as lesion sites.

Providing the display as shown in FIG. 25 enables the user to make a comparison between the medical image 201 and the mask image 1003 before and after performing the lesion site highlighting processing. After checking the result displayed on the screen 1102, and the user saves the mask image 1003 displayed on the screen 1102 together with a disease name and the like as lesion data.

According to the first embodiment, the lesion site can be drawn more accurately by setting a determination criterion (detection range) of the lesion site for each component.

In addition, in a case where only one threshold is set, when there is a pixel exceeding the threshold outside the inner region 212 (peripheral region 222), there is a possibility that the pixel is also highlighted as the lesion site in the peripheral region 222. Furthermore, in a case where one threshold is set, either a bright pixel or a dark pixel in the medical image 201 is highlighted as the lesion site. However, in practice, the lesion site in the medical image 201 often includes bright and dark pixels depending on the component.

In the first embodiment, in response to the input of the user, the region (the inner region 212) corresponding to the lesion site in the medical image 201 is designated. Then, the pixel intensity detection range is determined using the appearance frequencies of the intensities of all the pixels inside the inner region 212 and the appearance frequencies of the intensities of the pixels in the peripheral region 222 (e.g. 20% outside the inner region 212). At this time, in the first embodiment, the component image is decomposed into component images 401 for each component, and the detection range is set for each of the component images 401. This makes it possible to highlight the lesion site with high accuracy. Further, synthesis of the component images 401A to 401D in which the lesion site is highlighted (masked) makes it possible to display the mask image 1003 in which the lesion site is displayed with high accuracy. As described above, according to the first embodiment, the region of interest in the image can be highlighted with high accuracy.

As described in the image above, in the first embodiment, to simplify these specialized viewpoints and complicated operations, the region range (the inner region 212) corresponding to the lesion site diagnosed by the user is received as an input. Then, the computer 100 compares the intensity distribution of the selected range with the intensity distribution of the peripheral region 222 and highlights the lesion site within the designated range.

In addition, the forward method and the backward method illustrated in FIGS. 16 to 22 are performed. As a result, the method is selected in which the selected cumulative probabilities 705 and 805 calculated are greater than those by the other method. Then, the detection range is modified with the associated intensities 704 and 804 calculated by the selected forward method or backward method. With this configuration, it is possible to reduce erroneous detection of the lesion site in the peripheral region 222.

Second Embodiment

Next, the second embodiment of the present invention will be described with reference to FIGS. 26 to 31E.

Although processing of a 2D image (e.g. a 2D image spreading across an x-axis-y-axis plane) has been described in the first embodiment, the processing can be extended to three dimensions using the same inner line 211 (see FIG. 7). That is, the inner line 211 is set for a plurality of 2D medical images 201 adjacent in a z direction in FIG. 27A, and the mask image 1003 is generated based on the set inner line 211. Then, the mask images 1003 are stacked, and thus a 3D image 250 (fifth image) is constructed.

(Computer 100A)

Figure 26:
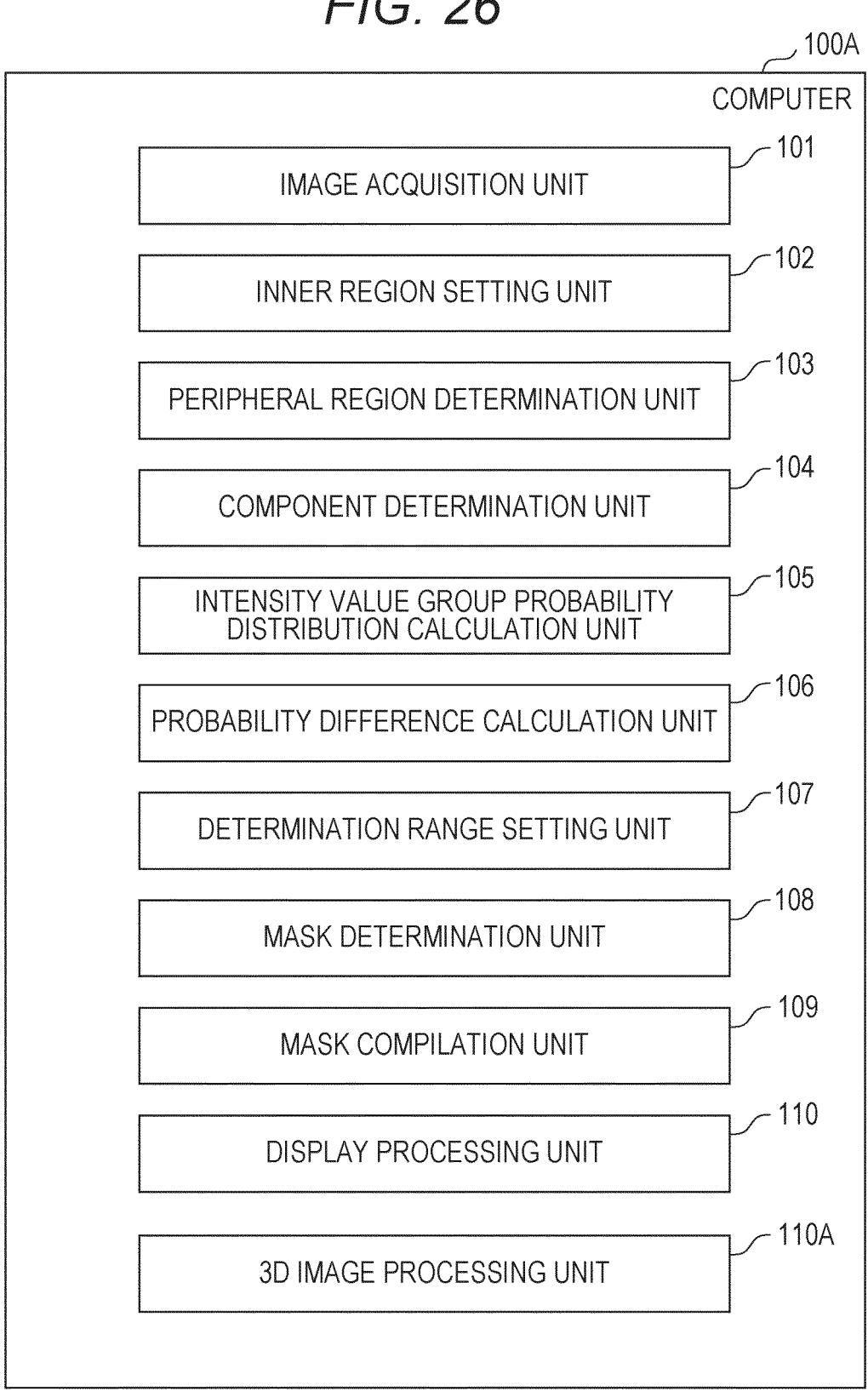
FIG. 26 is a diagram illustrating a configuration of a computer according to a second embodiment.

FIG. 26 is a diagram illustrating a configuration of a computer 100A according to the second embodiment. In FIG. 26, the same elements as those in FIG. 2 are denoted by the same reference numerals, and redundant description is omitted.

In the second embodiment, a plurality of mask images 1003 is present.

Figure 27A:
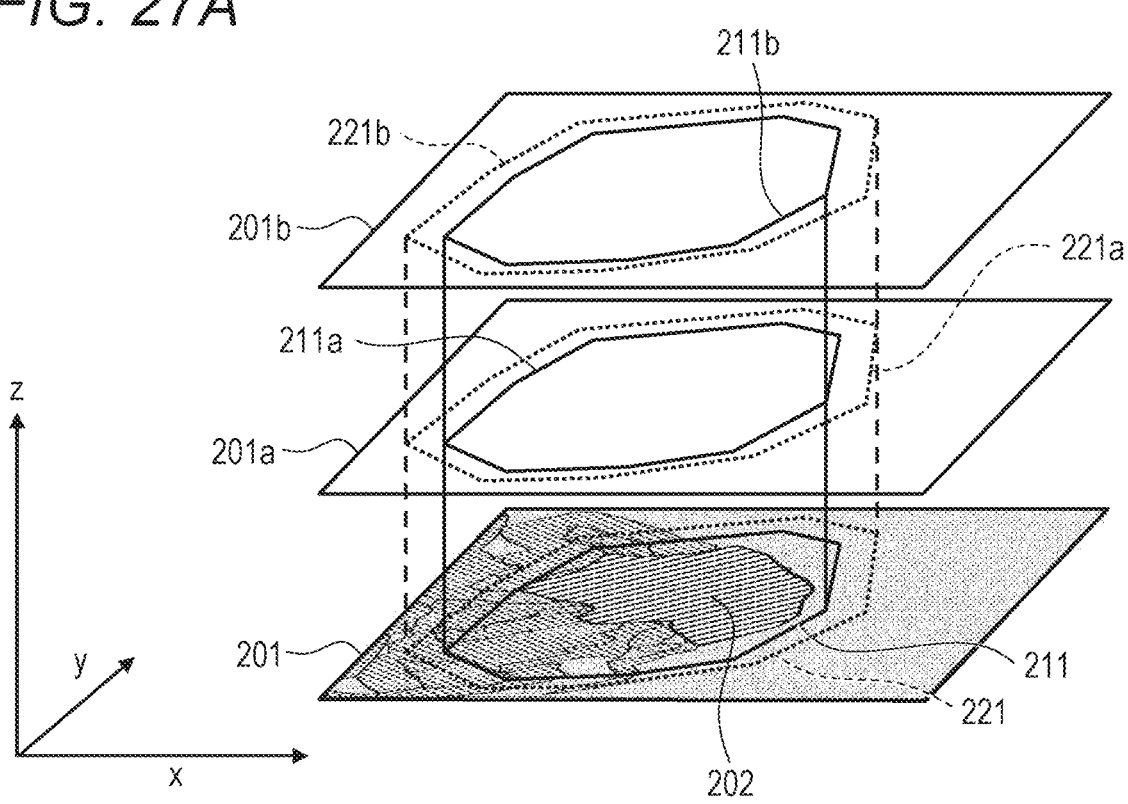
FIG. 27A is a view (part 1) showing an outline of a method of generating a 3D image.
Figure 27B:
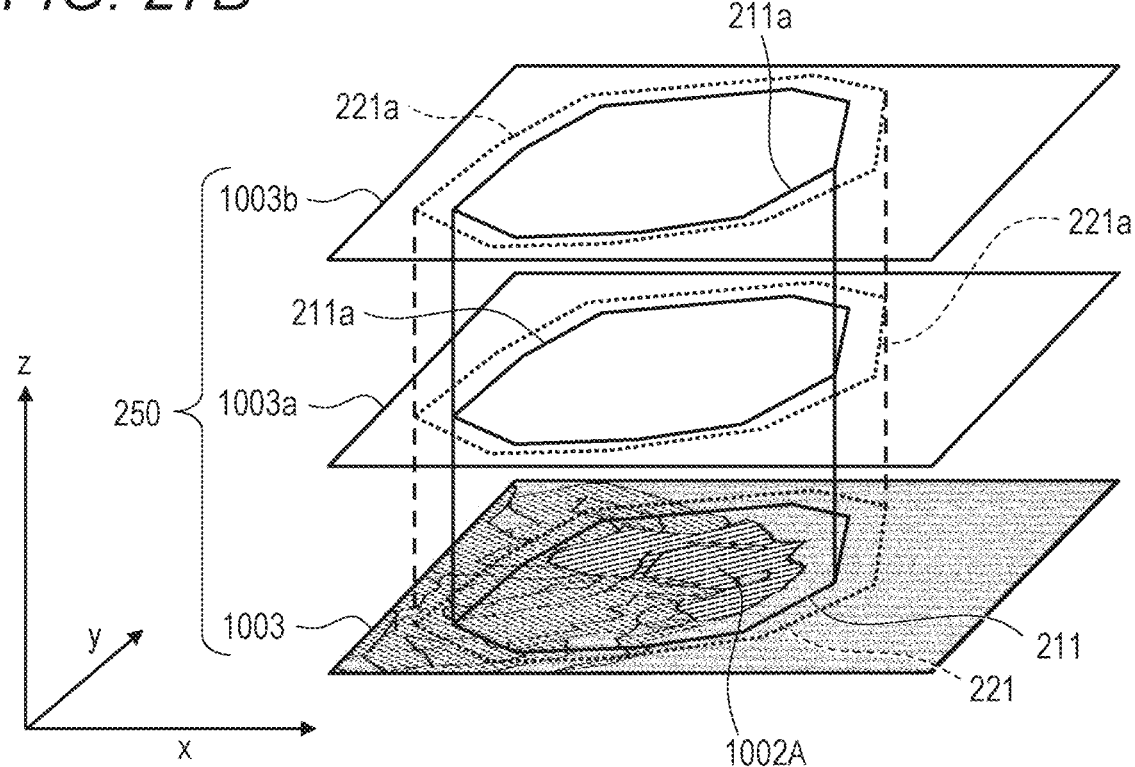
FIG. 27B is a view (part 2) showing an outline of a method of generating a 3D image.

As shown in FIG. 27B, the computer 100A includes a 3D image processing unit 110A that generates a fifth image: the 3D image 250 (see FIG. 27B) by stacking a plurality of mask images 1003.

(3D Image 250)

FIGS. 27A and 27B are views each showing an outline of the method of generating the 3D image 250.

In the first embodiment, the lesion site is detected for each component, but the detection using a procedure similar to the detection range setting (S160) in FIG. 4 is also applicable to generation of the 3D image 250.

Imaging is continuously performed on the medical image 201 along the z-axis direction. Further, the lesion region 202 suspected of being a lesion site, the inner line 211 set by the user, and the outer line 221 obtained by extending the inner line 211 are shown in the medical image 201. Then, the inner region setting unit 102 projects the inner line 211 of the medical image 201 onto each of a medical image 201a adjacent to the medical image 201 in the z-axis direction and a medical image 201b adjacent to the medical image 201a in the z-direction. Thus, inner lines 211a and 211b are set in the medical images 201a and 201b, respectively. Further, the peripheral region setting unit 103 sets the outer line 221 on the medical image 201, and projects the outer line 221 set in the medical image 201 onto each of the medical image 201a and the medical image 201b, each being adjacent to the medical image 201 in the Z-axis direction. As a result, outer lines 221a and 221b are set in the medical images 201a and 201b, respectively.

Then, as shown in FIG. 27B, the 3D image processing unit 110A stacks a plurality of mask images 1003, 1003a, and 1003b (fourth images) to form a fifth image: the 3D image 250. The mask images 1003, 1003a, and 1003b are generated from the medical images 201, 201a, and 201b shown in FIG. 27A. Note that a mask region 1002A is displayed in the mask image 1003 shown in FIG. 27B. Further, each of the medical images 201, 201a, and 201b shown in FIG. 27A is appropriately referred to as a slice image.

(Lesion Site Highlighting Processing on 3D Image 250)

Figure 28:
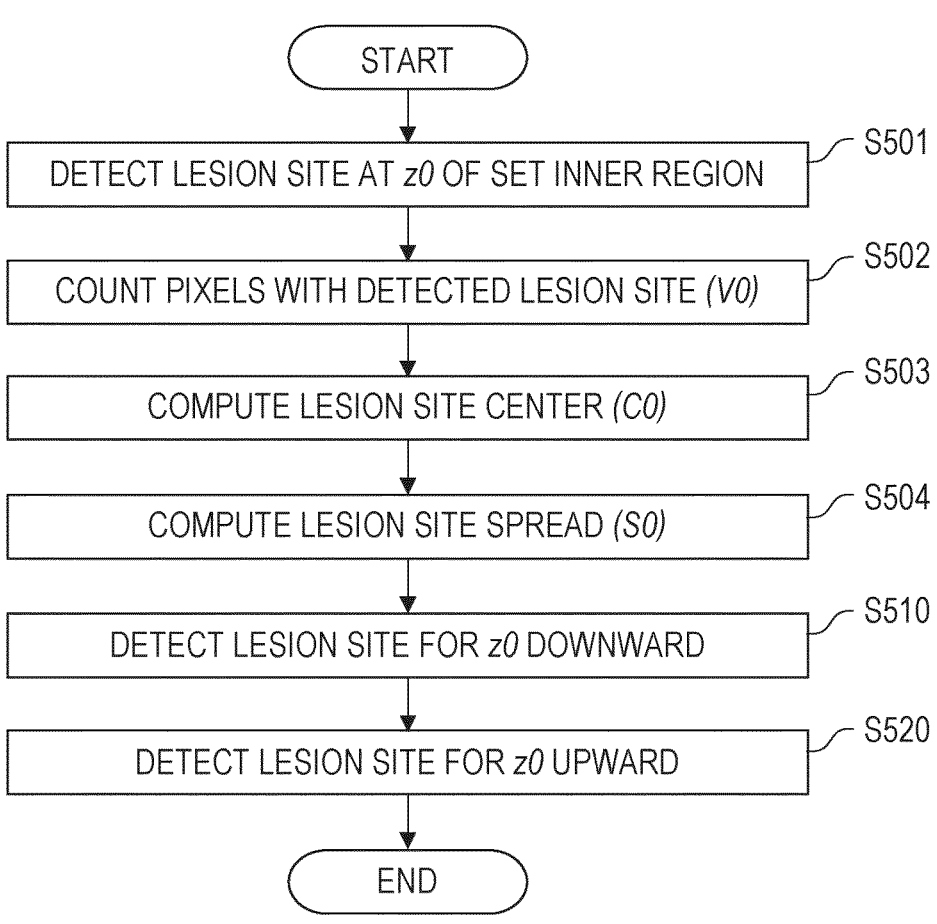
FIG. 28 is a flowchart illustrating the lesion site highlighting processing on the 3D image.

FIG. 28 is a flowchart illustrating the lesion site highlighting processing on the 3D image 250. The processing shown in FIG. 28 is an example of an extension procedure of the first embodiment by the computer 100. A description is made with reference to FIG. 27B as appropriate.

First, the computer 100 detects a lesion site at z0 where the set inner line 211 is present according to steps S110 to S191 in FIG. 4 (Detect lesion site at z0 of set inner region: S501 in FIG. 28). z0 is a location of the z axis where the medical image 201 as a reference is present. The user sets z0 based on the size of the lesion site (mask) or the like. The 3D image 250 is generated by vertically connecting the mask images 1003 with reference to the mask image 1003 located at z0. Particularly, the mask image 1003 (one of the fourth images) located at z0 is appropriately referred to as a reference mask image.

Next, the 3D image processing unit 110A counts the number of pixels with the reference of lesion site (V0), which is a reference of pixel number, from the detected mask region 1002A (see FIG. 27B) (Count pixels with detected lesion site (V0): S502 in FIG. 28). The number of pixels with the reference of lesion site (V0) is a pixel number of the highlighted pixel (the mask region 1002A) in one of the fourth images.

Next, the 3D image processing unit 110A computes the reference of lesion site center (C0), which is a reference of center (Compute lesion site center (C0): S503 in FIG. 28). As the reference of lesion site center (C0), the average value of the x and y locations of pixels corresponding to the lesion site (i.e. in the mask region 1002A) in the reference mask image or the like is used. Specifically, the reference of lesion site center (C0) is the center of gravity of the pixel set by the 3D image processing unit 110A, the pixel corresponding to the mask region 1002A. The reference of lesion site center (C0) is the center of the mask region 1002A as indicated by reference numeral 1203 in FIG. 31A. The reference of lesion site center (C0) is the center of the highlighted pixel (the mask region 1002A).

Subsequently, the 3D image processing unit 110A computes the reference of lesion site spread (S0), which is a reference of spread (Compute lesion site spread (S0): S504 in FIG. 28). The reference of lesion site spread (S0) is an average of distances between the reference of lesion site center (C0) computed in step S503 and each pixel constituting the lesion site (the mask region 1002A). As described above, the reference of lesion site spread (S0) is the average of the distances between the reference of lesion site center (C0) and each pixel constituting the highlighted pixel (the mask region 1002A).

In this manner, in steps S502 to S504, the 3D image processing unit 110A respectively computes the number of pixels with the reference of lesion site (V0), the reference of lesion site center (C0), and the reference of lesion site spread (S0).

After that, the 3D image processing unit 110A detects the lesion site in the adjacent image for z0 downward (Detect lesion site for z0 downward: S510 in FIG. 28). The downward direction is the minus direction of the z axis with reference to z0.

Thereafter, the 3D image processing unit 110A detects the lesion site in the adjacent image for z0 upward (Detect lesion site for z0 upward: S520 in FIG. 28). The upward direction is the plus direction of the z axis with reference to z0.

Processing of step S510 and processing of step S520 will be described later.

(Downward Detection)

Figure 29:
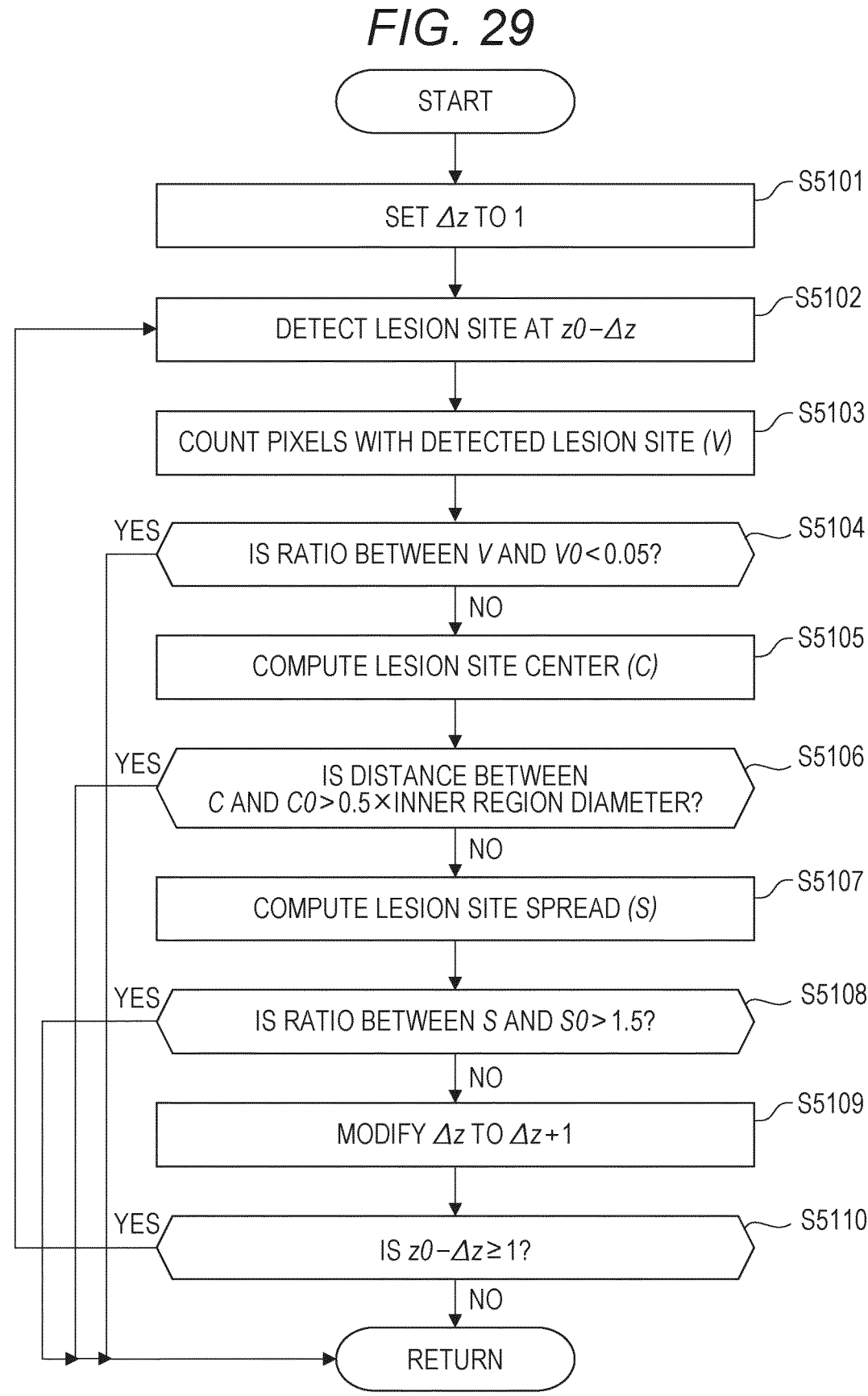
FIG. 29 is a flowchart illustrating a detailed procedure of downward detection.

FIG. 29 is a flowchart illustrating a detailed procedure of downward detection to be performed in step S510 of FIG. 28. A description is made with reference to FIG. 31 as appropriate.

First, the 3D image processing unit 110A sets Δz to 1 (Set Δz to 1: S5101 in FIG. 29).

Next, according to steps S110 to S181 in FIG. 4, the computer 100 detects the lesion site in the adjoining slice image for z0 downward (i.e. the medical image 201 at z0-Δz) using the inner region 212 and the peripheral region 222 set in the medical image 201 to be processed (Detect lesion site at z0-Δz: S5102 in FIG. 29). Specifically, the mask image 1003 is generated by setting the mask region 1002A in the medical image 201 to be processed. Here, the generated mask image 1003 corresponds to the fourth image different from the fourth image in which the number of pixels with the reference of lesion site (V0), the reference of lesion site center (C0), and the reference of lesion site spread (S0) have been calculated.

Note that the component distribution and the lesion site distribution vary for each of the medical images 201. Therefore, the probability difference 601 varies for each component. That is, the detection range may vary across the z axis for each component. However, for example, calculation of the average of the minimum value 605 (see FIG. 12A) and the average value of the maximum value 606 (see FIG. 12A) of the detection range enables the detection range to be maintained in the same range over each of the mask images 1003.

Next, the 3D image processing unit 110A counts the number of pixels with the adjacent lesion site (V), which is an adjacent pixel number, in the mask region 1002A generated in step S5102 (Count pixels with detected lesion site (V): S5103 in FIG. 29). In step S5103, processing similar to that in step S502 in FIG. 28 is performed. The number of pixels with the adjacent lesion site (V) is a pixel number of the highlighted pixel (the mask region 1002A).

Subsequently, the 3D image processing unit 110A determines whether the ratio between the number of pixels with the adjacent lesion site (V) calculated in step S5103 of FIG. 29 and the number of pixels with the reference of lesion site (V0) calculated in step S502 of FIG. 28 is less than 0.05 (a first value that is a predetermined value) (Is ratio between V and V0<0.05: S5104 in FIG. 29).

Figures 31A, 31B, 31C:
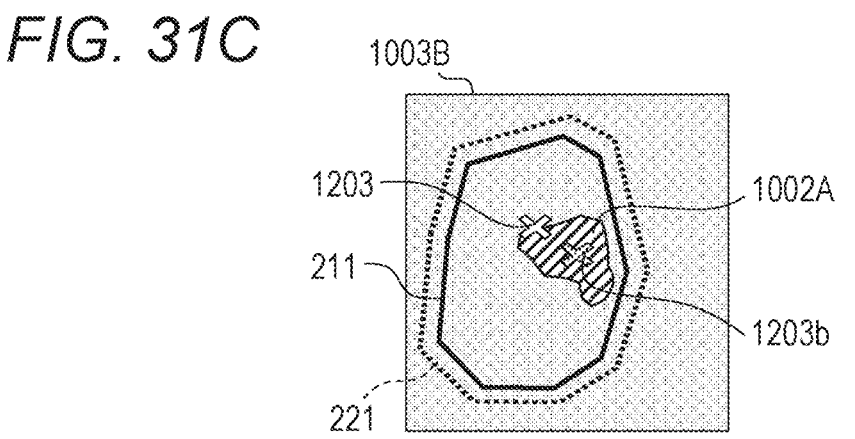
FIG. 31A is a view (part 1) showing a mask image.
FIG. 31B is a view (part 2) showing a mask image.
FIG. 31C is a view (part 3) showing a mask image.

When the ratio between the number of pixels with the adjacent lesion site (V) and the number of pixels with the reference of lesion site (V0) is less than 0.05 (yes in S5104), the detected lesion site is considered to be negligible, because it is small as shown in the mask region 1002A of FIG. 31B. Therefore, further downward detection is not performed, and the 3D image processing unit 110A returns the processing to step S520 in FIG. 28.

When the ratio between the number of pixels with the adjacent lesion site (V) and the number of pixels with the reference of lesion site (V0) is equal to or greater than 0.05 (no in S5104), the lesion site is considered to be still remarkable as shown in the mask region 1002A of FIG. 31C.

Therefore, the 3D image processing unit 110A computes an adjacent lesion site center (C), which is an adjacent center, for the mask region 1002A generated in step S5102 (Compute lesion site center (C): S5105 in FIG. 29). This processing is similar to the processing performed in step S503 in FIG. 28. The adjacent lesion site center (C) is the same as the reference of lesion site center (C0), and the average value of the x and y locations of pixels corresponding to the lesion site or the like is used. The adjacent lesion site center (C) is the center of the highlighted pixel (the mask region 1002A).

Next, the 3D image processing unit 110A determines whether the distance between the adjacent lesion site center (C) and the reference of lesion site center (C0) is greater than (0.5×inner region diameter) (Is distance between C and C0> (0.5×inner region diameter)?: S5106 in FIG. 29). The inner region diameter is a major diameter of an ellipse with the smallest area among ellipses including the inner line 211 (see FIG. 7) therein. Note that the inner region diameter is approximated by Formula (1) below since the inner region 212 is formed not only in a circle but also in a polygon.

[Math 1]

$$\sqrt{\frac{4 \times \text{inner area}}{\pi}} \tag{1}$$

In Formula (1), the "inner area" is the area of the inner region 212.

For example, the 3D image processing unit 110A determines whether the distance between the reference of lesion site center (reference numeral 1203: C0) in FIG. 31A and the adjacent lesion site center (reference numeral 1203: C) in FIG. 31C is greater than (0.5×inner region diameter) (a second value that is a predetermined value). Specifically, the 3D image processing unit 110A calculates a distance between a place (reference numeral 1203 in FIG. 31C) obtained by projecting the reference of lesion site center (reference numeral 1203: C0) in FIG. 31A onto a mask image 1003B in FIG. 31C and the adjacent lesion site center (C) (reference numeral 1203$b$) in FIG. 31C.

Figure 31D:
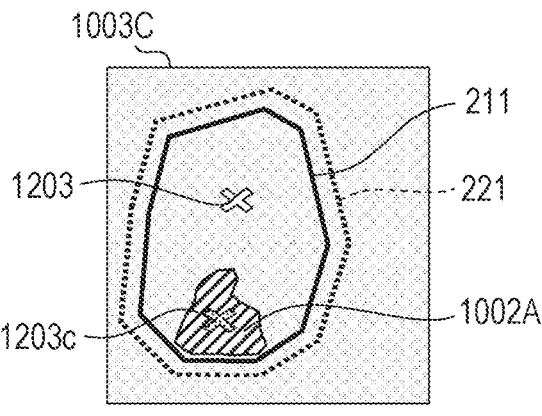
FIG. 31D is a vies (part 4) showing a mask image.

When the distance between the reference of lesion site center (C0) and the adjacent lesion site center (C) is greater than (0.5×the inner region diameter) (yes in S5106), the following factors are considered. That is, in such a case, as shown in FIGS. 31A and 31D, a lesion site having the reference of lesion site center (C0) (reference numeral 1203 in FIG. 31A) and a lesion site having the adjacent lesion site center (C) (reference numeral 1003C in a mask image 1203$c$ in FIG. 31D) are considered to belong to unrelated lesion sites. In a case where "yes" is determined in step S5106 of FIG. 29, further processing related to the medical image 201 in the downward direction is not performed. Therefore, the 3D image processing unit 110A advances the processing to step S520 in FIG. 28. In this way, it is possible to prevent an unrelated lesion site from being erroneously detected as the lesion site shown in the mask image 1003 located at z0.

When the distance between the reference of lesion site center (C0) and the adjacent lesion site center (C) is equal to or less than (0.5×the inner region diameter) (no in S5106), the 3D image processing unit 110A computes an adjacent lesion site spread(S), which is an adjacent spread, for the mask image 1003 to be processed (Compute lesion site spread(S): S5107 in FIG. 29). The adjacent lesion site spread(S) is an average of distances between the adjacent lesion site center (C) computed in step S5105 and each pixel constituting the lesion site (the mask region 1002A) in the mask image 1003 to be processed. The adjacent lesion site spread(S) is an average of distances between the adjacent lesion site center (C) and each pixel constituting the highlighted pixel (the mask region 1002A).

As described above, in steps S5103, S5105, and S5107, the 3D image processing unit 110A respectively computes the number of pixels with the adjacent lesion site (V), the adjacent lesion site center (C), and the adjacent lesion site spread(S).

Then, the 3D image processing unit 110A determines whether the ratio between the adjacent lesion site spread(S) and the reference of lesion site spread (S0) is greater than 1.5 (Is ratio between S and S0>1.5?: S5108 in FIG. 29).

Figure 31E:
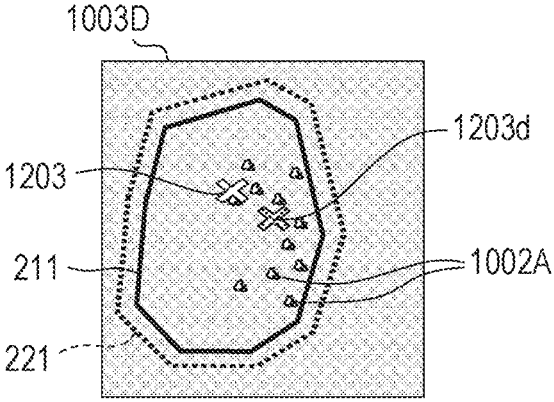
FIG. 31E is a view (part 5) showing a mask image.

When the ratio between the adjacent lesion site spread (S) and the reference of lesion site spread (S0) is greater than 1.5 (a third value that is a predetermined value) (yes in S5108), it is considered that the detected lesion sites are scattered in the mask image 1003 to be processed, as shown in a mask image 1003D of FIG. 31E. That is, it is considered that there is a lot of noise. Therefore, the processing is not performed downward from the mask image 1003 that is the current processing target. That is, the 3D image processing unit 110A advances the processing to step S520 in FIG. 28. In this way, in a case where lesion sites are scattered, i.e. in a case where noise is observed, it is possible to prevent these lesion sites from being connected.

In a case where the ratio between the adjacent lesion site spread(S) and the reference of lesion site spread (S0) is equal to or less than 1.5 (no in S5108), the 3D image processing unit 110A modifies $\Delta z$ to $\Delta z+1$ (Modify $\Delta z$ to $\Delta z+1$: S5109 in FIG. 29), and thus the downward detection continues. That is, the 3D image processing unit 110A continues to select the mask images 1003, as the mask images 1003 constituting the 3D image 250, from the plurality of mask images 1003 until one of the following (A1) to (A3) is true.

(A1) The ratio between the number of pixels with the adjacent lesion site (V) and the number of pixels with the reference of lesion site (V0) is less than the first value ("0.05" in the present embodiment) as a predetermined value (S5104).

(A2) The distance between the adjacent lesion site center (C) and the reference of lesion site center (C0) is greater than the second value (0.5×inner region in the present embodiment) as a predetermined value (S5106).

(A3) The ratio between the adjacent lesion site spread(S) and the reference of lesion site spread (S0) is greater than the third value ("1.5" in the present embodiment) as a predetermined value.

After modification of $\Delta z$, the 3D image processing unit 110A determines whether $Z0-\Delta z \geq 1$ is satisfied (Is $z0-\Delta z \geq 1$?: S5110 in FIG. 29).

In a case where $Z0-\Delta z \geq 1$ is satisfied (yes in S5110), the 3D image processing unit 110A returns the processing to step S5102, and performs the processing in step S5102 and subsequent steps on the medical image 201 below the processed medical image. Note that z0 (medical image 201 as a reference) is fixed through the processing of FIG. 29. That is, the number of pixels with the reference of lesion site (V0), the reference of lesion site center (C0), and the reference of lesion site spread (S0) used are fixed.

Meanwhile, when $Z0-\Delta z \geq 1$ is not satisfied (no in S5110), the 3D image processing unit 110A determines that the slice image processed last is the lowermost slice image in the z direction. Therefore, the processing is not performed downward from the medical image 201 that is the current processing target. Then, the 3D image processing unit 110A advances the processing to step S520 in FIG. 28.

Note that the threshold for the ratio between the number of pixels with the adjacent lesion site (V) and the number of pixels with the reference of lesion site (V0) in step S5104 is 0.05, but is not limited to this value. Further, the threshold for the distance between the adjacent lesion site center (C) and the reference of lesion site center (C0) in step S5106 is (0.5×the inner region diameter), but is not limited to this value. Furthermore, the threshold for the adjacent lesion site spread(S) and the reference of lesion site spread (S0) in step S5108 is 1.5, but is not limited to this value.

Note that the number of pixels with the reference of lesion site (V), the reference of lesion site center (C0), and reference of lesion site spread (S0) are computed from the mask image 1003 at the location of z0 initially designated by the inner line 211. Then, although these values are fixed throughout FIG. 29, the values of the number of pixels with the reference of lesion site (V0), the reference of lesion site center (C0), and the reference of lesion site spread (S0) may indicate the state at adjacent z. That is, each time the processing is shifted to the adjoining medical image 201, the number of pixels with the reference of lesion site (V0), the reference of lesion site center (C0), and the reference of lesion site spread (S0) may be recomputed based on the mask image 1003 processed before that.

(Upward Detection)

Figure 30:
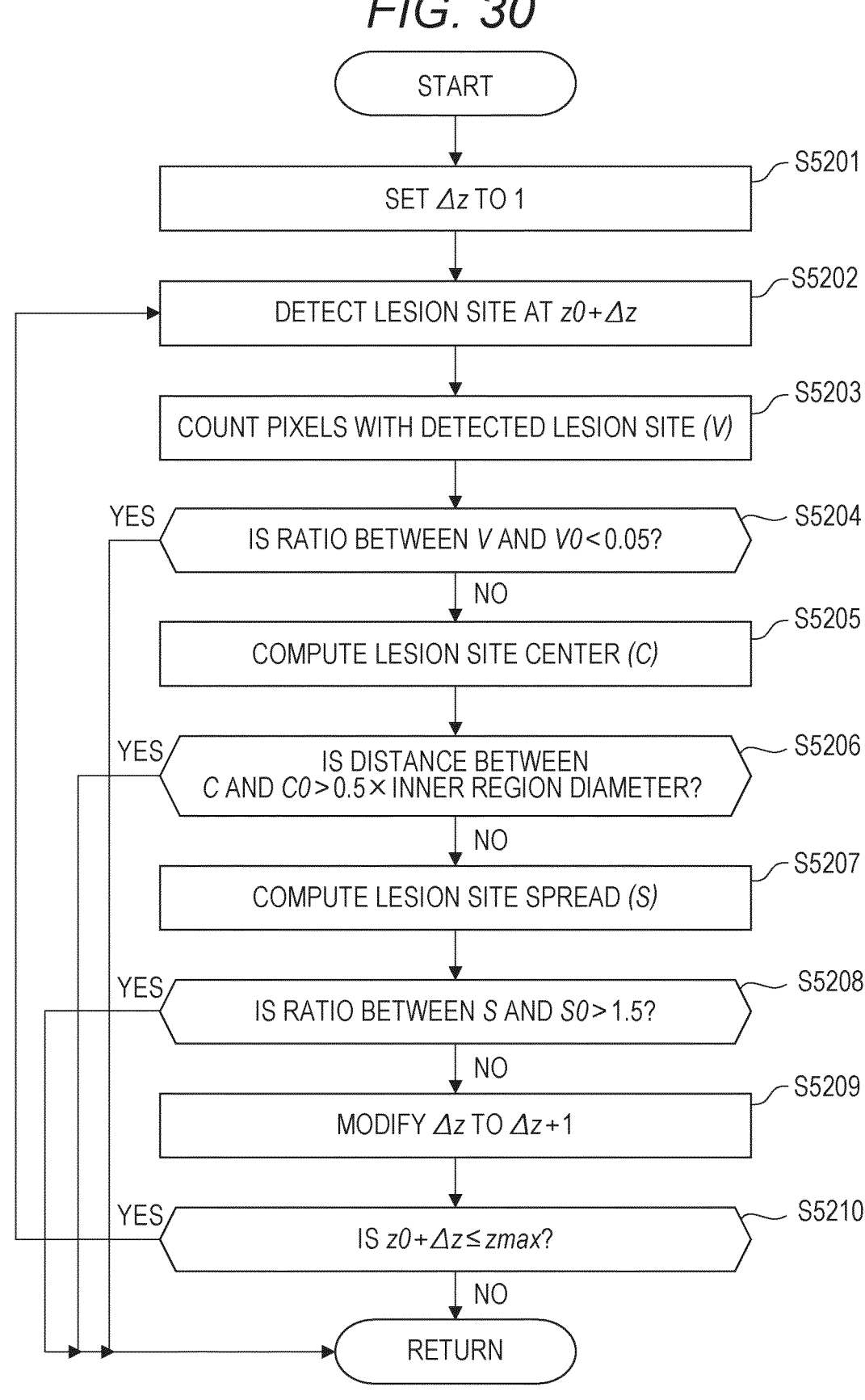
FIG. 30 is a flowchart illustrating a detailed procedure of upward detection.

FIG. 30 is a flowchart illustrating a detailed procedure of upward detection to be performed in step S520 of FIG. 28. A description is made with reference to FIG. 31 as appropriate.

First, the 3D image processing unit 110A sets a step of $\Delta z$ to 1 (Set $\Delta z$ to 1: S5201 in FIG. 30).

Next, the computer 100 detects the lesion site in the adjoining slice image for z0 upward (i.e. z0+$\Delta z$) using the same inner region 212 and peripheral region 222 according to steps S110 to S191 in FIG. 4 (Detect lesion site at z0+$\Delta z$: S5202 in FIG. 30).

Note that the component distribution and the lesion site distribution vary for each of the medical images 201. Therefore, the probability difference 601 varies for each component. That is, the detection range may vary across the z axis for each component. However, for example, calculation of the average of the minimum value 605 (see FIG. 12A) and the average value of the maximum value 606 (see FIG. 12A) of the detection range enables the detection range to be maintained in the same range over each of the mask images 1003.

Next, the 3D image processing unit 110A counts the number of pixels with the adjacent lesion site (V), which is the adjacent pixel number, from the mask generated in S5202 (Count pixels with detected lesion site (V): S5203 in FIG. 30).

Subsequently, the 3D image processing unit 110A determines whether the ratio between the number of pixels with the adjacent lesion site (V) calculated in step S5203 of FIG. 30 and the number of pixels with the reference of lesion site (V0) calculated in step S502 of FIG. 28 is less than 0.05 (Is ratio between V and V0<0.05?: S5204 in FIG. 30).

When the ratio between the number of pixels with the adjacent lesion site (V) and the number of pixels with the reference of lesion site (V0) is less than 0.05 (yes in S5204), the detected lesion site is negligible, because it is small as shown in the mask region 1002A of FIG. 31B. Therefore, further upward detection is not performed, and the 3D image processing unit 110A ends the processing of FIG. 30 and the processing of FIG. 28.

When the ratio between the number of pixels with the adjacent lesion site (V) and the number of pixels with the reference of lesion site (V0) is equal to or greater than 0.05 (no in S5204), the lesion site is considered to be still remarkable as shown in the mask region 1002A of FIG. 31C.

Therefore, the 3D image processing unit 110A computes the adjacent lesion site center (C), which is the adjacent center, for the mask generated in step S5202 (Compute lesion site center (C): S5205 in FIG. 30). This processing is similar to the processing performed in step S503 in FIG. 28, and the average value of the x and y locations of pixels corresponding to the lesion site or the like is used for the adjacent lesion site center (C).

Next, the 3D image processing unit 110A determines whether the distance between the adjacent lesion site center (C) and the reference of lesion site center (C0) is greater than (0.5×the inner region diameter) (Is distance between C and C0> (0.5×inner region diameter)?: S5206 in FIG. 30). The definition of the inner region diameter is as described above. Note that the inner region diameter is approximated by Formula (2) below since the inner region 212 is formed not only in a circle but also in a polygon.

[Math 2]

$$\sqrt{\frac{4 \times \text{inner area}}{\pi}} \qquad (2)$$

In Formula (2), the "inner area" is the area of the inner region.

For example, the 3D image processing unit 110A determines whether the distance between the reference of lesion site center (reference numeral 1203: C0) in FIG. 31A and the adjacent lesion site center (reference numeral 1203: C) in FIG. 31B is greater than (0.5×inner region diameter). Specifically, the 3D image processing unit 110A calculates the distance between the place (reference numeral 1203 in FIG. 31 C) obtained by projecting the reference of lesion site center (reference numeral 1203: C0) in FIG. 31A onto the mask image 1003B in FIG. 31C and the adjacent lesion site center (reference numeral 1203b: C) in FIG. 31C.

When the distance between the reference of lesion site center (C0) and the adjacent lesion site center (C) is greater than (0.5×inner region diameter) (yes in S5206), the lesion site with the reference of lesion site center (C0) and the lesion site with the adjacent lesion site center (C) are considered to belong to unrelated lesion sites. In a case where "yes" is determined in step S5205 of FIG. 30, further processing related to the medical image 201 in the upward direction is not performed. Therefore, the 3D image processing unit 110A ends the processing of FIG. 30 and the processing of FIG. 28. In this way, it is possible to prevent an unrelated lesion site from being erroneously detected as the lesion site shown in the medical image 201 located at z0.

When the distance between the reference of lesion site center (C0) and the adjacent lesion site center (C) is equal to or less than (0.5×the inner region diameter) (no in S5206), the 3D image processing unit 110A computes an adjacent lesion site spread(S), which is the adjacent spread, for the mask image 1003 to be processed (Compute lesion site spread(S): S5207 in FIG. 30). The adjacent lesion site spread(S) is an average of distances between the adjacent lesion site center (C) computed in step S5205 and each pixel constituting the lesion site (the mask) in the mask image 1003 to be processed.

Then, the 3D image processing unit 110A determines whether the ratio between the adjacent lesion site spread(S) and the reference of lesion site spread (S0) is greater than 1.5 (Is ratio between S and S0>1.5?: S5208 in FIG. 30).

When the ratio between the adjacent lesion site spread(S) and the reference of lesion site spread (S0) is greater than 1.5 (yes in S5208), it is considered that the detected lesion sites are scattered in the mask image 1003 to be processed, as shown in the mask image 1003D of FIG. 31E. That is, it is considered that there is a lot of noise. Therefore, the processing is not performed upward from the medical image 201 that is the current processing target. That is, the 3D image processing unit 110A ends the processing of FIG. 30 and the processing of FIG. 28. In this way, in a case where lesion sites are scattered, i.e. in a case where noise is observed, it is possible to prevent these lesion sites from being connected.

In a case where the ratio between the adjacent lesion site spread(S) and the reference of lesion site spread (S0) is equal to or less than 1.5 (no in S5208), the 3D image processing unit 110A modifies $\Delta z$ to $\Delta z + 1$ (Modify $\Delta z$ to $\Delta z + 1$: S5209 in FIG. 30).

After modification of $\Delta z$, the 3D image processing unit 110A determines whether $Z0 + \Delta z \leq zmax$ is satisfied (Is $z0 + \Delta z \leq zmax$?: S5210 in FIG. 30).

In a case where $Z0 + \Delta z \leq zmax1$ is satisfied (yes in S5210), the 3D image processing unit 110A returns the processing to step S5202, and performs the processing in step S5202 and subsequent steps on the medical image 201 above the processed medical image. Note that z0 (the medical image 201 as a reference) is fixed through the processing of FIG. 30. That is, the number of pixels with the reference of lesion site (V0), the reference of lesion site center (C0), and the reference of lesion site spread (S0) used are fixed.

When $Z0 + \Delta z \leq zmax$ is not satisfied (no in S5210), the 3D image processing unit 110A determines that the slice image processed last is the uppermost slice image in the z direction. Therefore, the processing is not performed upward from the medical image 201 that is the current processing target. Then, the 3D image processing unit 110 ends the processing of FIG. 30 and the processing of FIG. 28.

Note that the threshold for the ratio between the number of pixels with the adjacent lesion site (V) and the number of pixels with the reference of lesion site (V0) in step S5204 is 0.05, but is not limited to this value. Further, the threshold for the distance between the adjacent lesion site center (C) and the reference of lesion site center (C0) in step S5206 is (0.5×the inner region diameter), but is not limited to this value. Furthermore, the threshold for the adjacent lesion site spread(S) and the reference of lesion site spread (S0) in step S5208 is 1.5, but is not limited to this value.

Note that the number of pixels with the reference of lesion site (V0), the reference of lesion site center (C0), and the reference of lesion site spread (S0) are computed from the mask image 1003 at the location of z0 initially designated by the inner line 211. Then, although these values are fixed throughout FIG. 30, the values of the number of pixels with the reference of lesion site (V0), the reference of lesion site center (C0), and the reference of lesion site spread (S0) may indicate the state at adjoining z. That is, each time the processing is shifted to the adjoining medical image 201, the number of pixels with the reference of lesion site (V0), the reference of lesion site center (C0), and the reference of lesion site spread (S0) may be recomputed based on the mask image 1003 processed before that.

The lesion site (the mask region 1002A) is not displayed in all the mask images 1003. In the second embodiment, three parameters of the number of pixels with lesion site, the lesion site center, and the lesion site spread are determined over each of the mask images 1003, but are not limited to these parameters.

FIGS. 31A to 31E are views showing the mask images 1003 having different z locations. In the mask images 1003 shown in FIGS. 31A to 31E, each of the mask regions 1002A is displayed as a lesion site.

The mask image 1003 shown in FIG. 31A is an example based on the reference mask image located at z0.

In the mask image 1003 shown in FIG. 31A, the mask region 1002A is displayed, and the reference of lesion site center (C0) computed in step S503 in FIG. 28 is indicated by reference numeral 1203. Further, although not shown in FIG. 31A, the number of pixels with the reference of lesion site (V0) and the reference of lesion site spread (S0) are computed based on the mask image 1003 (S502, S503, and S504 in FIG. 28).

Then, the mask images 1003A to 1003D shown in FIGS. 31B to 31E are the mask images 1003 present at different z locations from the mask image 1003 based on the reference mask image of FIG. 31A. Note that the inner line 211 and the outer line 221 of the mask image 1003 shown in FIG. 31A are projected onto each of the mask images 1003A to 1003D shown in FIGS. 31B to 31E. Further, FIGS. 31B to 31E each show the mask region 1002A. Based on the mask images 1003A to 1003D shown in FIGS. 31B to 31E, the number of pixels with the adjacent lesion site (V), the adjacent lesion site center (C), and the adjacent lesion site spread(S) are computed (S5103, S5105, and S5107 in FIG. 29).

The mask image 1003B shown in FIG. 31C has the following conditions.

(A1) The ratio between the number of pixels with the adjacent lesion site (V) and the number of pixels with the reference of lesion site (V0) is equal to or greater than 0.05.

(A2) The distance between the adjacent lesion site center (C) (reference numeral 1203b) and the reference of lesion site center (C0) (reference numeral 1203) is equal to or less than (0.5×inner region diameter).

(A3) The ratio between the adjacent lesion site spread(S) and the reference of lesion site spread (S0) is equal to or less than 1.5.

Therefore, in the mask image 1003B shown in FIG. 31C, "no" is selected in all of steps S5104, S5106, and S5108 in FIG. 29 or in all of steps S5204, S5206, and S5208 in FIG. 30. That is, the lesion site (the mask region 1002A) indicated by the mask image 1003B is determined to be the same (continuous) lesion site as the lesion site (the mask region 1002A) indicated by the mask image 1003 in FIG. 31A.

The mask image 1003A shown in FIG. 31B satisfies the following condition.

(B1) The ratio between the number of pixels with the adjacent lesion site (V) and the number of pixels with the reference of lesion site (V0) is less than 0.05.

Therefore, in the mask image 1003A shown in FIG. 31B, "yes" is selected in step S5104 in FIG. 29 or step S5204 in FIG. 30.

The mask image 1003C shown in FIG. 31D has the following conditions.

(C1) The distance between the adjacent lesion site center (C) (reference numeral 1203c) and the reference of lesion site center (C0) (reference numeral 1203) is greater than (0.5×inner region diameter).

Therefore, in the mask image 1003C shown in FIG. 31D, "yes" is selected in step S5106 in FIG. 29 or step S5206 in FIG. 30.

The mask image 1003D shown in FIG. 31E has the following conditions.

(D1) The ratio between the adjacent lesion site spread(S) and the reference of lesion site spread (S0) is greater than 1.5.

(D2) The distance between the adjacent lesion site center (C) (reference numeral 1203) and the reference of lesion site center (C0) (reference numeral 1203d) is equal to or less than (0.5×inner region diameter).

Therefore, in the mask image 1003D shown in FIG. 31E, "yes" is determined in step S5108 in FIG. 29 or step S5208 in FIG. 30.

In the example shown in FIG. 31E, even when the distance between the adjacent lesion site center (C) (reference numeral 1203d) and the reference of lesion site center (C0) (reference numeral 1203) is equal to or less than (0.5×inner region diameter), lesion sites are scattered. In such a case, the ratio between the adjacent lesion site spread(S) and the reference of lesion site spread (S0) is greater than 1.5 (a predetermined value).

According to the second embodiment, the 3D image 250 (see FIG. 27) can be constructed by using the plurality of mask images 1003. Particularly, the number of pixels with lesion site (V0, V), the lesion site center (C0, C), and the lesion site spread (S0, S) are compared, and the mask image 1003 that does not satisfy the conditions is excluded from the configuration of the 3D image 250. In this way, the mask images 1003 constituting the 3D image 250 can be quantitatively selected.

Third Embodiment

Next, the third embodiment of the present invention will be described with reference to FIGS. 32 to 37. In the third embodiment, the component images 401 are selected, and a combined component image 260 (see FIG. 34B) obtained by synthesizing the selected component images 401 is generated. Then, lesion site highlighting processing is performed on the combined component image 260. Note that the configuration of the computer 100 in the third embodiment is similar to that in FIG. 2, and thus illustration is omitted. (Overall Processing)

Figure 32:
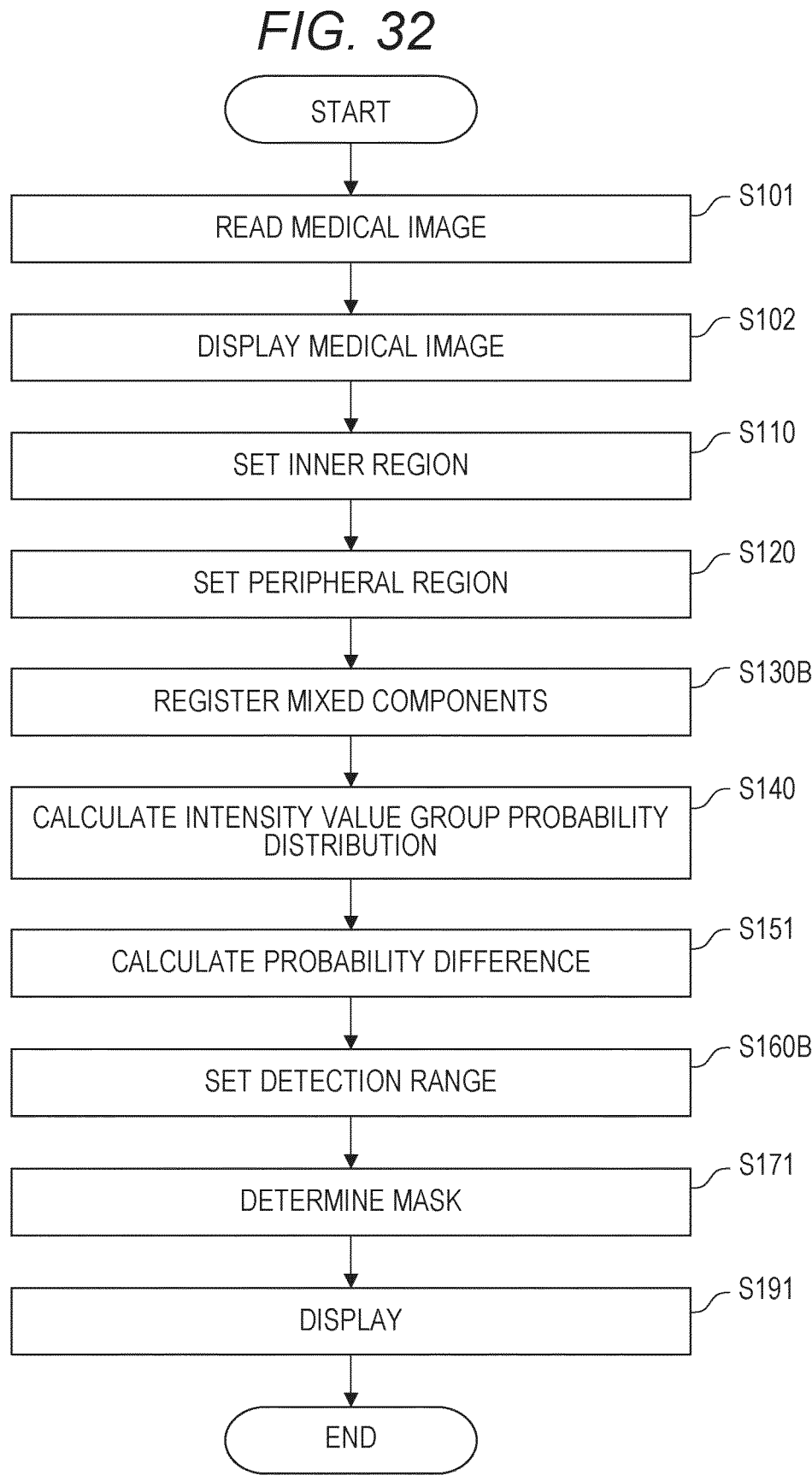
FIG. 32 is a flowchart illustrating an overall procedure of lesion site highlighting processing performed in a third embodiment.

FIG. 32 is a flowchart illustrating an overall procedure of lesion site highlighting processing performed in the third embodiment by the computer 100. In FIG. 32, the processing similar to that in FIG. 4 is denoted by the same step numbers, and redundant description is omitted.

In the processing illustrated in FIG. 32, the processing of step S130B is performed instead of step S130 of FIG. 4.

In step S130B, the component image processing unit 104 generates the combined component image 260 (Register mixed components). Processing of step S130B will be described later with reference to FIG. 33.

Further, in FIG. 4, the processing of steps S140 to S171 is repeated for each component, but the processing of steps S140 to S171 is not repeated in the processing illustrated in FIG. 32.

Step S160 in FIG. 4 is step S160B described later. Further, the processing of step S181 is omitted. (Generation of Combined Component Image)

Figure 33:
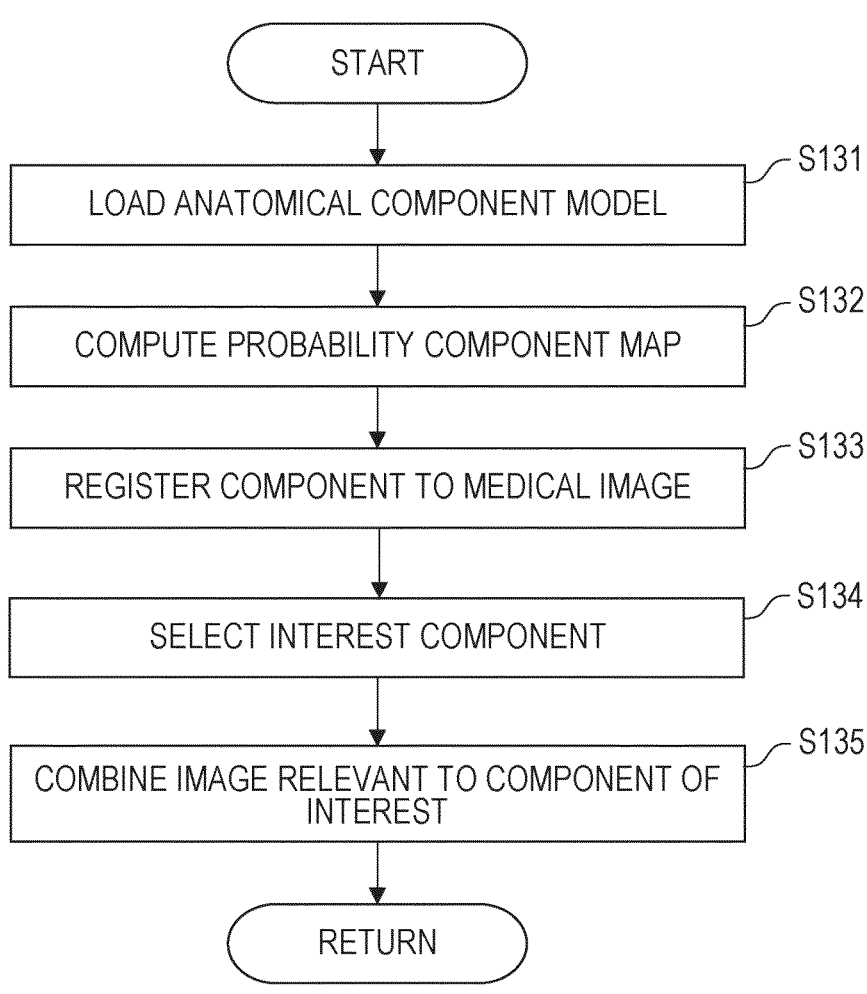
FIG. 33 is a flowchart illustrating a detailed procedure regarding generation of a combined component image.

FIG. 33 is a flowchart illustrating a detailed procedure regarding generation of the combined component image 260 (see FIG. 34B) in step S130B of FIG. 32.

First, the component image processing unit 104 reads an anatomical component model (not illustrated) or the like stored in the storage device 120 (Load anatomical component model: S131 in FIG. 8).

Next, the component image processing unit 104 computes a probability component map related to component information of each pixel according to the read anatomical component model (Compute probability component map: S132 in FIG. 8). As a result, the feature of the pixel for each component is computed.

Then, the component image processing unit 104 refers to the probability component map for each pixel of the medical image 201 and determines which component the current processing target belongs to has the highest probability (a predetermined criterion) (Register component to medical image: S133 in FIG. 8). As a result, the component images 401 (see FIGS. 9B to 9E) are generated.

Thereafter, the user selects an interest component (e.g. gray matter and white matter) via the input device 131 (Select interest component: S134).

Then, the component image processing unit 104 combines (synthesizes) the component images 401 relevant to the component of interest (e.g. gray matter and white matter) selected in step S134 (Combine image relevant to component of interest: S135). Note that the component image 401 of a component (e.g. skull and background) not selected in step S134 is ignored.

Figure 34A:
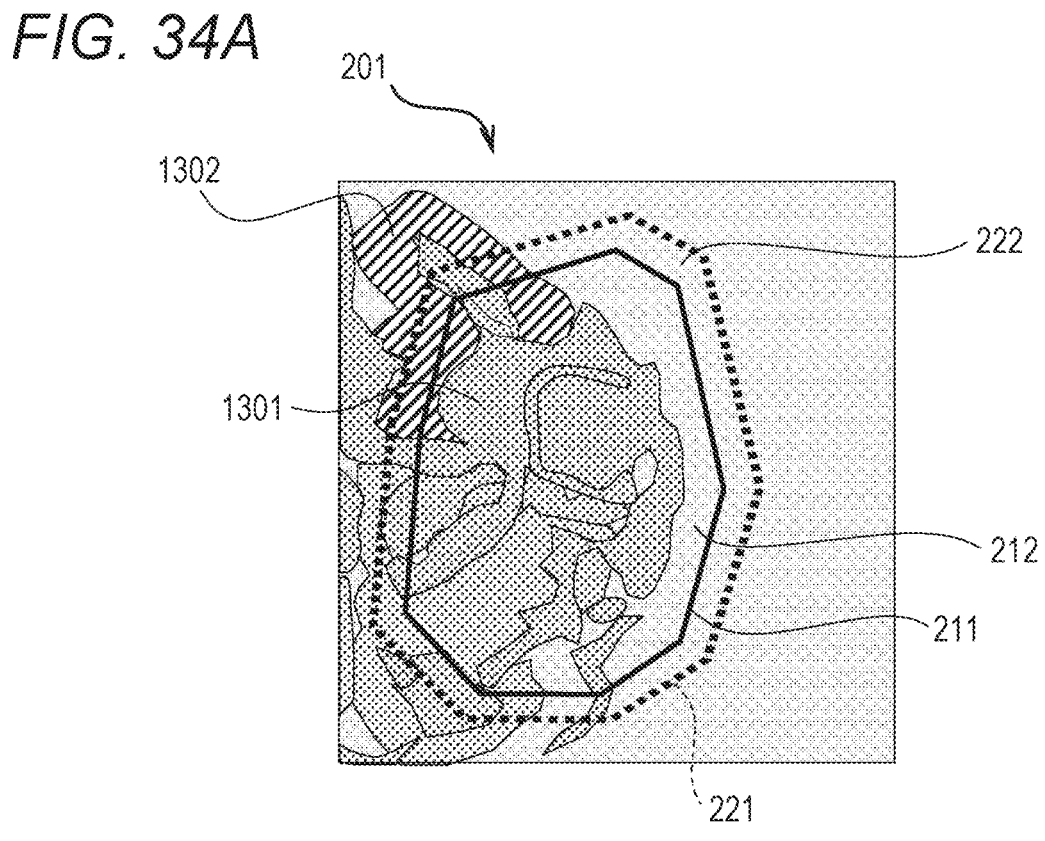
FIG. 34A is a view showing a medical image before being decomposed.
Figure 34B:
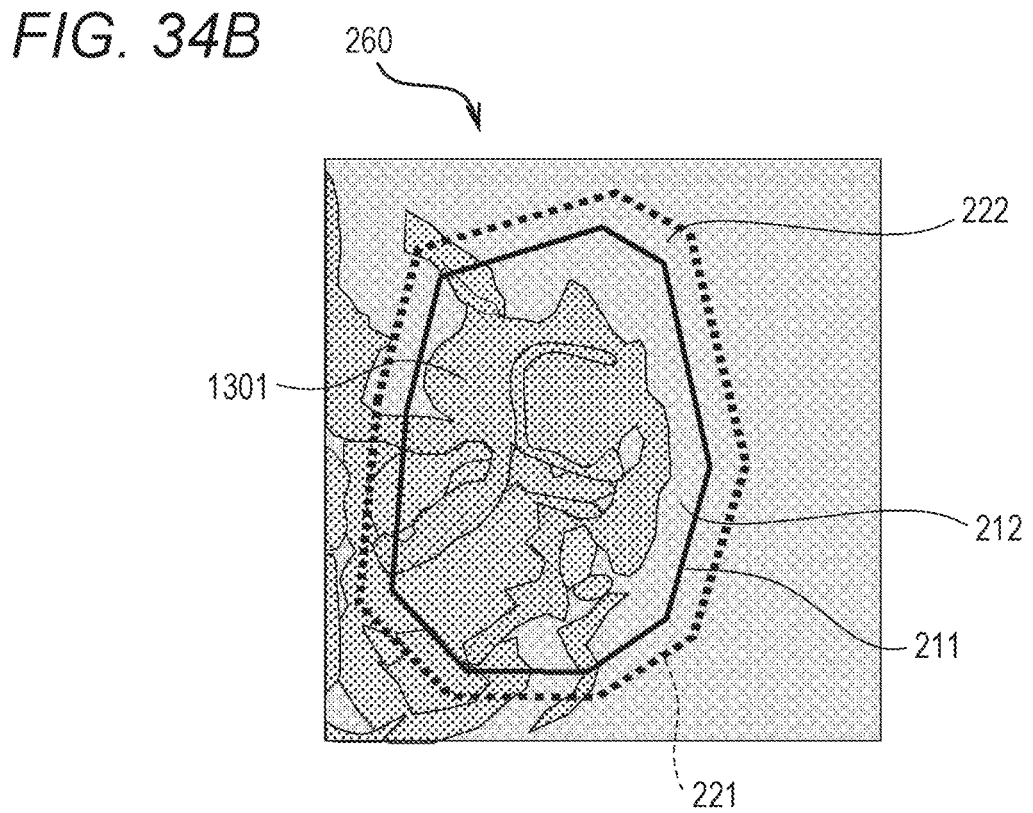
FIG. 34B is a view showing an example of a combined component image.

As a result, the combined component image 260 as shown in FIG. 34B is generated as a new second image. After completion of step S135 in FIG. 33, the computer 100 returns the processing to step S140 in FIG. 4.

(Example of Generation of Combined Component Image)

FIG. 34A is a view showing the medical image 201 before being decomposed in steps S131 to S133 of FIG. 33.

In the example shown in FIG. 34A, the inner line 211, the outer line 221, the inner region 212, and the peripheral region 222 set in steps S110 and S120 in FIG. 32 are shown.

In the medical image 201 shown in FIG. 34A, two components, a component in which the user is interested (reference numeral 1301) and a component in which the user is not interested (reference numeral 1302), are identified. These two components are present in both the inner region 212 and the peripheral region 222. The component image processing unit 104 synthesizes only the component image 401 (see FIGS. 9B to 9E) of the component (reference numeral 1301) of interest to the user, and ignores the component image 401 of the component (reference numeral 1302) of no interest.

FIG. 34B is a view showing an example of the combined component image 260 generated in step S135 of FIG. 33.

The combined component image 260 is an image in which the component (reference numeral 1302) of no interest in FIG. 34A is omitted. In FIG. 34B, reference numerals other than the combined component image 206 are the same as those in FIG. 34A, and thus redundant description is omitted.

In this manner, the component image processing unit 104 generates an image obtained by synthesizing the predetermined component image 401 among the plurality of component images 401, and sets the image as the combined component image 260 (a new second image).

(Intensity Value Group Probability Distribution 500E)

Figure 35:
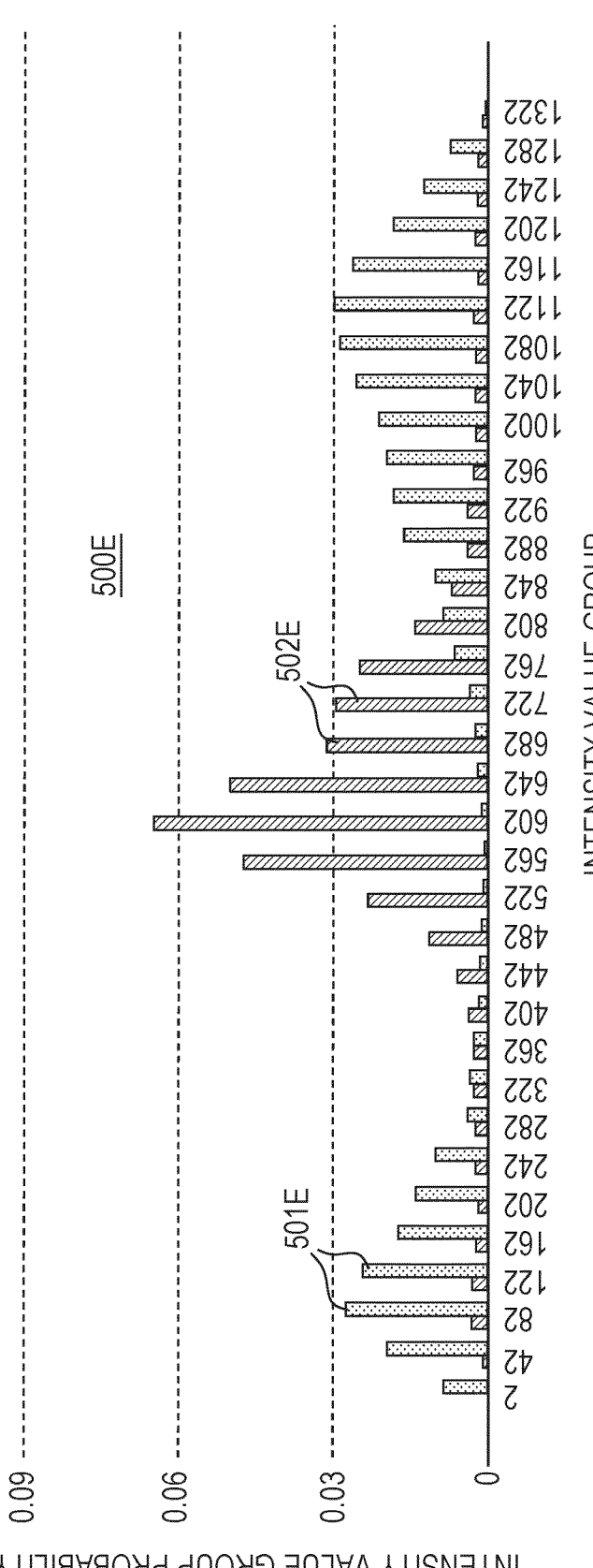
FIG. 35 is a diagram illustrating an example of the intensity value group probability distribution based on the combined component image.

FIG. 35 is a diagram illustrating an example of an intensity value group probability distribution 500E based on the combined component image 260, used in the third embodiment. The intensity value group probability distribution in FIG. 35 is generated in step S140 of FIG. 32.

In FIG. 35, in the horizontal view 34?, the horizontal axis represents an intensity value group, and the vertical axis represents an intensity value group probability. Further, in FIG. 35, an inner region histogram 501E is an intensity value group probability in the inner region 212 of the combined component image 260. A peripheral region histogram 502E is an intensity value group probability in the peripheral region 222 of the combined component image 260.

(Probability Difference Distribution 600E)

Figure 36:
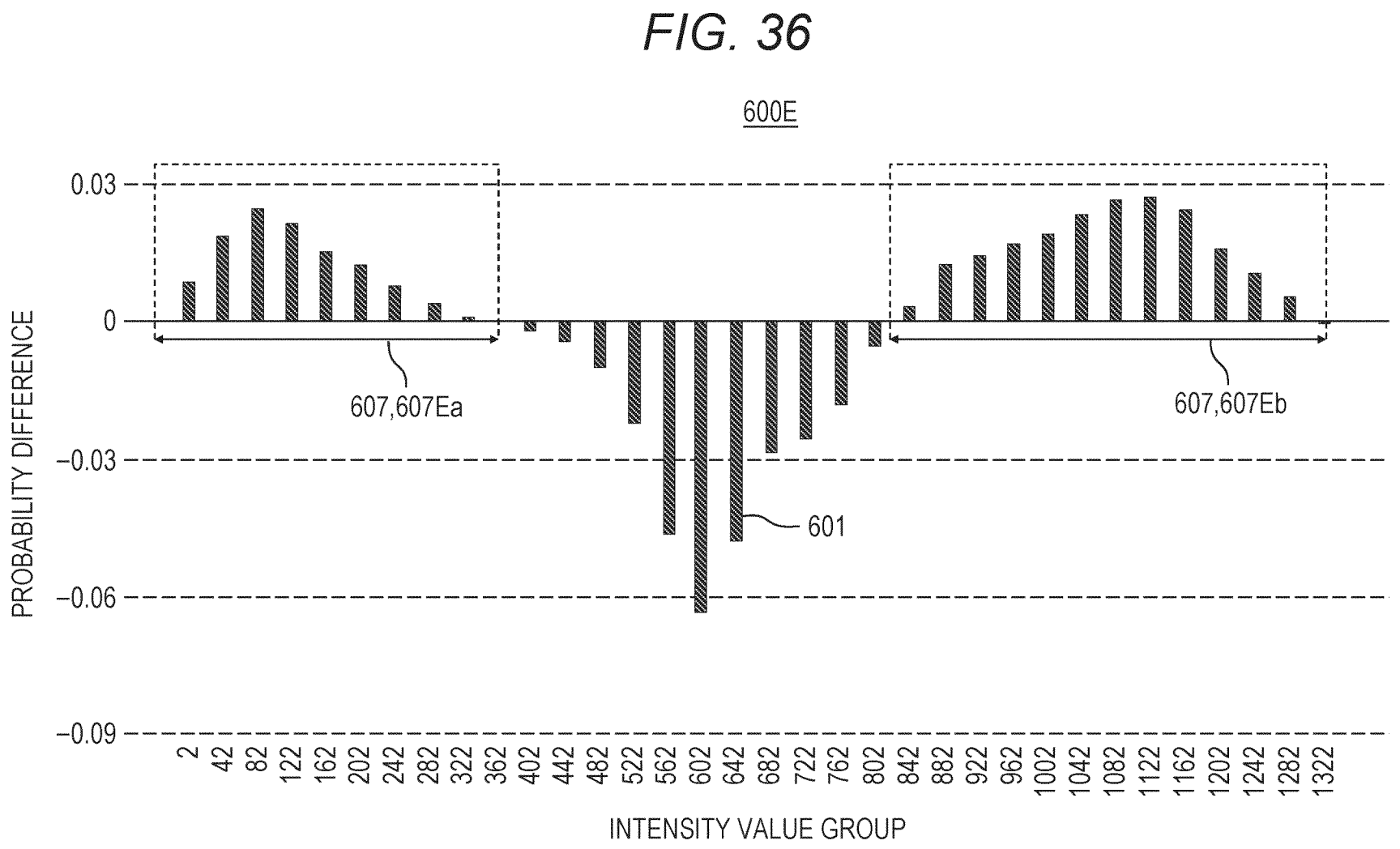

FIG. 36 is a diagram illustrating an example of a probability difference distribution 600E of the combined component image 260 (see FIG. 34B), used in the third embodiment.

In FIG. 36, the horizontal axis represents an intensity value group, and the vertical axis represents the probability difference 601.

The probability difference distribution in FIG. 36 is generated in step S151 of FIG. 32. FIG. 36 illustrates an example of the probability difference 601 obtained by subtracting the intensity value group probability distribution 500E (peripheral region histogram 502E in FIG. 35) of the peripheral region 222 (see FIG. 34A) from the intensity value group probability distribution 500E (inner region histogram 501E in FIG. 35) of the inner region 212 (see FIG. 34A) of the combined component image 260. In the diagram illustrated in FIG. 36, two mountains are formed. That is, there are two intensity intervals 607Ea and 607Eb (607).

(Setting of Detection Range)

Figure 37:
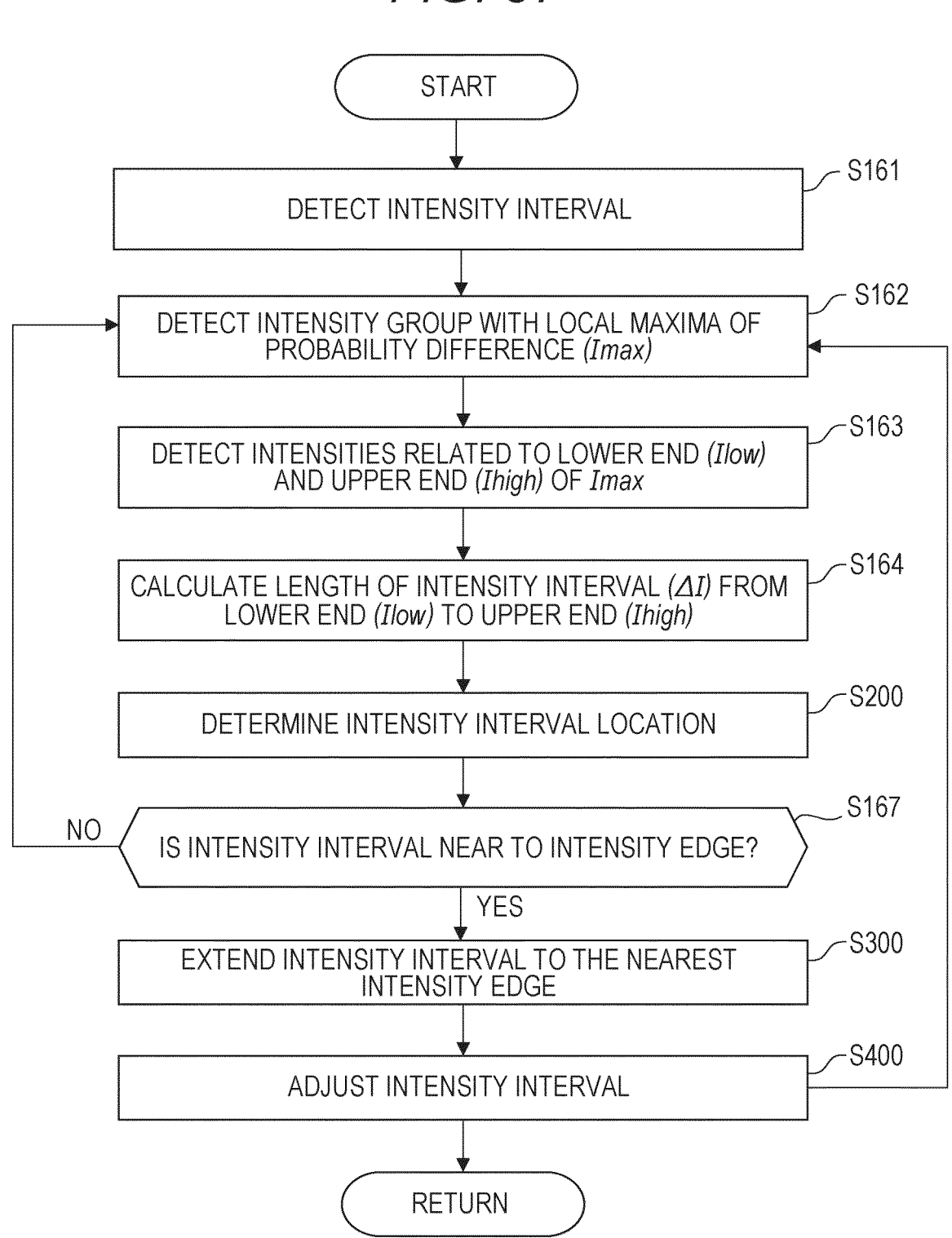
FIG. 37 is a flowchart illustrating a detailed procedure of setting a detection range for the combined component image.

FIG. 37 is a flowchart illustrating a detailed procedure of setting the detection range for the combined component image 260 (see FIG. 34B). FIG. 37 illustrates the processing of step S160B of FIG. 32 in detail. A description is made with reference to FIGS. 12A and 36 as appropriate.

As illustrated in FIG. 36, a plurality of intensity intervals 607 associated with the number of detected local maxima may be detected according to the shape of the probability difference distribution 600E. Unlike the component-by-component analysis shown in the first embodiment, the lesion site from the combined component image 260 may exhibit both low signal characteristics and high signal characteristics, and thus is not limited to a single intensity interval 607. That is, in the third embodiment, in the probability difference distribution 600E, the intensity interval 607 far from both the lower end 602 (see FIG. 12A) and the upper end 603 (see FIG. 12A) is discarded, but detection range setting processing is performed on the intensity intervals 607 other than the above-described intensity interval 607.

First, the detection range setting unit 107 detects an intensity interval 607 (Detect intensity interval: S161 in FIG. 37).

The processing in step S161 is similar to the processing in step S161 in FIG. 13.

Then, in FIG. 37, the processing in steps S162 to S400 is performed for each intensity intervals 607.

First, the detection range setting unit 107 detects an intensity value group with a local maxima of the probability difference 601 of the combined component image 260 (Detect Intensity group with local maxima of probability difference (Imax): S162 in FIG. 37). The local maxima is defined by an intensity value group with a maximum value of the probability difference 601 in each of the intensity intervals 607 to be processed.

Hereinafter, the intensity value group (local maxima) in which the probability difference 601 is maximum is referred to as the maximum intensity value group 604 (Imax: see FIGS. 12A to 12C).

Next, the detection range setting unit 107 detects intensity value groups related to the minimum value 605 (Ilow) and the maximum value 606 (Ihigh) in the intensity interval 607 (Detect intensities related to lower end (Ilow) and upper end (Ihigh) of Imax: S163 in FIG. 37). Linear extrapolation or linear interpolation can be considered for the detection of the minimum value 605 and the maximum value 606, but the extrapolation or interpolation is not limited to the "linear" method.

Subsequently, the detection range setting unit 107 calculates the length ($\Delta I$) of the intensity interval 607 from the minimum value 605 (Ilow) to the maximum value 606 (Ihigh) (Calculate length of intensity interval ($\Delta I$) from lower end (Ilow) to upper end (Ihigh): S164 in FIG. 37).

Here, in FIG. 13, when a plurality of intensity intervals 607 is detected in step S165, any one of the intensity intervals 607 is selected in step S166, but these steps are not performed in FIG. 37.

In the example of FIG. 36, two intensity intervals 607Ea and 607Eb are found in the probability difference 601 of the combined component image 260.

In step S200 of FIG. 37, the detection range setting unit 107 determines the location of the intensity interval 607 (Determine intensity interval location). This processing is similar to the processing performed in step S200 of FIG. 13 and FIG. 14.

Subsequently, the detection range setting unit 107 determines whether the location of any of the intensity intervals 607 is near to one of the edges of the lower end 602 (see FIG. 12A: I0) and the upper end 603 (see FIG. 12A: Iend) (Is intensity interval near to intensity edge?: S167 in FIG. 37). The processing of step S167 in FIG. 37 is similar to the processing of step S167 in FIG. 13.

When it is determined that the location of any of the intensity intervals 607 is not near to both the edges (no in S167 of FIG. 37), the detection range setting unit 107 returns the processing to step S162 and performs the processing on the next intensity interval 607. When there is no next intensity interval 607, the detection range setting unit 107 ends the processing.

When the intensity interval 607 is near to the edge (yes in S167), the detection range setting unit 107 extends the intensity interval 607 to the nearest edge (Extend intensity interval to the nearest intensity edge: S300 in FIG. 37). Then, the detection range setting unit 107 adjusts the intensity interval 607 to be a determined detection range (Adjust intensity interval: S400 in FIG. 37). Steps S300 and S400 are similar to steps S300 and S400 in FIG. 13.

According to the third embodiment, the lesion site highlighting processing can be performed on the combined component image obtained by synthesizing the component image 401 of the component of interest to the user.

The present invention is not limited to the embodiments described above, and various modified examples are included. For example, the above-described embodiments have been described in detail in order to explain the present invention in an easy-to-understand manner, and are not necessarily limited to those having all the configurations described. Further, a part of the configuration of a certain embodiment can be replaced with the configuration of another embodiment, and the configuration of another embodiment can be added to the configuration of the certain embodiment. Besides, a part of the configuration of each embodiment can be added to the configuration of another embodiment, can be deleted, and can be replaced with the configuration of another embodiment.

In addition, in the present embodiment, the lesion site highlighting processing is performed on the medical image 201, but the present invention is not limited thereto. That is, the image processing apparatus 1 of the present embodiment can be used for processing of highlighting a predetermined site in an image other than the medical image 201.

Further, in the present embodiment, the medical image 201 is an image related to the brain, but may be an image related to an organ other than the brain.

Further, the configurations, functions, image acquisition unit 101 to display processing unit 110, 3D image processing unit 110A, storage device 120, and the like described above may be implemented by hardware, for example, by designing some or all of them with an integrated circuit or the like. Moreover, as illustrated in FIG. 3, each of the above-described configurations, functions, and the like may also be implemented through software by using a processor such as CPU to interpret and execute a program for realizing each of the functions. Information such as a program, table, and file for realizing each of the functions may be stored not only in a hard disk (HD) but also in a storage device, such as a memory or a solid state drive (SSD), or a storage medium, such as an integrated circuit (IC) card, a secure digital (SD) card, or a digital versatile disc (DVD).

Furthermore, in each embodiment, control lines and information lines considered to be necessary for description are illustrated, and not all control lines and information lines in a product are necessarily illustrated. In practice, it may be considered that almost all the configurations are connected to each other.

What is claimed is:
1. An image processing apparatus comprising:
a region setting unit configured to set, for a first region set in a first image as a region including a region of interest in the first image, a second region in the first image, the second region being a region that is near the first region and that does not include the first region;
an intensity value frequency distribution calculation unit configured to calculate a first intensity value frequency distribution that is information related to distribution of a number of pixels having a predetermined intensity value for the first region and calculate a second intensity value frequency distribution that is information related to distribution of a number of pixels having a predetermined intensity value for the second region;
a probability difference calculation unit configured to calculate a probability difference frequency distribution by calculating a difference value between the first intensity value frequency distribution and the second intensity value frequency distribution for each of the predetermined intensity values;
an image processing unit configured to generate a plurality of second images decomposed based on the first image in accordance with a predetermined criterion;
a detection range setting unit configured to apply a detection range setting algorithm to each of the plurality of second images and set a detection range of the intensity value of the first image for each of the second images based on the difference value;
a pixel selection unit configured to select a pixel to be highlighted for each of the plurality of second images based on the detection range set for each of the second images; and
an output processing unit configured to output, to an output unit, a third image in which the pixel selected by the pixel selection unit is highlighted.
2. The image processing apparatus according to claim 1, wherein the pixel selection unit synthesizes the selected pixel to form a fourth image.
3. The image processing apparatus according to claim 2, further comprising a 3D image processing unit, wherein
the fourth image is present in a plurality of numbers, and the 3D image processing unit stacks the plurality of fourth images to form a fifth image as a 3D image.
4. The image processing apparatus according to claim 3, wherein
the 3D image processing unit is configured to
respectively compute a reference of pixel number, that is a pixel number of the highlighted pixel in one of the fourth images, a reference of center that is a center of the highlighted pixel, and a reference of spread that is an average of distances between the reference of center and each pixel constituting the highlighted pixel,
respectively compute an adjacent pixel number, that is a pixel number of the highlighted pixel, an adjacent center that is a center of the highlighted pixel, and an adjacent spread that is an average of distances between the adjacent center and each pixel constituting the highlighted pixel, in the fourth image different from the fourth image in which the reference of pixel number, the reference of center, and the reference of spread are computed, and continue to select the fourth image, as the fourth image constituting the fifth image, from the plurality of fourth images until a ratio between the adjacent pixel number and the reference of pixel number is less than a first value as a predetermined value, a distance between the adjacent center and the reference of center is greater than a second value as a predetermined value, or a ratio between the adjacent spread and the reference of spread is greater than a third value as a predetermined value.

5. The image processing apparatus according to claim 2, wherein the image processing unit is configured to generate an image in which a predetermined second image among the plurality of second images is synthesized, and set the image as a new second image.

6. The image processing apparatus according to claim 1, wherein the detection range setting unit is configured to set, as the detection range, an interval in which the difference value has a positive value in the probability difference frequency distribution, extend a minimum value of the detection range to a lower end in the probability difference frequency distribution when the detection range is near to the lower end, and extend a maximum value of the detection range to an upper end in the probability difference frequency distribution when the detection range is near to the upper end.

7. The image processing apparatus according to claim 6, wherein when a plurality of the detection ranges is detected, the detection range setting unit selects the detection range with the greatest area of the probability difference frequency distribution in the detection range.

8. The image processing apparatus according to claim 6, wherein the detection range setting unit is configured to calculate a first cumulative intensity value probability by accumulating the second intensity value frequency distribution from the side of the minimum value of the detection range to the side of the maximum value of the detection range, for the second region, compute a second cumulative intensity value probability by accumulating the difference value from the side of the minimum value of the detection range to the side of the maximum value of the detection range, select the intensity value based on a predetermined threshold and the first cumulative intensity value probability, execute a first method of determining the second cumulative intensity value probability corresponding to the selected intensity value as a first selected cumulative intensity value probability, compute a third cumulative intensity value probability by accumulating the second intensity value frequency distribution from the side of the maximum value of the detection range to the side of the minimum value of the detection range, compute a fourth cumulative intensity value probability by accumulating the difference value from the side of the maximum value of the detection range to the side of the minimum value of the detection range, for the second region, select the intensity value based on a predetermined threshold and the third cumulative intensity value probability, execute a second method of determining the fourth cumulative intensity value probability corresponding to the selected intensity value as a second selected cumulative intensity value probability, make a magnitude relation comparison between the first selected cumulative intensity value probability and the second selected cumulative intensity value probability, determine the maximum value of the detection range as an intensity value selected by the first method when the first selected cumulative intensity value probability is greater than the second selected cumulative intensity value probability, and determine the minimum value of the detection range as an intensity value selected by the second method when the second selected cumulative intensity value probability is greater than the first selected cumulative intensity value probability.

9. The image processing apparatus according to claim 1, wherein the first image is a medical image captured by a medical image capturing unit.

10. The image processing apparatus according to claim 1, wherein the first image is an image related to a brain.

11. An image processing method, comprising causing an image processing apparatus that highlights a predetermined region of a first image to perform:

a region setting processing of setting, for a first region set in the first image as a region including a region of interest in the first image, a second region in the first image, the second region being a region that is near the first region and that does not include the first region;

intensity value frequency distribution calculation processing of calculating a first intensity value frequency distribution that is information related to distribution of a number of pixels having a predetermined intensity value for the first region and calculating a second intensity value frequency distribution that is information related to distribution of a number of pixels having a predetermined intensity value for the second region;

probability difference calculation processing of calculating a probability difference frequency distribution by calculating a difference value between the first intensity value frequency distribution and the second intensity value frequency distribution for each of the predetermined intensity values;

component decomposition processing of generating a plurality of second images decomposed based on the first image in accordance with a predetermined criterion;

detection range setting processing of applying a detection range setting algorithm to each of the plurality of second images and setting a detection range of the intensity value of the first image for each of the second images based on the difference value;

pixel selection processing of selecting a pixel to be highlighted for each of the plurality of second images based on the detection range set for each of the second images; and output processing of outputting, to an output unit, a third image in which the pixel selected by the pixel selection unit is highlighted.

* * * * *